US007166697B1

US 7,166,697 B1

(12) United States Patent
Galanis et al.

(10) Patent No.: US 7,166,697 B1
(45) Date of Patent: Jan. 23, 2007

(54) V-LIKE DOMAIN BINDING MOLECULES

(75) Inventors: Maria Galanis, Waverley (AU); Peter John Hudson, Blackburn (AU); Robert Alexander Irving, Mulgrave (AU); Stewart Douglas Nuttall, Ivanhoe (AU)

(73) Assignee: Diatech Pty. Ltd., Queensland (AU)

( * ) Notice: Subject to any disclaimer, the term of this patent is extended or adjusted under 35 U.S.C. 154(b) by 0 days.

(21) Appl. No.: 09/623,611

(22) PCT Filed: Mar. 5, 1999

(86) PCT No.: PCT/AU99/00136

§ 371 (c)(1),
(2), (4) Date: Oct. 6, 2000

(87) PCT Pub. No.: WO99/45110

PCT Pub. Date: Sep. 10, 1999

(30) Foreign Application Priority Data

Mar. 6, 1998 (AU) .................................... PP2210

(51) Int. Cl.
*C07K 14/00* (2006.01)
*C12P 21/08* (2006.01)
*A61K 39/395* (2006.01)
*A01N 37/18* (2006.01)
*G01N 33/53* (2006.01)

(52) U.S. Cl. .................. 530/350; 530/311; 530/387.3; 530/808; 530/810; 530/812; 424/134.1; 514/2; 435/7.1

(58) Field of Classification Search ................ 530/350, 530/311, 387.3, 808, 810, 812; 424/134.1, 424/192.1; 514/2
See application file for complete search history.

(56) References Cited

U.S. PATENT DOCUMENTS

| 5,434,131 | A | | 7/1995 | Linsley et al. |
| 5,504,069 | A | * | 4/1996 | Bogden et al. |
| 5,728,821 | A | | 3/1998 | Yelton et al. |
| 5,773,253 | A | | 6/1998 | Linsley et al. |
| 5,792,456 | A | | 8/1998 | Yelton et al. |
| 5,792,852 | A | | 8/1998 | Do Couto et al. |
| 5,804,187 | A | | 9/1998 | Do Couto et al. |
| 5,844,095 | A | | 12/1998 | Linsley et al. |
| 5,849,877 | A | | 12/1998 | Ring |
| 5,851,795 | A | | 12/1998 | Linsley et al. |
| 6,383,487 | B1 | | 5/2002 | Amlot et al. |
| 6,521,230 | B1 | | 2/2003 | Amlot et al. |
| 2003/0134386 | A1 | * | 7/2003 | Koide |

FOREIGN PATENT DOCUMENTS

| WO | WO91/10438 | 7/1991 |
| WO | WO 92/01787 A | 2/1992 |
| WO | WO 92/15671 | 9/1992 |
| WO | WO 93/00431 | 1/1993 |
| WO | WO 94/05690 | 3/1994 |
| WO | WO 94/12625 | 6/1994 |
| WO | WO 95/01994 | 1/1995 |
| WO | WO 96/06625 | 3/1996 |
| WO | WO 96/08564 | 3/1996 |
| WO | WO 96/18105 | 6/1996 |
| WO | WO 96/36714 | 11/1996 |
| WO | WO 96/39514 | 12/1996 |
| WO | WO 97/28267 | 8/1997 |
| WO | WO 98/33513 | 8/1998 |
| WO | WO 98/33513 A | 8/1998 |

OTHER PUBLICATIONS

Metzler et al. Nat. Structural Biol. 1997; 4(7):527-531.*
Bajorath J. Mol. Model 1999; 5:169-170.*
Nuttall et al. PROTEINS: Structure, Function, and Genetics 1999; 36:217-227.*
Cai et al. Proc. Natl. Acad. Sci. USA 1996; 93:6280-6285.*
Jung et al., Protein Engineering, vol. 10, No. 8, pp. 959-966, 1997.
Davies et al., Protein Engineering, Medline Abstract, vol. 9, No. 6, pp. 531-537, Jun. 1996
Peach et al., J. Exp. Med., vol. 180, pp. 2049-2058, Dec. 1994.
Patten et al., The Journal of Immunology, vol. 150, No. 6, pp. 2281-2294, Mar. 15, 1993.
Linsley et al. (1995) "Binding stoichiometry of the cytotoxic T lymphocyte—associated Molecule-4 (CTLA-4)" Journal of Biological Chemistry, vol. 270, No. 25, pp. 15417-15424.

* cited by examiner

*Primary Examiner*—Phillip Gambel
*Assistant Examiner*—Ilia Ouspenski
(74) *Attorney, Agent, or Firm*—Frommer Lawrence & Haug LLP; Thomas J. Kowalski; Anne-Marie C. Yvon

(57) ABSTRACT

The present invention relates to binding moieties comprising at least one monomeric V-like domain (VLD) derived from a non-antibody ligand, the at least one monomeric V-like domain being characterized in that at least one CDR loop structure or part thereof is modified or replaced such that the solubility of the modified VLD is improved when compared with the unmodified VLD.

22 Claims, 17 Drawing Sheets

Figure 1A: CTLA-4 VLD-SPECIFIC OLIGONUCLEOTIDES

| OLIGONUCLEOTIDE | NUMBER | SIZE | SEQUENCE[1] | FEATURES |
|---|---|---|---|---|
| For 5' CTLA-4 amplification | 3553<br>5023<br>5671 | 54 | TTATTACTCgCggCCCAgCCggCCATggCCgCAATgCACgTggCC<br>CAgCCTgCT (SEQ ID NO:2) | forward primer + SfiI site |
| For 5' CTLA-4 amplification | 5445 | 60 | TTATTACTCgCggCCCAgCCggCCATggCCgCAATgCACgTggCC<br>CAgCCTgCTgTggTA (SEQ ID NO:3) | forward primer + SfiI site |
| For 5' CTLA-4 amplification | 5443 | 45 | TCTCACAgTgCACAggCAATgCACgTggCCCAgCCTgCTgTggTA (SEQ ID NO:4) | forward primer + ApaLI site |
| For 5' CTLA-4 amplification | 4851 | 39 | TCTCACAgTgCACAggCAATgCACgTggCCCAgCCTgCT (SEQ ID NO:5) | forward primer + ApaLI site |
| For 5' CTLA-4 amplification | 5467 | 43 | gCCCAgCCggCCgAATTCgCAATgCACgTggCCCAgCCTgCTg (SEQ ID NO:6) | forward primer + EcoRI site |
| For 5' CTLA-4 amplification | | 60 | GCAGCTAATACGACTCACTATAGGAACAGACCACCATGGA<br>CGTGGCCCAGCCTGCTGTGG (SEQ ID NO:7) | ribosomal display |
| For 3' CTLA-4 amplification | 4316<br>5022<br>5670 | 42 | ATCTgCggCCgCTACATAAATCTgggTACCgTTgCCgATgCC (SEQ ID NO:8) | reverse primer + NotI site |
| For 3' CTLA-4 amplification | 4486 | 66 | gCTgAATTCTgATCAgTgATggTgATggTgATgTgCggCCgCgTCAg<br>AATCTgggCACggTTCTgg (SEQ ID NO:9) | |
| For 3' CTLA-4 amplification | | 51 | GCCCTTGGGCCGGAGATGGTCTGCTTCAGTGGGCGAGGGC<br>AGGTCTGTGTG (SEQ ID NO:10) | ribosomal display 1 |
| For 3' CTLA-4 amplification | | 49 | CGAGGGCAGGTCTGTGTGGGTCACGGTGCACGTGAACCTCT<br>CCCCGGAG (SEQ ID NO:11) | ribosomal display 2 |

Figure 1B: CTLA-4 VLD-SPECIFIC OLIGONUCLEOTIDES

| OLIGONUCLEOTIDE | NUMBER | SIZE | SEQUENCE | FEATURES |
|---|---|---|---|---|
| For 3' CTLA-4 amplification | | 51 | CGTGAACCTCTCCCCGGAGTTCCAGTCATCCTCGCAGATGC TGGCCTCACC (SEQ ID NO:12) | ribosomal display 3 |
| For CDR1-somatostatin | 4585 | 84 | AgCTTTgTgTgTgAgTATgCAgCTggCTgCAAgAATTTCTTCTggA AgACTTTCACATCTgTgCCACTgAggTCCgggTgACA (SEQ ID NO:13) | forward primer + Som |
| For CDR3-somatostatin | 4586 | 84 | CTgggTACCgTTgCCgATgCCACAggATgTgAAAgTCTTCCAgAA gAAATTCTTgCAgCCAgCCTCCACCTTgCAgATgTAgAg (SEQ ID NO:14) | reverse primer + Som |
| For CDR1-som-randomisation | 4835 | 75 | AgCTTTgTgTgTgAgTATgCAgCTggCTgCAAgAATNNg/TNNg/T NNg/TNNg/TNNg/TNNg/TACATCCTgTgCCACTgAggTC (SEQ ID NO:15) | |
| For CDR3-som-randomisation | 4836 | 75 | CTgggTACCgTTgCCgATgCCACAggATgTA/CNNA/CNNA/CNN A/CNNA/CNNA/CNNATTCTTgCAgCCAgCCTCCACCTTgCA (SEQ ID NO:16) | |
| For CDR2 haemagglutinin tag | 4766 | 21 | gTAggTTgCCgCACAgACTTC (SEQ ID NO:17) | back primer for splice overlap |
| For CDR2 haemagglutinin tag | 4775 | 66 | gAAgTCTgTgCggCAACCTACCCgTATgACgTTCCgACTACgCC CTAgATgATTCCATCTgCACg (SEQ ID NO:18) | forward primer tag overlap |
| For CDR-1 anti-lysozyme | 5232 | 78 | gCCAgCTTTgTgTgTgAgTATgCCAgTggCTACACCATCgggCCgT ACTgCATgggCgTCCgggTgACAgTgCTTCgg (SEQ ID NO:19) | |
| For CDR-2 anti-lysozyme | 5228 | 60 | TgTgCggCAgCCATCAACATgggCggTggCATCACCTTCCTAgAT gATTCCATCTgCACg (SEQ ID NO:20) | Forward |

Figure 1C: CTLA-4 VLD-SPECIFIC OLIGONUCLEOTIDES

| OLIGONUCLEOTIDE | NUMBER | SIZE | SEQUENCE | FEATURES |
|---|---|---|---|---|
| For CDR-2 anti-lysozyme | 5229 | 60 | ATCTAggaAaggTgATgCCACCgCCCATgTTgATggCTgCCgCACAgACTTCAgTCACCTg (SEQ ID NO:21) | Reverse |
| For CDR-3 anti-lysozyme | 5230 | 69 | CAgCCCgTggCCgCACTCgTAgTAggACgCgTAgATCgTcGAgTCCACCTTgCAgATgTAgAgTCCCgT (SEQ ID NO:22) | |
| For CDR-3 anti-lysozyme | 5231 | 72 | AATCTgggTACCgTTgCCgATgCCggAgTCATAgCCgTACCCTCCCgTggACAgCCCgTggCCgCACTCgTA (SEQ ID NO:23) | |
| For CDR-1 anti-melanoma | 5341 | 78 | gCCAgCTTTgTgTgTgAgTATgCCAgTggATTCACCTTCAgTTCCTACgCCATgTCCgTCCgggTgACAgTgCTTCgg (SEQ ID NO:24) | |
| For CDR-2 anti-melanoma | 5338 | 51 | gCCATCTCCggAgATCCggAggCTCgACCTACCTAgATgATTCCATCTgCACg (SEQ ID NO:25) | Forward |
| For CDR-2 anti-melanoma | 5339 | 54 | gTAggTCgAgCCTCgAgCTCCggATCCggAgAgATggCTgCCgCACAgACTTCAgTCACCTg (SEQ ID NO:26) | Reverse |
| For CDR-3 anti-melanoma | 5351 | 69 | CACgTCCATgTAgTAgTCTCCCCTCCgCCgCgCAgTCCCCAgCCCACCTTgCAgATgTAgAgTCCCgT (SEQ ID NO:27) | |
| For CDR-3 anti-melanoma | 5340 | 51 | AATCTgggTACCgTTgCCgATgCCCACgTCCATgTAgTCTCCCTCCCTC (SEQ ID NO:28) | |
| CDR1 Randomisation | 4483 | 66 | AgCTTTgTgTgTgAgTATgCANNg/TNNg/TNNg/TNNg/TNNg/TNNg/TNNg/TNNg/TgCCACTgAggTCCgggTgACA (SEQ ID NO:29) | forward primer / 8 residue random loop |
| CDR1 Randomisation | 4484 | 68 | CACgTggCCCAgCCTgCTgTggTACTggCCAgCAgCCAgAggCATCgCCAgCTTTgTgTgTgAgTATgC (SEQ ID NO:30) | extension primer |
| CDR1 Randomisation | 4254 | 66 | gTgTgTgAgTACgCgTNCNNg/CNNg/CNNg/CNNg/CNNg/CNNg/CNNg/CTgCNNg/CgCTACTgAggTTCgTgTgACCgTC (SEQ ID NO:31) | forward primer with MluI, AflII sites |

Figure 1D: CTLA-4 VLD-SPECIFIC OLIGONUCLEOTIDES

| OLIGONUCLEOTIDE | NUMBER | SIZE | SEQUENCE | FEATURES |
|---|---|---|---|---|
| CDR1 Randomisation | 5449 | 73 | gCCAgCTTTgTgTgTgAgTATgCA(NN$^8$/$_T$)$_7$ggCgTCCgggTgACAgTgCTTCggCAgg (SEQ ID NO:32) | |
| CDR1 Randomisation | 5451 | 82 | gCCAgCTTTgTgTgTgAgTATgCA(NN$^8$/$_T$)$_8$TgCNN$^8$/$_T$ggCgTCCgggTgACAgTgCTTCggCAgg (SEQ ID NO:33) | |
| CDR1 Randomisation | 5452 | 82 | gCCAgCTTTgTgTgTgAgTATgCA(NN$^8$/$_T$)$_2$($^T$/$_C$/$_A$/$_C$)(NN$^8$/$_T$)$_2$($^T$/$_C$/$_A$/$_C$)TgC(NN$^8$/$_T$)ggCgTCCgggTgACAgTgCTTCggCAgg (SEQ ID NO:34) | |
| CDR1 Randomisation | 5450 | 70 | gCCAgCTTTgTgTgTgAgTATgCATCTCCAggC(NN$^8$/$_T$)$_4$gTCCgggTgACAgTgCTTCggAgg (SEQ ID NO:35) | |
| CDR1 Randomisation | 5446 | 70 | gCCAgCTTTgTgTgTgAgTATgCATCTCCAggCNN$^8$/$_T$TgCNN$^8$/$_T$NN$^8$/$_T$gTCCgggTgACAgTgCTTCggCAgg (SEQ ID NO:36) | |
| CDR2 Randomisation | 5447 | 68 | gTgACTgAAgTCTgTgCggCAACCTACNN$^G$/$_T$NN$^G$/$_T$gggNN$^G$/$_T$gAgTTgACCTTCCTAgATgATTCCATCTg (SEQ ID NO:37) | |
| CDR2 Randomisation | 5441 | 30 | gTAggTTgCCgCACAgACTTCAgTCAgTCACCtg (SEQ ID NO:38) | |
| CDR2 Randomisation | 5448 | 68 | gTgACTgAAgTCTgTgCggCATgCTACNN$^G$/$_T$NN$^G$/$_T$gggNN$^G$/$_T$gAgTTgACCTTCCTAgATgATTCCATCTg (SEQ ID NO:39) | |
| CDR2 Randomisation | 5442 | 30 | gTAgCATgCCgCACAgACTTCAgTCACCtg (SEQ ID NO:40) | |
| CDR3 Randomisation | 4482 | 69 | CTgggTACCgTTgCCgATgCCC/ANNC/ANNC/ANNC/ANNC/ANNC/ANNCTCCACCTTgCAgATgTAgAg (SEQ ID NO:41) | reverse primer + 9 residue random loop |
| CDR3 Randomisation | 4275 | 67 | AggTggAA(NNg/C)$_6$TgCNNg/CNNg/CNNg/CNNg/CNNg/CNNg/CggCATCgCAACggTAC (SEQ ID NO:42) | forward primer with PstI and KpnI overhangs |

Figure 1E: CTLA-4 VLD-SPECIFIC OLIGONUCLEOTIDES

| OLIGONUCLEOTIDE | NUMBER | SIZE | SEQUENCE | FEATURES |
|---|---|---|---|---|
| CDR3 Randomisation | 5470 | 78 | AATCTgggTACCgTTgCCgATgCC($^A/_C$NN)$_{10}$CACCTTgCAgATgTAgAgTCCCgT (SEQ ID NO:43) | |
| CDR3 Randomisation | 5474 | 93 | AATCTgggTACCgTTgCCzgATgCCCCAg($^A/_C$NN)$_{13}$CTCCACCTTgCAgATgTAgAgTCCCgT (SEQ ID NO:44) | |
| CDR3 Randomisation | 5471 | 81 | AATCTgggTACCgTTgCCgATgCC($^A/_C$NN)$_4$gCA($^A/_C$NN)$_6$CACCTTgCAgATgTAgAgTCCCgT (SEQ ID NO:45) | |
| CDR3 Randomisation | 5472 | 87 | AATCTgggTACCgTTgCCgATgCC($^A/_C$NN)$_5$gCA($^A/_C$NN)$_7$CACCTTgCAgATgTAgAgTCCCgT (SEQ ID NO:46) | |
| CDR3 Randomisation | 5475 | 99 | AATCTgggTACCgTTgCCgATgCC($^A/_C$NN)$_6$gCA($^A/_C$NN)$_{10}$CACCTTgCAgATgTAgAgTCCCgT (SEQ ID NO:47) | |
| CDR3 Randomisation | 5473 | 87 | AATCTgggTACCgTTgCCgATgCC($^g/_A$$^T/_A$$^g/_A$)($^A/_C$NN)$_4$gCA($^A/_C$NN)$_7$CACACCTTgCAgATgTAgAgTCCCgT (SEQ ID NO:48) | |
| CTLA-4 codon-change | 5591 | 70 | ATgCACgTggCCCCAgCCTgCTgTggTgCTggCCAgCAgCCgTggCATCgCCAgCTTTgTgTgTgAATATg (SEQ ID NO:49) | |
| CTLA-4 codon-change | 5592 | 77 | gCCAgCTTTgTgTgTgAATATgCgTCTggCTATACCATCggCCCgTACTgCATgggTgTgCgTgTgACCgTCTgCg (SEQ ID NO:50) | |
| CTLA-4 codon-change | 5598 | 54 | gTgCgTgTgACCgTCTgCgTCAggCggATAgCCAggTgACCgAAgTTTgCgCg (SEQ ID NO:51) | |
| CTLA-4 codon-change | 5600 | 75 | CAggTgACCgAAgTTTgCgCggCAgCgATCAACATgggCggTggCATCACCTTCCTggATgATTCCATCCATCTgCACC (SEQ ID NO:52) | |
| CTLA-4 codon-change | 5599 | 66 | CAgACCCTggATggTCAggTTCACCTggTTACCTggAggTgCCggTgCAgATggAATCATCCAg (SEQ ID NO:53) | |
| CTLA-4 codon-change | 5597 | 57 | CACTTTgCAgATgTACAgACCggTATCCATggCACgCAgACCCTggATggTCAggTT (SEQ ID NO:54) | |

Figure 1F: CTLA-4 VLD-SPECIFIC OLIGONUCLEOTIDES

| CTLA-4 codon-change | 5606 | 66 | CAggCCATgACCgCATTCgTAATAAgACgCATAgATggTgCTAT CCACTTTgCAgATgTACAgACC (SEQ ID NO:55) | |
|---|---|---|---|---|
| CTLA-4 codon-change | 5607 | 69 | CTgggTACCgTTgCCgATgCCAGAATCgTAgCCATAgCCACCggT ggACAggCCATgACCgCATTCgTA (SEQ ID NO:56) | |

[1] All oligonucleotides are described 5' to 3'.
N represents combination of the four nucleotides.

Figure 2: Polynucleotide sequence of complete cDNA encoding human CTLA-4 and polypeptide sequence of the VLD of human CTLA-4.

A. Polynucleotide Encoding Human CTLA-4 cDNA (SEQ ID NO:57)

```
ATGGCTTGCC TTGGATTTCA GCGGCACAAG GCTCAGCTGA ACCTGGCTGC CAGGACCTGG CCCTGCACTC TCCTGTTTT...  80
TCTTCTCTTC ATCCCTGTCT TCTGCAAAGC AATGCACGTG GCCCAGCCTG CTGTGGTACT GGCCAGCAGC CGAGGCATCG... 160
CCAGCTTTGT GTGTGAGTAT GCATCTCCAG GCAAAGCCAC TGAGGTCCGG GTGACAGTGC TTCGGCAGGC TGACAGCCAG... 240
GTGACTGAAG TCTGTGCGGC AACCTACATG ACGGGGAATG AGTTGACCTT CCTAGATGAT TCCATCTGCA CGGGCACCTC... 320
CAGTGGAAAT CAAGTGAACC TCACTATCCA AGGACTGAGG GCCATGGACA CGGGACTCTA CATCTGCAAG GTGGAGCTCA... 400
TGTACCCACC GCCATACTAC CTGGGCATAG GCAACGGAAC CCAGATTTAT GTAATTGATC CAGAACCGTG CCCAGATTCT... 480
GACTTCCTCC TCTGGATCCT TGCAGCAGTT AGTTCGGGGT TGTTTTTTA TAGCTTTCTC CTCACAGCTG TTTCTTTGAG... 560
CAAAATGCTA AAGAAAAGAA GCCCTCTTAC AACAGGGGTC TATGTGAAAA TGCCCCCAAC AGAGCCAGAA TGTGAAAAGC... 640
AATTTCAGCC TTATTTTATT CCCATCAATT GA                                                       672
```

B. Polypeptide Sequence of Human CTLA-4 VLD (SEQ ID NO:58)

```
1          10         20         30         40         50         60         70         80
AMHVAQPAVV LASSRGIASF VCEYASPGKA TEVRVTVLRQ ADSQVTEVCA ATYMMGNELT FLDDSICTGT SSGNQVNLTI
           90         100        110        115
QGLRAMDTGL YICKVELMYP PPYYLGIGNG AQIYV
```

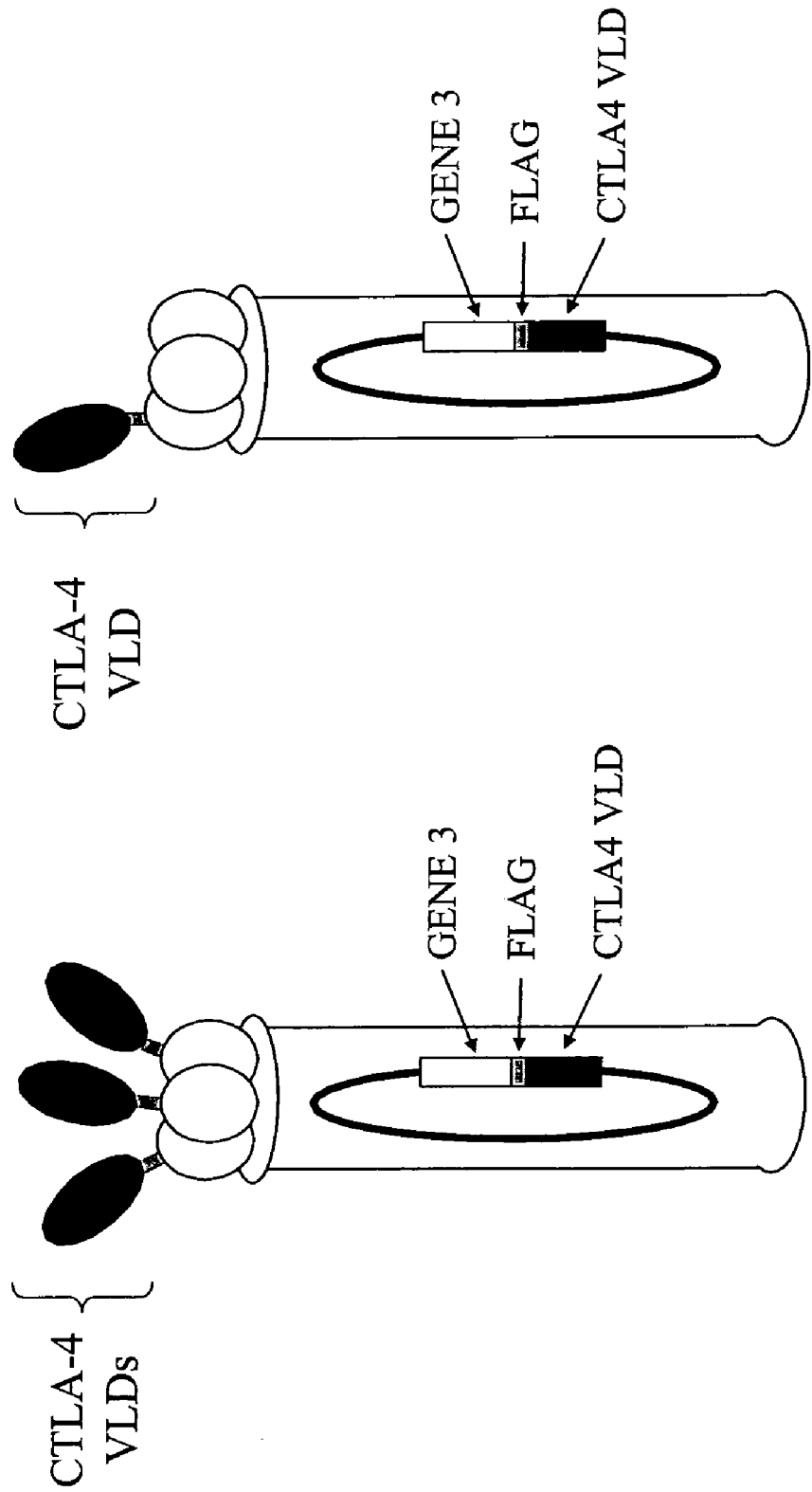
Figure 3: Phage display of CTLA-4 VLD STMs

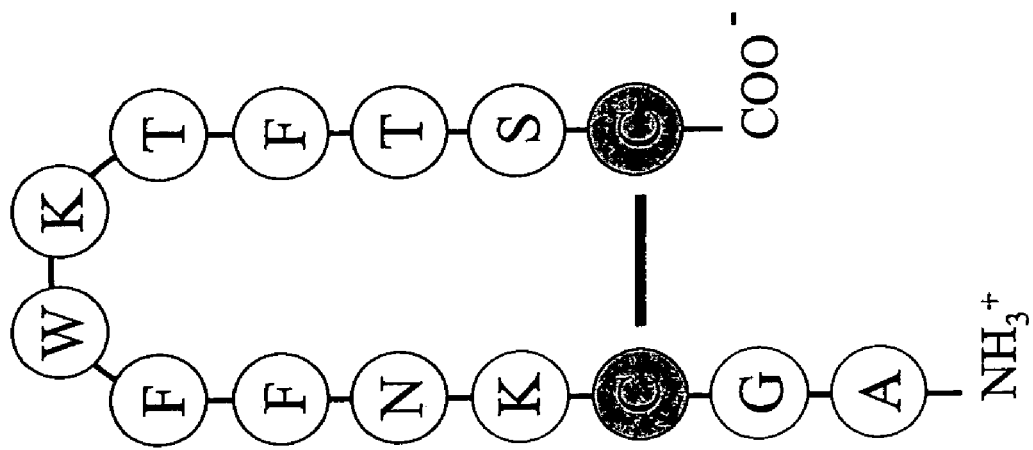
Figure 4: Schematic representation of the somatostatin peptide. (SEQ ID NO:139)

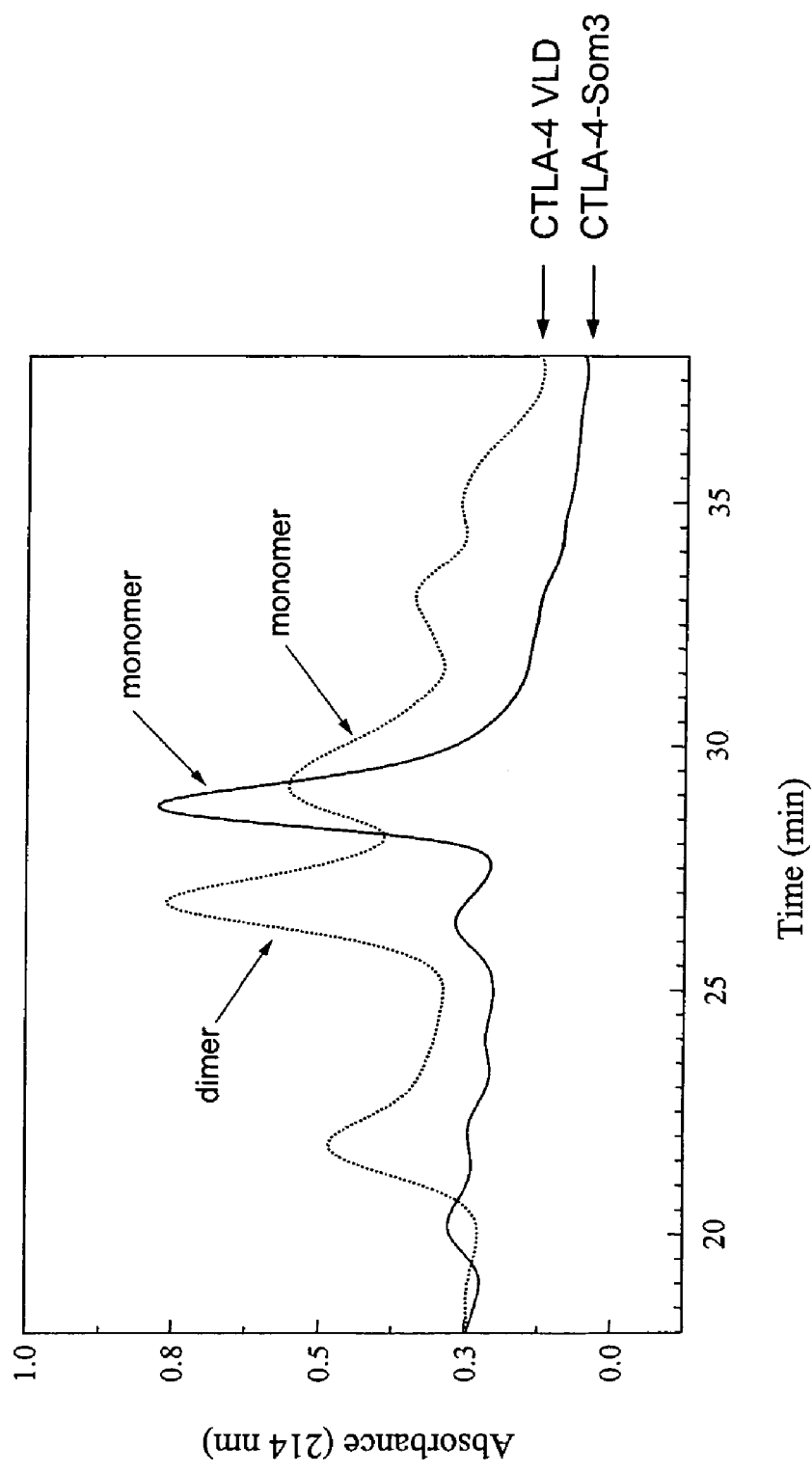
Figure 5: Comparison of the HPLC profiles of affinity purified CTLA-4 VLD and CTLA-4-Som3 STM Figure 6: Schematic diagram of CTLA-4 VLD CDR loop replacements.
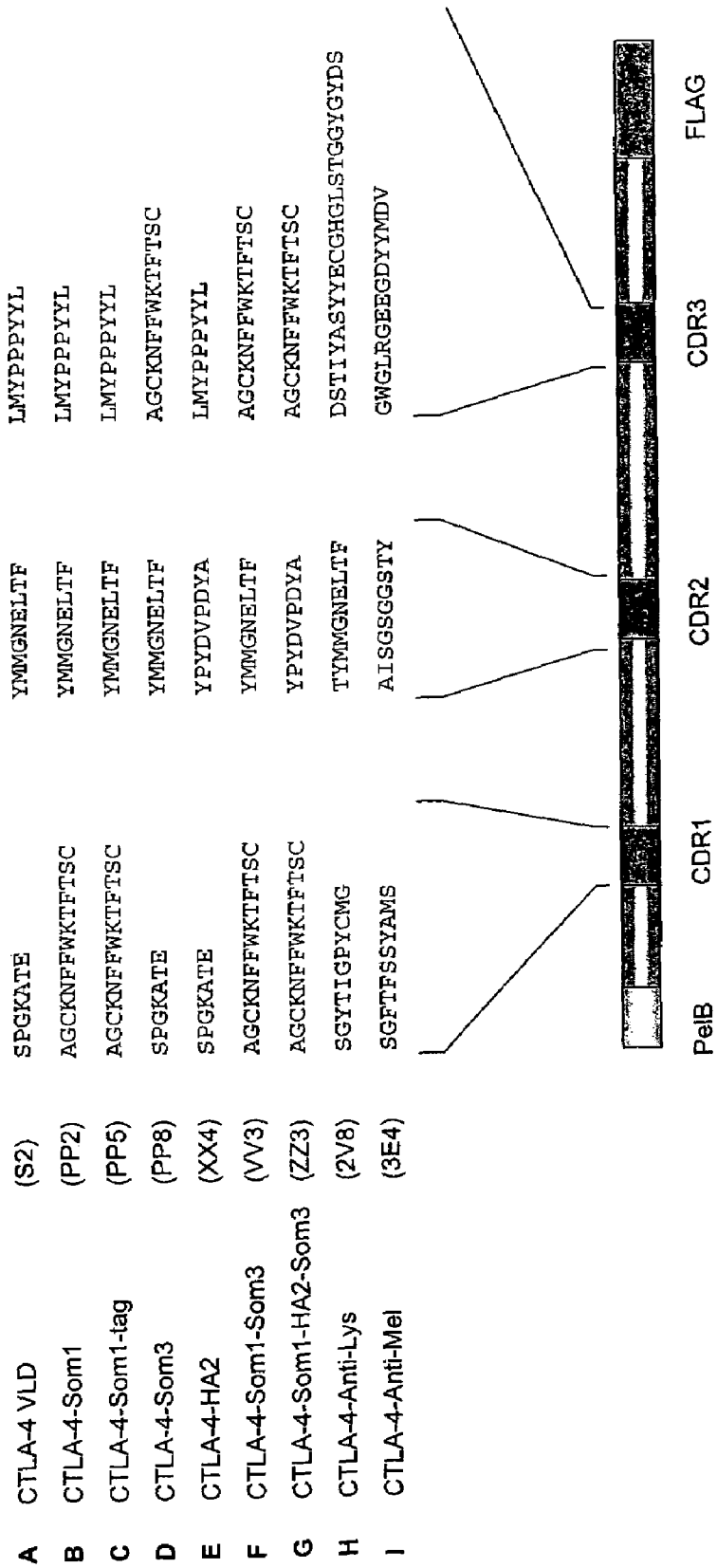

| | | | | | |
|---|---|---|---|---|---|
| A | CTLA-4 VLD | (S2) | SPGKATE | YMMGNELTF | LMYPPPYYL |
| B | CTLA-4-Som1 | (PP2) | AGCKNFFWKTFTSC | YMMGNELTF | LMYPPPYYL |
| C | CTLA-4-Som1-tag | (PP5) | AGCKNFFWKTFTSC | YMMGNELTF | LMYPPPYYL |
| D | CTLA-4-Som3 | (PP8) | SPGKATE | YMMGNELTF | AGCKNFFWKTFTSC |
| E | CTLA-4-HA2 | (XX4) | SPGKATE | YPYDVPDYA | LMYPPPYYL |
| F | CTLA-4-Som1-Som3 | (VV3) | AGCKNFFWKTFTSC | YMMGNELTF | AGCKNFFWKTFTSC |
| G | CTLA-4-Som1-HA2-Som3 | (ZZ3) | AGCKNFFWKTFTSC | YPYDVPDYA | AGCKNFFWKTFTSC |
| H | CTLA-4-Anti-Lys | (2V8) | SGYTIGPYCMG | TYMMGNELTF | DSTIYASYYECGHGLSTGGYGYDS |
| I | CTLA-4-Anti-Mel | (3E4) | SGFTFSSYAMS | AISGSGGSTY | GWGLRGEEGDYYMDV |

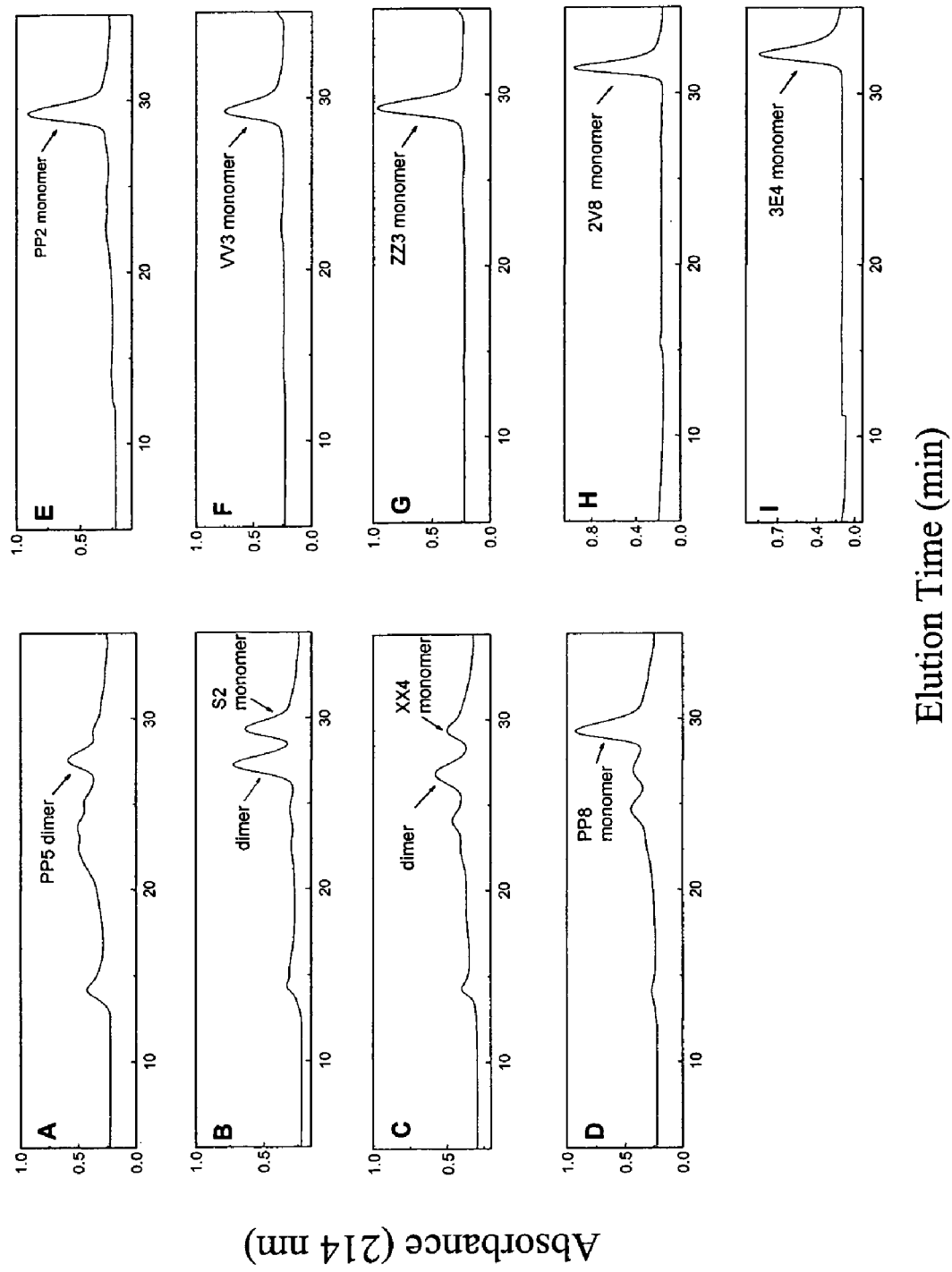
Figure 7: HPLC profiles of affinity purified recombinant CTLA-4 STMs

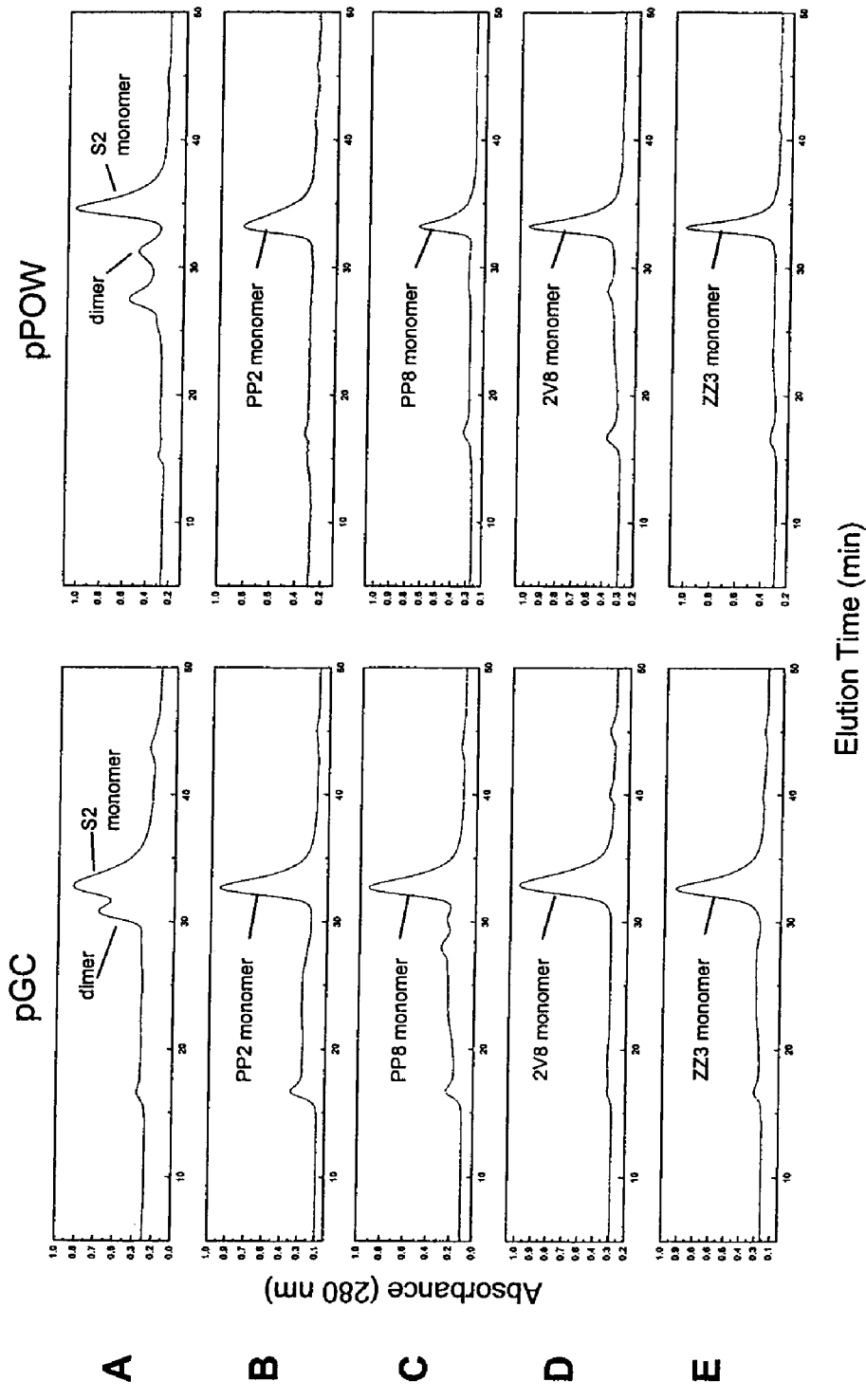
Figure 8: Comparison by size exclusion HPLC analysis of affinity purified CTLA-4 VLD STM constructs synthesised using bacterial expression vector pGC or pPOW.

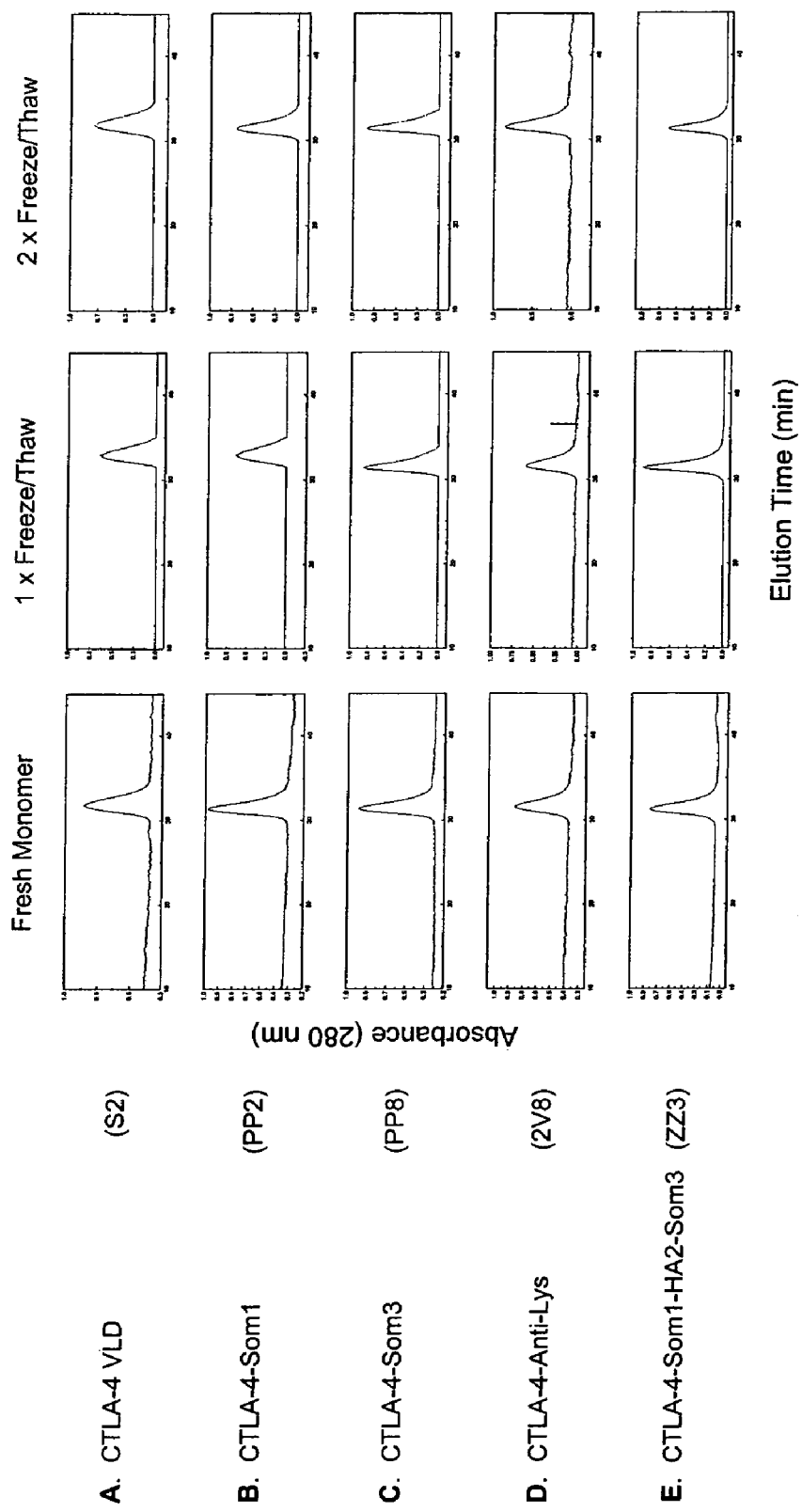
Figure 9: Size exclusion HPLC analysis of affinity purified CTLA-4 VLD STMs: Effect of Freeze/Thaw upon protein

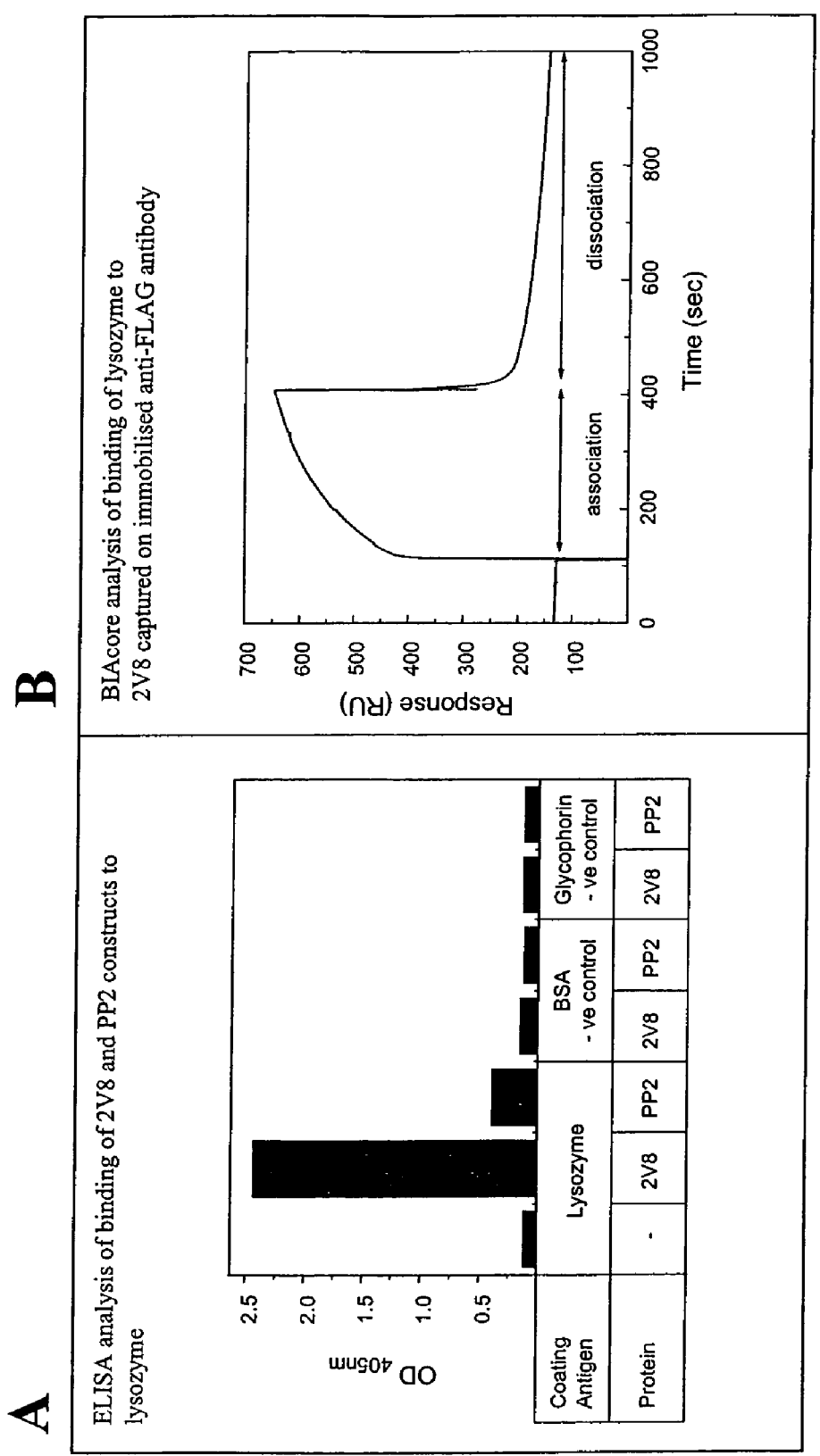
Figure 10: Lysozyme binding characteristics of CTLA-4 anti-lysozyme construct 2V8

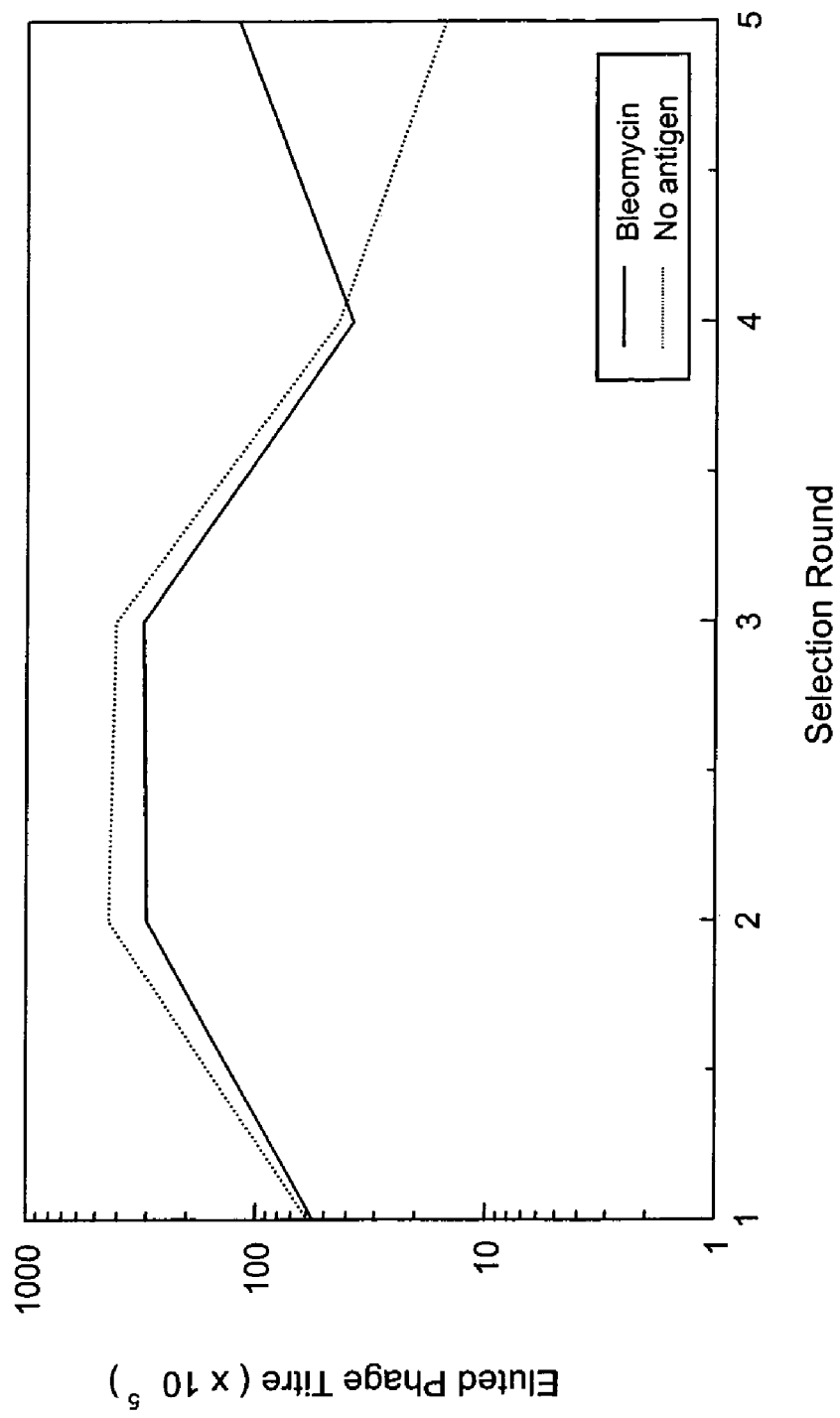
Figure 11: Screening of CTLA-4 VLD Phagemid Library on Immobilised Sh Bleomycin

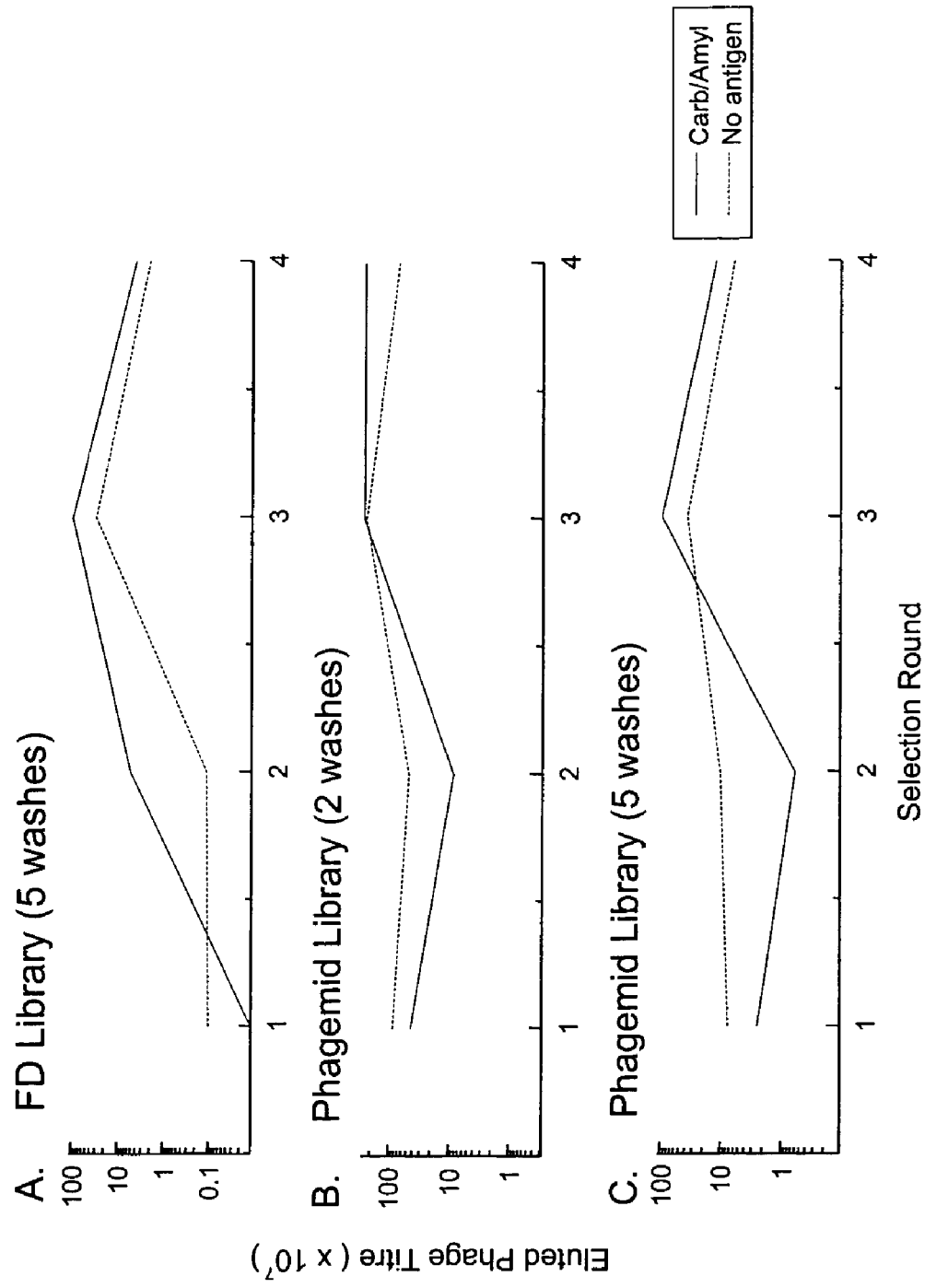
Figure 12: Screening of CTLA-4 VLD libraries in solution.

V-LIKE DOMAIN BINDING MOLECULES

RELATED APPLICATIONS

This application is the National Phase of PCT/AU99/00136, filed Mar. 5, 1999, designating the U.S. and published as WO 99/45110, with a claim of priority from Australian application no. PP2210, filed Mar. 6, 1998. All of the foregoing applications, as well as all documents cited in the foregoing applications ("application documents") and all documents cited or referenced in application documents are hereby incorporated herein by reference. Also, all documents cited in this application ("herein cited documents") and all documents cited or referenced in herein cited documents are hereby incorporated herein by reference.

FIELD OF THE INVENTION

The present invention relates to V-like Domain binding molecules with affinities for target molecules. The present invention also relates to compositions comprising these V-like domain bindng molecules and to methods of diagnosis or treatment which involve the use of these molecules. The present invention also relates to a method for selecting V-like Domain binding molecules with novel binding affinities and/or specificities.

BACKGROUND OF THE INVENTION

Immunoglobulin Superfamily—Antibody Variable (V) Domains

Antibodies are the paradigm of specific high-affinity binding reagents and provide an antigen binding site by interaction of variable heavy ($V_H$) and variable light ($V_L$) immunoglobulin domains. The binding interface is formed by six surface polypeptide loops, termed complimentarity determining regions (CDRs), three from each variable domain, which are highly variable and combined provide a sufficiently large surface area for interaction with antigen. Specific binding reagents can be formed by association of only the $V_H$ and $V_L$ domains into an Fv module. Bacterial expression is enhanced by joining the V-domains with a linker polypeptide into a single-chain scFv molecule. "Humanisation" of a recombinant antibodies by grafting murine CDR loop structures onto a human Fv framework is disclosed by Winter et al EP-239400.

Methods to improve the expression and folding characteristics of single-chain Fv molecules were described by Nieba et al (1997). The properties of single V-domains, derived from natural mammalian antibodies, have been described by Gussow et al in WO/90/05144 and EP 0368684B1 and by Davis et al in WO/91/08482. Single camelid V-domains have been described by Hamers et al in WO/96/34103 and in WO/94/25591. A method for reducing the hydrophobicity of the surface of a human $V_H$ domain by replacing human amino acid sequences with camelid amino acid sequences wad described by Davies and Riechmann (1994). Methods to exchange other regions of human $V_H$ sequences with camel sequences to further enhance protein stability, including the insertion of cysteine residues in CDR loops, were described by Davies and Riechmann (1996).

Several attempts to engineer high-affinity single domain binding reagents using either the $V_H$ or $V_L$ domains alone have been unsuccessful, due to lack of binding specificity and the inherent insolubility of single domains in the absence of the hydrophobic face where the $V_H$ and $V_L$ domains interact (Kortt et al, 1995).

T-CELL RECEPTOR VARIABLE (V) DOMAINS

The T-cell receptor has two V-domains that combine into a structure similar to the Fv module of an antibody that results from combination of the VH and VL domains. Novotny et al (1991) described how the two V-domains of the T-cell receptor (termed alpha and beta) can be fused and expressed as a single chain polypeptide and, further, how to alter surface residues to reduce the hydrophobicity directly analogous to an antibody scFv. Other publications describe the expression characteristics of single-chain T-cell receptors comprising two V-alpha and V-beta domains (Wulfing and Pluckthun, 1994; Ward, 1991).

NON-ANTIBODY LIGANDS—CTLA-4 AND CD28 V-LIKE DOMAINS

There are a class of non-antibody ligands which bind to specific binding partners which also comprise V-like domains. These V-like domains are distinguished from those of antibodies or T-cell receptors because they have no propensity to join together into Fv-type molecules. These non-antibody ligands provide an alternative framework for the development of novel binding moieties with high affinities for target molecules. Single domain V-like binding molecules derived from these non-antibody ligands which are soluble are therefore desirable. Examples of suitable non-antibody ligands are CTLA-4, and CD28 and ICOS (Hutloff et al, 1999).

Cytotoxic T-lymphocyte associated antigen 4 (CTLA-4) and the homologous cell-surface proteins CD28 and ICOS, are involved in T-cell regulation during the immune response. CTLA-4 is 44 kDa homodimer expressed primarily and transiently on the surface of activated T-cells, where it interacts with CD80 and CD86 surface antigens on antigen presenting cells to effect regulation of the immune response (Waterhouse et al. 1996, van der Merwe et al. 1997). CD28 is a 44 kDa homodimer expressed predominantly on T-cells and, like CTLA-4, interacts with CD80 and CD86 surface antigens on antigen presenting cells to effect regulation of the immune response (Linsley et al.1990). Current theory suggests that competition between CTLA-4 and CD28 for available ligands controls the level of immune response, for example, gene deletion of CTLA-4 in knock-out mice results in a massive over-proliferation of activated T-cells (Waterhouse et al. 1995).

Each CTLA-4 monomeric subunit consists of an N-terminal extracellular domain, transmembrane region and C-terminal intracellular domain. The extracellular domain comprises an N-terminal V-like domain (VLD; of approximately 14 kDa predicted molecular weight by homology to the immunoglobulin superfamily) and a stalk of about 10 residues connecting the VLD to the transmembrane region. The VLD comprises surface loops corresponding to CDR-1, CDR-2 and CDR-3 of an antibody V-domain (Metzler 1997). Recent structural and mutational studies on CTLA-4 suggest that binding to CD80 and CD86 occurs via the VLD surface formed from a A'GFCC'(SEQ ID NO:139) V-like beta-strands and also from the highly conserved MYPPPY (SEQ ID NO:1) sequence in the CDR3-like surface loop (Peach et al. 1994; Morton et al. 1996; Metzler et al. 1997). Dimerisation between CTLA-4 monomoers occurs through a disulphide bond between cysteine residues ($Cys^{120}$) in the two stalks, which results in tethering of the two extracellular domains, but without any apparent direct association between V-like domains (Metzler et al. 1997). Dimerisation appears to contribute exclusively to increased avidity for the ligands.

IN-VITRO EXPRESSION OF SOLUBLE FORMS OF CTLA-4

Neither the extracellular domains nor V-like domains (VLDs) of human CTLA-4 molecule have been successfully expressed as soluble monomers in bacterial cells, presumably due to aggregation of the expressed proteins (Linsley et al, 1995). Expression of the extracellular N-terminal domain ($Met^1$ to $Asp^{124}$, comprising $Cys^{120}$) in *E. coli* results in production of a dimeric 28 kDa MW protein, in which two CTLA-4 V-like domains are joined by a disulphide linkage at $Cys^{120}$. Truncation at $Val^{114}$ removes these cysteines and was intended to enable expression of a 14 kDa VLD in soluble, monomeric form. However, the product aggregated and it was concluded that hydrophobic sites, which were normally masked by glycosylation, were now exposed and caused aggregation (Linsley et al, 1995).

There have been some reports of successful expression of monomeric, glycosylated CTLA-4 extracellular domains in eukaryotic expression systems (ie CHO cells and the yeast Pichia pastoris; Linsley et al. 1995; Metzler et al. 1997; Gerstmayer et al. 1997). Glycosylation in these eukaryotic expression systems is presumed to occur at the two N-linked glycosylation sites in the VLD (Asn76 and Asn108). However, high yields have only been described for expression of a gene encoding a CTLA-4 VLD fused to Ig—CH2/CH3 domains which produces a dimeric recombinant protein with 2 CTLA-4 VLDs attached to an Fc subunit (WO 95/01994 and AU 16458/95). AU 60590/96 describes mutated forms of CTLA-4 VLDs with single amino acid replacements of the first tyrosine (Y) in the MYPPPY (SEQ ID NO: 1) surface loop which retain and modifies the affinity for the natural CD80 and CD86 ligands. AU 60590/96 describes the preferred soluble form of CTLA-4 VLDs as a recombinant CTLA-4/Ig fusion protein expressed in eukaryotic cells and does not solve the aggregation problem in prokaryote expression systems. EP 0757099A2 describes the use of CTLA-4 mutant molecules, for example the effect of changes on ligand binding of mutations in the CDR3-like loop.

SUMMARY OF THE INVENTION

The present inventors have now developed novel binding molecules derived from the V-like domains (VLDs) of non-antibody ligands such as CTLA-4, CD28 and ICOS. Replacement of CDR loop structures within the VLDs results unexpectedly in the production of monomeric, correctly folded molecules with altered binding specificities and improved solubility.

Accordingly, in a first aspect the present invention provides a binding moiety comprising at least one monomeric V-like domain (VLD) derived from a non-antibody ligand, the at least one monomeric V-like domain being characterized in that at least one CDR loop structure or part thereof is modified or replaced such that the solubility of the modified VLD is improved when compared with the unmodified VLD.

Within the context of the present invention, the modification or replacement may involve any change to one or more physical characteristics (such as size, shape, charge, hydrophobicity etc) of the at least one CDR loop structure. The modification or replacement may result in a reduction in the size of the at least one CDR loop structure. In a preferred embodiment, however, at least one CDR loop structure or part thereof is modified or replaced such that (i) the size of the CDR loop structure is increased when compared with corresponding CDR loop structure in the unmodified VLD; and/or (ii) the modification or replacement results in the formation of a disulphide bond within or between one or more of the CDR loop structures.

In a second aspect, the present invention provides a binding moiety comprising at least one monomeric V-like domain (VLD) derived from a non-antibody ligand, the at least one monomeric V-like domain being characterized in that at least one CDR loop structure or part thereof is modified or replaced such that (i) the size of the CDR loop structure is altered when compared with corresponding CDR loop structure in the unmodified VLD; and/or (ii) the modification or replacement results in the formation of a disulphide bond within or between one or more of the CDR loop structures.

In a preferred embodiment of the second aspect, the size of the CDR loop structure is increased by at least two, more preferably at least three, more preferably at least six and more preferably at least nine amino acid residues.

In a further preferred embodiment, the modified binding moiety of the first or second aspect of the present invention also exhibits an altered binding affinity or specificity when compared with the unmodified binding moiety. Preferably, the effect of replacing or modifying the CDR loop structure is to reduce or abolish the affinity of the VLD to one or more natural ligands of the unmodified VLD. Preferably, the effect of replacing or modifying the CDR loop structure is also to change the binding specificity of the VLD. Thus it is preferred that the modified VLD binds to a specific binding partner which is different to that of the unmodified VLD.

The phrase "V-like domain" or "VLD" is intended to refer to a domain which has similar structural features to the variable heavy ($V_H$) or variable light ($V_L$) antibody. These similar structural features include CDR loop structures. By "CDR loop structures" we mean surface polypeptide loop structures or regions like the complimentarity determining regions in antibody V-domains.

The phrase "non-antibody ligand" is intended to refer to any ligand which binds to a specific binding partner and which is not an antibody or a T-cell receptor. Examples of suitable non-antibody ligands are T-cell surface proteins such as CTLA-4, CD28 and ICOS. It will be appreciated by those skilled in the art that other non-antibody ligands which may provide V-like domains suitable for the invention are other T-cell surface proteins such as CD2, CD4, CD7 and CD16; B cell surface proteins such as CD19, CD79a, CD22, CD33, CD80 and CD86; adhesion molecules such as CD48, CD541CAM and CD58. These molecules, which are listed in Table 1, provide a non-exhaustive list of structures which may form the basis for the single domain binding molecules of the present invention.

The phrase "V-like domain derived from a non-antibody ligand" is intended to encompass chimeric V-like domains which comprise at least part of a V-like domain derived from a non-antibody ligand.

TABLE 1

NON-ANTIBODY LIGANDS

| Molecule | Size | Structure |
|---|---|---|
| T cell Surface Proteins | | |
| CD2 | 45–58 kDa | VC[1] domains |
| CD4 | 55 kDa | V2C2 |
| CD7 | 40 kDa | V domain |
| CD16 | 50–65 kDa | 2xC domains |
| B cell Surface Proteins | | |
| CD19 | 95 kDa | 2xC domains |
| CD79a | 33 kDa | |
| CD22 | 130–140 kDa | 1xV 6xC domains |
| CD33 | 67 kDa | VC domain |
| CD80 | 60 kDa | VC domain |
| CD86 | 60 kDa | VC domain |
| Adhesion molecules | | |
| CD48 | 45 kDa | VC domain |
| CD54ICAM | 85–110 kDa | |
| CD58 | 55–70 kDa | VC domain |

[1]V = variable 1 g domain, C = constant domain

These molecules are discussed in (1) The Leucocyte Antigen Facts Book. 1993, Eds Barclay et al., Academic Press, London; and (2) CD Antigens 1996 (1997) Immunology Today 18, 100–101, the entire contents of which are incorporated herein by reference.

The "solubility" of modified binding moieties of the present invention correlates with the production of correctly folded, monomeric domains. The solubility of the modified VLDs may therefore be assesed by HPLC. For example, soluble (monomeric) VLDs will give rise to a single peak on the HPLC chromatograph, whereas insoluble (eg. multimeric and aggregated) VLDs will give rise to a plurality of peaks. A person skilled in the art will therefore be able to detect an increase in solubility of modified VLDs using routine HPLC techniques.

It will be appreciated that the binding moieties of the present invention may be coupled together, either chemically or genetically, to form multivalent or multifunctional reagents. For example, the addition of C-terminal tails, such as in the native CTLA-4 with $Cys^{120}$, will result in a dimer.

The binding moieties of the present invention may also be coupled to other molecules for various diagnostic formulations. For example, the VLDs may comprise a C-terminal polypeptide tail or may be coupled to streptavidin or biotin for multi-site in vitro assays. The VLDs may also be coupled to radioisotopes, dye markers or other imaging reagents for in vivo detection and/or localisation of cancers, blood clots, etc. The VLDs may also be immobilised by coupling onto insoluble devices and platforms for diagnostic and biosensor applications.

In a most preferred embodiment of the first aspect of the present invention, the V-like domain is derived from the extracellular domain of the CTLA-4 molecule or the CD28 molecule. In a further preferred embodiment one or more surface loops of the CTLA-4 V-like domain and preferably the CDR-1, CDR-2 or CDR-3 loop structures are replaced with a polypeptide which has a binding affinity for a target molecule of interest. Target molecules of interest comprise, but are not limited to, drugs, steroids, pesticides, antigens, growth factors, tumour markers, cell surface proteins or viral coat proteins. It will be appreciated that these VLDs may be polyspecific, having affinities directed by both their natural surfaces and modified polypeptide loops.

In a further preferred embodiment the effect of replacing or modifying the CTLA-4, CD28 and ICOS V-like domain surface loops is to abolish the natural affinity to CD80 and CD86.

In one preferred embodiment, one or more of the CDR loop structures of the VLD are replaced with one or more CDR loop structures derived from an antibody. The antibody may be derived from any species. In a preferred embodiment, the antibody is derived from a human, rat, mouse, camel, llama or shark. The antibody or antibodies may be selected from the camel antibody cAB-Lys3 and the human anti-melanoma antibody V86.

In a further preferred embodiment, one or more of the CDR loop structures are replaced with a binding determinant derived from a non-antibody polypeptide. For example, one or more of the CDR loop structures may be replaced with a polypeptide hormone, such as somatostatin which is a 14 residue intra-disulphide bonded polypeptide important in cancer cell recognition, or with a viral protein such as the human influenza virus haemagglutinin protein.

In a further preferred embodiment the V-like domain of the binding moiety comprises CDR loop structures homologous in character to CDR loop structures found in camelid or llama antibodies. For example, the CDR loop structures may contain one or more non-conventional substitutions (eg. hydrophobic to polar in nature). In another preferred embodiment, the CDR-1 and CDR-3 loop structures may adopt non-canonical conformations which are extremely heterologous in length. The V-like domain may also possess a disulphide linkage interconnecting the CDR-1 and CDR-3 loop structures (as found in some camel $V_HH$ antibodies) or the CDR-2 and CDR-3 loop structures (as found in some llama $V_HH$ antibodies).

In a third aspect the present invention provides a polynucleotide encoding a binding moiety of the first or second aspect of the present invention. The polynucleotide may be incorporated into a plasmid or expression vector.

In a fourth aspect the present invention provides a prokaryotic or eukaryotic host cell transformed with a polynucleotide according to the third aspect of the present invention.

In a fifth aspect the present invention provides a method of producing a binding moiety which comprises culturing a host cell according to the fourth aspect of the present invention under conditions enabling expression of the binding moiety and optionally recovering the binding moiety.

In a preferred embodiment of the present invention the binding moiety is produced by expression in a bacterial host. Preferably, the binding moiety is unglycosylated.

In a sixth aspect the present invention provides a pharmaceutical composition comprising a binding moiety of the first or second aspect of the present invention and a pharmaceutically acceptable carrier or diluent.

In a seventh aspect the present invention provides a method of treating a pathological condition in a subject, which method comprises administering to the subject a binding moiety according to the first or second aspect of the present invention.

For in vivo applications it is preferable that VLDs are homologous to the subject of treatment or diagnosis and that any possible xenoantigens are removed. Accordingly it is preferred that VLD molecules for use in clinical applications are substantially homologous to naturally occurring human immunoglobulin superfamily members.

In an eighth aspect the present invention provides a method of selecting a binding moiety with an affinity for a target molecule which comprises screening a library of polynucleotides for expression of a binding moiety with an affinity for the target molecule, the polynucleotides encoding VLDs derived from one or more non-antibody ligands, wherein the polynucleotides have been subjected to mutagenesis which results in a modification or replacement in at least one CDR loop structure in at least one VLD and wherein the solubility of the isolated modified VLD is improved when compared with the isolated unmodified VLD.

It will be appreciated by those skilled in the art that within the context of the eighth aspect of the present invention, any method of random or targetted mutagenesis may be used to introduce modifications into the V-like domains. In a preferred embodiment, the mutagenesis is targetted mutagenesis. Preferably, the targetted mutagenesis involves replacement of at least one sequence within at least one CDR loop structure using splice overlap PCR technology.

It will also be appreciated by those skilled in the art that the polynucleotide library may contain sequences which encode VLDs comprising CDR loop structures which are substantially identical to CDR loop structures found in naturally occurring immunoglobulins as well as sequences which encode VLDs comprising non-naturally occurring CDR loop structures.

In a preferred embodiment of the eighth aspect of the present invention, the screening process involves displaying the modified V-like domains as gene III protein fusions on the surface of bacteriophage particles. The library may comprise bacteriophage vectors such as pHFA, fd-tet-dog or pFAB.5c containing the polynucleotides encoding the V-like domains.

In a further preferred embodiment of the eighth aspect, the screening process involves displaying the modified V-like domains in a ribosomal display selection system.

Throughout this specification, the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF THE DRAWINGS

FIGS. 1A–F show CTLA-4 VLD-Specific Oligonucletides (SEQ ID NO: 2–56).

FIGS. 2A and 2B show the polynucleotide sequence of complete cDNA encoding human CTLA-4 (2A) and polypeptide sequence of the VLD of human CTLA-4 (2B).

FIG. 3 shows the phage display of CTLA-4 VLD STMs as gene 3 fusions on the surface of phage or phagemid. CTLA-4 VLD STMs are depicted as black spheroids; gene 3 protein is depicted as white spheroids; FLAG polypeptide is depicted in grey; genes are marked in a similar colour code and are depicted in an oval phage(mid) vector.

FIG. 4 shows a schematic representation of the somatostatin polypeptide. Somatostatin (somatotropin release-inhibiting factor SRIF) in a cyclic 14-amino acid polypeptide. The cyclic nature is provided by a disulphide linkage between the cysteine residues at positions 3 and 14. The four residues which constitute the tip of the loop (Phe—Trp—Lys—Thr) (SEQ ID NO: 140) are implicated in binding to members of the somatostatin receptor family.

FIG. 5 shows the size exclusion HPLC profiles of affinity purified CTLA-4 VLD and CTLA-4-Som3 STM. Recombinant human CTLA-4 proteins were expressed in *E. coli* host TG1 from vector pGC, purified from periplasmic extracts by anti-FLAG affinity chromatography and subjected to size exclusion chromatography on a calibrated Superose 12 HR column. The elution profiles of purified CTLA-4 VLD and CTLA-4 STM are overlayed in this graph. CTLA-4 VLD comprises tetramer (21.86 min), dimer (26.83) and monomer (29.35 min). CTLA-4-Som3 STM comprises dimer (26.34) and monomer (29.28). Traces represent absorbance at 214 nm and are given in arbitrary units.

FIGS. 7A–I show HPLC profiles of purified recombinant human CTLA-4 STMs. Recombinant CTLA-4 VLDs were expressed in *E. coli* host TG1 from vector pGC, purified from periplasmic extracts by anti-FLAG affinity chromatography and subjected to size exclusion chromatography on a calibrated Superose 12 HR column. The elution profiles of the purified proteins are shown. 7A shows CTLA-4 DIMER (PP5); 7B shows CTLA-4R (S2); 7C shows CTLA-4-HA2 (XX4); 7D shows CTLA-4-Som3 (PP8); 7E shows CTLA-4-Som1 (PP2); 7F shows CTLA-4-Som1-Som3 (VV3); 7G shows CTLA-4-Som-HA2-Som3 (ZZ3); 7H shows CTLA-4-anti-lys (2V8); 7I shows CTLA-4-anti-mel (3E4).). Traces represent absorbance at 214 nm and are given in arbitrary units.

FIGS. 8A–E show a comparison by size exclusion FPLC analysis of affinity purified CTLA-4 constructs synthesized using bacterial expression vector pGC or pPOW. Recombinant human CTLA-4R or its loop variants where expressed in *E. coli* host TOP10F', purified from periplasmic extracts by anti-FLAG affinity chromatography and subjected to size exclusion chromatography on a calibrated Superose 12HR column. The elution profiles of proteins expressed from vector pGC are shown on the left, whilst proteins expressed from vector pPOW are shown on the right. 8A shows wild-type CTLA-4 (S2); 8B shows CTLA-4-Som1 (PP2); 8C shows CTLA-4-Som3(PP8); 8D shows CTLA-4-Anti-lys(2V8); 8E shows CTLA-4-Som1-HA2-Som3(ZZ3).

FIGS. 9A–E show protein stability analysis. Stability of monomer preparations of CTLA-4 VLD and loop variant constructs was analysed by size exclusion fplc chromatography on a precalibrated superose 12 hr (Pharmacia) column following several cycles of freeze/thawing. Aliquots of each protein were tested immediately after peak purification and following two cycles of freeze/thawing. 9A shows CTLA-4 VLD (S2); 9B shows CTLA-4-Som1 (PP2); 9C shows CTLA-4-Som3 (PP8); 9D shows CTLA-4-anti-lys (2V8); 9E shows CTLA-4-Som-HA2-Som3 (ZZ3).

FIGS. 10A–B show the lysozyme binding characteristics of CTLA-4-anti-lys construct 2V8. 10A shows ELISA analysis; 10B shows BIAcore analysis.

FIG. 11 shows screening of CTLA-4 VLD phagemid library on immobilised Sh bleomycin.

FIGS. 12A–C show screening of CTLA-4 VLD libraries in solution. 12A shows an FD library (5 washes); 12B shows a phagemid library (2 washes); and 12C shows a phagemid library (5 washes).

DETAILED DESCRIPTION OF THE INVENTION

The present invention relates to the design of novel soluble VLD binding molecules derived from the V-like domain of immunoglobulin superfamily members, such as the human CTLA-4 molecule. The preferred binding molecules of the present invention provide the following advantages (i) use of a native human protein obviates the need for subsequent humanisation of the recombinant molecule, a step often required to protect against immune system response if used in human treatment; (ii) the domain is naturally monomeric as described above (incorporation of residue Cys120 in a C-terminal tail results in production of a dimeric molecule); and (iii) structural modifications have resulted in improved E. coli expression levels.

Prior to publication of the first CTLA-4 structure determination, available sequence data and mutational analyses of both this molecule and CD28 were analysed. This allowed modelling and prediction of the regions corresponding to antibody CDR1, 2 and 3 regions. It was hypothesised that such areas would be susceptible to mutation or substitution without substantial effect upon the molecular framework and hence would allow expression of a correctly folded molecule. The subsequently published structure (Metzler et al. 1997) showed these predictions to be accurate, despite the unexpected separation of CDR1 from the ligand-binding site, and the extensive bending of CDR3 to form a planar surface contiguous with the ligand binding face.

In an initial set of experiments the V-like domain of the human CTLA-4 molecule was modified by replacement of CDR loop structures with either of two defined polypeptides. The two polypeptides were human somatostatin (Som) and a portion of the human influenza virus haemagglutinin protein (HA-tag). Somatostatin (SRIF: somatotropin release-inhibiting factor) is a 14 residue polypeptide comprising a disulphide bond that forces the central 10 residues into a loop. Human somatostatin is biologically widespread within the body and mediates a number of diverse physiological functions such as regulation of growth hormone secretion etc (Reisne, 1995). Human somatostatin binds a number of specific receptors (there are at least five subtypes) which have differing tissue specificities and affinities (Schonbrunn et al. 1995). These aspects of binding and activation are as yet poorly understood, but one salient feature is the high density of somatostatin receptors present on a number of cancerous cell lines, for example cancers of the neuro-endocrine system and small lung cancers (Reubi 1997). Artificial analogues of somatostatin have been produced for imaging of such tumours which are resistant to degradation compared with the highly labile somatostatin polypeptide.

The haemagglutinin epitope sequence consists of the 9 residues YPYDVPDYA (SEQ ID NO: 63). A commercially produced antibody is available which specifically recognises this sequence. The epitope tag can be detected when randomly or directionally incorporated within the structure of proteins (Canfield et al. 1996).

Replacement of one or more CDR loop structures in the CTLA-4 V-like domain with somatostatin or the HA-tag resulted in the production of soluble, monomeric, unglycosylated binding molecules using different bacterial expression systems. This surprising finding shows that V-like domains provide a basic framework for constructing soluble, single domain molecules, where the binding specificity of the molecule may be engineered by modifications of the CDR loop structures.

The basic framework residues of the V-like domain may be modified in accordance with structural features present in camelid antibodies. The camel heavy chain immunoglobulins differ from "conventional" antibody structures by consisting of only a single VH domain (Hamers-Casterman et al. 1993). Several unique features allow these antibodies to overcome the dual problems of solubility and inability to present a sufficiently large antigen binding surface.

First, several non-conventional substitutions (predominantly hydrophobic to polar in nature) at exposed framework residues reduce the hydrophobic surface, while maintaining the internal beta-sheet framework structure (Desmyter et al. 1996). Further, within the three CDR loops several structural features compensate for the loss of antigen binding-surface usually provided by the VL domain. While the CDR2 loop does not differ extensively from other VH domains, the CDR-1 and -3 loops adopt non-canonical conformations which are extremely heterologous in length. For example, the H1 loop may contain anywhere between 2–8 residues compared to the usual five in Ig molecules. However, it is the CDR3 loop which exhibits greatest variation: in 17 camel antibody sequences reported, the length of this region varies between 7 and 21 residues (Muyldermans et al. 1994). Thirdly, many camelid VH domains possess a disulphide linkage interconnecting CDRs-1 and -3 in the case of camels and interconnecting CDRs-1 and -2 in the case of llamas (Vu et al. 1997). The function of this structural feature appears to be maintenance of loop stability and providing a more contoured, as distinct from planar, loop conformation which both allows binding to pockets within the antigen and gives an increased surface area. However, not all camelid antibodies possess this disulphide bond suggesting that it is not an absolute structural requirement.

These foregoing features have enabled camelid V-domains to present as soluble molecules in vivo and with sufficiently high affinity to form an effective immune response against a wide variety of target antigens. In contrast, cell surface receptors of the Ig superfamily (such as CD4 and CD2) comprise V-like binding domains and appear to bind cognate receptors with surface features other than the CDR loops. These V-like domains bind to cognate receptors with very low affinity. Physiological signalling between two cells are mediated by the avidity of multi-point binding, when two cell surfaces connect and each contains multiple receptors. CD2 is a well-characterised example: binding to CD58 is mediated by a highly constrained set of minor electrostatic interactions generated by charged and polar residues located in the GFCC'C"(SEQ ID NO: 141) face (not the antibody type CDR-1, CDR-2 or CDR-3 loops). This results in a low affinity but highly specific interaction (Bodian et al 1994).

The present invention also relates to a method for generating and selecting single VLD molecules with novel binding affinities for target molecules. This method involves the application of well known molecular evolution techniques to V-like domains derived from members of the immunoglobulin superfamily. The method may involve the production of phage or ribosomal display libraries for screening large numbers of mutated V-like domains.

Filamentous fd-bacteriophage genomes are engineered such that the phage display, on their surface, proteins such as the Ig-like proteins (scFv, Fabs) which are encoded by the DNA that is contained within the phage (Smith, 1985; Huse et al., 1989; McCafferty et al., 1990; Hoogenboom et al., 1991). Protein molecules can be displayed on the surface of Fd bacteriophage, covalently coupled to phage coat proteins encoded by gene III, or less commonly gene VIII. Insertion of antibody genes into the gene III coat protein give expression of 3–5 recombinant protein molecules per phage, situated at the ends. In contrast, insertion of antibody genes into gene VIII has the potential to display about 2000 copies of the recombinant protein per phage particle, however this is a multivalent system which could mask the affinity of a single displayed protein. Fd phagemid vectors are also used, since they can be easily switched from the display of functional Ig-like fragments on the surface of Fd-bacteriophage to secreting soluble Ig-like fragments in *E. coli*. Phage-displayed recombinant protein fusions with the N-terminus of the gene III coat protein are made possible by an amber codon strategically positioned between the two protein genes. In amber suppressor strains of E. coli, the resulting Ig domain-gene III fusions become anchored in the phage coat.

A selection process based on protein affinity can be applied to any high-affinity binding reagents such as antibodies, antigens, receptors and ligands (see, for example, Winter and Milstein, 1991, the entire contents of which are incorporated herein by reference). Thus the selection of the highest affinity binding protein displayed on bacteriophage is coupled to the recovery of the gene encoding that protein. Ig-displaying phage can be affinity selected by binding to cognate binding partners covalently coupled to beads or adsorbed to plastic surfaces in a manner similar to ELISA or solid phase radioimmunoassays. While almost any plastic surface will adsorb protein antigens, some commercial products are especially formulated for this purpose, such as Nunc Immunotubes.

Ribosomal display libraries involve polypeptides synthesized de novo in cell-free translation systems and displayed on the surface of ribosomes for selection purposes (Hanes and Pluckthun, 1997; He and Taussig, 1997). The "cell-free translation system" comprises ribosomes, soluble enzymes required for protein synthesis (usually from the same cell as the ribosomes), transfer RNAs, adenosine triphosphate, guanosine triphosphate, a ribonucleoside triphosphate regenerating system (such as phosphoenol pyruvate and pyruvate kinase), and the salts and buffer required to synthesize a protein encoded by an exogenous mRNA. The translation of polypeptides can be made to occur under conditions which maintain intact polysomes, i.e. where ribosomes, mRNA molecule and translated polypeptides are associated in a single complex. This effectively leads to "ribosome display" of the translated polypeptide.

For selection, the translated polypeptides, in association with the corresponding ribosome complex, are mixed with a target molecule which is bound to a matrix (e.g. Dynabeads). The target molecule may be any compound of interest (or a portion thereof) such as a DNA molecule, a protein, a receptor, a cell surface molecule, a metabolite, an antibody, a hormone or a virus. The ribosomes displaying the translated polypeptides will bind the target molecule and these complexes can be selected and the mRNA re-amplified using RT-PCR.

Although there are several alternative approaches to modify binding molecules the general approach for all displayed proteins conforms to a pattern in which individual binding reagents are selected from display libraries by affinity to their cognate receptor. The genes encoding these reagents are modified by any one or combination of a number of in vivo and in vitro mutation strategies and constructed as a new gene pool for display and selection of the highest affinity binding molecules.

In order that the nature of the present invention may be more clearly understood preferred forms thereof will now be described with reference to the following examples.

EXAMPLE 1

Gene Construction and Cloning

CTLA-4 STM (STM: soluble truncated mutants of CLTA-4, used herein to describe CTLA-4 chimaeric V-like domain proteins) gene construction and cloning was by standard and well-described techniques (Polymerase chain reaction with specifically designed oligonucleotide primers, splice overlap extension, restriction enzyme digests etc). A list of oligonucleotide primers used is given in FIG. 1.

The wild-type STM construct was amplified from cloned human CTLA-4 DNA (FIG. 2) (and could be similarly amplified from reverse transcribed human cDNA by a competent worker in the field) using the oligonucleotide primers #3553 and #4316, which incorporated SfiI and NotI restriction sites at the 5' and 3' ends respectively. These terminal primers were used in all further constructions except: (i) where #4851 or #5443 was used to incorporate an ApaL1 site at the 5' end; (ii) where #4486 was used to add a C-terminal tail including residue Cys120; (iii) where #5467 was used to incorporated an EcoR1 site at the 5' end; and (iv) where the specific set of extension primers were used for ribosomal display.

A splice overlap PCR strategy using combinations of the oligonucleotides primers listed in FIG. 1 was used to produce variations of CDR-1, CDR-2 and/or CDR-3 loop structure replacements. The variations, which are described in greater detail in the following examples are listed to Table 2.

TABLE 2

| | CDR-1 combinations | |
|---|---|---|
| | CDR-1 | |
| CTLA-4 VLD (SEQ ID no: 71) | S$^{19}$FVCEYA.SPGKATE............ | VRV... |
| Anti-lysozyine (SEQ ID no: 72) | S$^{19}$FVCEYA.SGYTIGPYCMG.......... | VRV... |
| Somatostatin-14 (SEQ ID no: 73) | S$^{19}$FVCEYA.AGCKNFFWKTFTSCATE. | VRV... |
| Anti-melanoma (SEQ ID no: 74) | S$^{19}$FVCEYA.SGFTFSSYAMS......... | VRV... |
| Randomization 1 (SEQ ID no: 75) | S$^{19}$FVCEYA.XXXXXXXG............ | VRV... |
| Randomization 2 (SEQ ID no: 76) | S$^{19}$FVCEYA.XXXXXXXXCXG.......... | VRV... |
| Randomization 3 (SEQ ID no: 77) | S$^{19}$FVCEYA.XXnrXarXXarCXG....... | VRV... |
| Randomization 4 (SEQ ID no: 78) | S$^{19}$FVCEYA.SPGXXXX.............. | VRV... |
| Randomization 5 (SEQ ID no: 79) | S$^{19}$FVCEYA.SPGXCXX.............. | VRV... |
| Randomization 6 (SEQ ID no: 80) | S$^{19}$FVCEYA.XXXXXXXXXATE.......... | VRV... |
| Randomization 7 (SEQ ID no: 81) | S$^{19}$FVCEYA.XXXXXXCXATE.......... | VRV... |
| Randomization 8 (SEQ ID no: 82) | S$^{19}$FVCEYA.AGCKNXXXXXXXTSCATE. | VRV... |

TABLE 2-continued

CDR-2 combinations

CDR-2

| | |
|---|---|
| CTLA-4 VLD (SEQ ID no: 83) | $Q^{44}$VTEVCAA.TYMMGNELTF.LDDSICT... |
| Anti-lysozyme (SEQ ID no: 84) | $Q^{44}$VTEVCAA.AINMGGGITF.LDDSICT... |
| Haemagglutinin tag (SEQ ID no: 85) | $Q^{44}$VTEVCAA.TYPYDVPDYA.LDDSICT... |
| Anti-melanoma | $Q^{44}$VTEVCAA.AISGSGGSTY.LDDSICT... |
| Randomization 1 (SEQ ID no: 87) | $Q^{44}$VTEVCAA.TYXXGXELTF.LDDSICT... |
| Randomization 2 (SEQ ID no: 88) | $Q^{44}$VTEVCAA.CYXXGXELTF.LDDSICT... |

CDR-3 combinations

CDR-3

| | | |
|---|---|---|
| CTLA-4 VLD (SEQ ID no: 89) | $C^{93}$KV.ELMYPPPYYL............... | GIG... |
| Anti-lysozyme (SEQ ID no: 90) | $C^{93}$KV.DSTIYASYYE<u>C</u>GHGLSTGGYGYDS. | GIG... |
| Somatostatin-14 (SEQ ID no: 91) | $C^{93}$KV.EAG<u>C</u>KNFFWKTFTS<u>C</u>.......... | GIG... |
| Anti-melanoma (SEQ ID no: 92) | $C^{93}$KV.GWGLRGEEGDYYMDV.......... | GIG... |
| Randomization 1 (SEQ ID no: 93) | $C^{93}$KV.XXXXXXXXXXXX............. | GIG... |
| Randomization 2 (SEQ ID no: 94) | $C^{93}$KV.XXXXXXXXXXXXXXXX.......... | GIG... |
| Randomization 3 (SEQ ID no: 95) | $C^{93}$KV.XXXXXX.C.XXXX............ | GIG... |
| Randomization 4 (SEQ ID no: 96) | $C^{93}$KV.XXXXXXXX.C.XXXX........... | GIG... |
| Randomization 5 (SEQ ID no: 97) | $C^{93}$KV.XXXXXXXXX.C.XXXXX......... | GIG... |
| Randomization 6 (SEQ ID no: 98) | $C^{93}$KV.XXXXXXXXXXX.C.XXXXXXX..... | GIG... |
| Randomization 7 (SEQ ID no: 99) | $C^{93}$KV.EXXXXXXXXX............... | GIG... |
| Randomization 8 (SEQ ID no: 100) | $C^{93}$KV.EXXXXXX.C.XXXXXXX........ | GIG... |
| Randomization 9 (SEQ ID no: 101) | $C^{93}$KV.EAG<u>C</u>KNXXXXXXTS<u>C</u>..... | GIG... |

For generation of randomised sections of the CDR loop structures, similar splice-overlap techniques were used with oligonucleotides where a given triplet(s) were encoded by the sequence NNg/T where N represents any of the four possible nucleotide bases. This combination covers all possible amino acid residues. Alternatively, randomisation was biased towards certain subsets of amino acids (for example aromatic residues, FIG. 1, #5452).

In some instances, a variant technique was used for STM gene construction, where randomised oligonucleotide primers were designed which incorporated restriction sites for direct cloning into the similarly modified (with complementary restriction sites) CTLA-4 VLD framework (for example FIG. 1, #4254).

Completed constructs were cut with appropriate combinations of restriction enzymes (for example Sfi1,Not1, ApaL1, EcoR1) and cloned into like sites in appropriate expression vectors. These vectors comprise: (i) for production of soluble protein expression vectors pGC (Coia et al, 1996) and pPOW (Power et al, 1992; Kortt et al. 1995) (ii) for bacteriophage and phagemid display, completed STM constructs were cut with the restriction enzymes SfiI and NotI or ApaLI and NotI and cloned into the vectors pHFA, and pFAB.5c (phagemid) or pfd-Tet-DOG (phage). These vectors allow display of the STMs as gene3 protein fusions on the surface of bacteriophage in 1–2 (phagemid) or 3–5 (phage) copies per bacteriophage particle (FIG. 3).

All DNA constructs were verified by restriction analysis and DNA sequencing and tested for expression of recombinant protein by standard and well-understood techniques (Polyacrylamide gel electrophoresis, Western blot etc).

EXAMPLE 2

Production and Isolation of Recombinant STM Proteins

Recombinant proteins were produced using vectors which represent different protocols for periplasmic expression systems. These vectors were (i) pGC: this vector allows high level expression of heterologous proteins by chemical (IPTG) induction, which are targeted to the periplasmic space by means of a leader sequence. The leader sequence is subsequently cleaved to produce the mature protein. In addition, this vector contains two in-frame 8 residue tag sequences (FLAG tags) which allow affinity purification of the recombinant protein. (ii) pPOW, which, like pGC, allows high level heat inducible expression of proteins targeted to the periplasmic space by means of a cleavable leader sequence and two in-frame 8 residue tag sequences (FLAG tags).

Recombinant proteins were purified by the following methods, which are but two variations of well established techniques. (i) Bacterial clones in vector pGC were grown overnight in 2YT medium/37° C./200 rpm/100 mg/ml ampicillin, 1% glucose (final). Bacterial were diluted 1/100 into either 0.5 or 2 l of 2 YT medium supplemented with 100 mg/ml ampicillin, 0.1% glucose (final), and grown at 28° C./200 rpm. These cultures were grown to an optical density of between 0.2–0.4, at which stage they were induced with 1 mM IPTG (final). Cultures were allowed to grow for 16 hours (overnight) before harvesting. Bacteria were collected by centrifugation (Beckman JA-14 rotor or equivalent/6K/ 10 min/4° C.) and the periplasmic fraction collected by standard techniques. Briefly, this involved resuspension of bacterial pellets in a 1/25th volume of spheroplast forming buffer consisting of 100 mM Tris—HCl/0.5 M sucrose/0.5 mM EDTA (pH8.0), followed by addition of 1/500th volume of hen egg lysozyme (2 mg/ml in water) and incubation for 10 min. A 0.5×solution of the above spheroplasting buffer was then added to a final volume of 1/5th of the original culture, and the incubation continued for a further 20 min. The cell debris was then pelleted by centrifugation (Beckman JA-14 rotor or equivalent/9K/15 min/4° C.) and the supernatant containing the periplasmic fraction collected. All of the above procedures were performed at 4° C. Samples were processed immediately by sonication, filtration through a 4.5 μ nitrocellulose membrane and processed immediately or stored at 4° C. in the presence of sodium azide (0.05%). If freezing was required, no more than one freeze-thaw cycle was allowed. (ii) Bacterial clones in pPOW were grown overnight at 30° C. in 100 ml 2×YT broth containing 100 µg/ml (w/v) ampicillin. On the following day cultures were used to inoculate 900 ml fresh 2×YT broth containing 100 µg/ml (w/v) ampicillin, to OD600 nm=0.2–0.5, and grown at 30° C. with shaking (150–200 rpm) until OD600 nm=4 i.e. late log phase. To induce recombinant protein expression, the temperature was raised to 42° C. for 1 hour and then dropped to 20° C. for a further hour. Cells were harvested by centrifugation (Beckman JA-14/6K rpm/5 min/4° C.), the cell pellet resuspended in 100 ml extraction buffer (20 mM Tris pH 8.0/0.2 mg/ml (w/v) lysozyme/0.1% (v/v) Tween-20) and incubated at 4° C. overnight. Samples were sonicated for 30 seconds and cellular debris collected by centrifugation (Beckman JA-14/14K rpm/10 min/4° C.). The aqueous phase, containing the "lysozyme" wash, was retained. Cell pellets were then washed twice with ice-cold water and this "osmotic shock" wash was retained. Each wash consisted of resuspending the pellet in 100 ml ice-cold water followed by incubation on ice for 10 minutes in the first instance followed by 1 hour in the second instance. Following centrifugation (Beckman JA-14/14K rpm/10 min/4° C.), the pH of the aqueous phase was adjusted by addition of 10 ml 10×TBS, pH 8. The "lysozyme" and "osmotic shock" washes were pooled and constitute the soluble or "periplasmic" protein fraction. Periplasmic fractions were sonicated, filtered through a 0.45 µ nitrocellulose membrane and processed immediately or stored at 4° C. in the presence of sodium azide (0.5%), PMSF (23 µg/ml) and EDTA (50 mM).

Recombinant proteins were purified by affinity chromatography through a divinyl sulphone activated agarose (Mini-Leak)-linked anti-FLAG antibody column. Periplasmic extracts were directly loaded onto a 10 ml anti-FLAG column which had been pre-equilibrated in TBS (pH 8) containing 0.05% (w/v) sodium azide. Bound proteins were eluted with Immunopure Gentle Ag/Ab Elution Buffer (Pierce). Samples were then dialysed against TBS/0.05% (w/v) azide (pH 8), concentrated by ultrafiltration over a 3 kDa cut-off membrane (YM3, Diaflo), and analysed by HPLC on a pre-calibrated Superose 12 HR or Superdex 200 HR column (Pharmacia Biotech), at a flow rate of 0.5 ml/min. Fractions corresponding to monomeric, dimeric and tetrameric species were collected, concentrated as above, and stored at 4° C. prior to analysis. Protein concentration was determined spectrophotometrically using an extinction coefficient at A280 of 1.27 for the CTLA-4R extracellular domain, 0.92 for CTLA-4-Som1, 1.13 for CTLA-4-Som3, 1.05 for CTLA-4-Anti-Lys. All of the above protein chemistry methods are standard techniques within the field. Purified proteins were analysed by standard techniques for example polyacrylamide gel electrophoresis, western blot, dot blot etc.

Cloning and expression in the bacteriophage expression vectors pHFA, pFAB.5c and fd-tet dog, and subsequent production of recombinant bacteriophage, were by standard and well-established techniques. Screening of libraries of randomised CTLA-4 STMs was by standard and well-established techniques (Galanis et al 1997).

EXAMPLE 3

CTLA-4 STMs Incorporating Somatostatin and Haemagglutinin Peptides

Initially the CDR1 or the CDR3 loop structures of the CTLA-4 STM were replaced with the somatostatin polypeptide. This 14 residue polypetide is conformationally constrained by an intra-disulphide linkage between Cys3 and Cys14 (FIG. 4). This was reasoned to form a discrete protein loop, analogous to the CDR loops found in antibodies, and particularly analogous to the long CDRs found in camelid antibodies which are also stabilised by a disulphide linkage. The effect of substituting CDR1 in the presence or absence of Cys120 ie, whether a dimer could be produced, was also tested. These experiments produced an unexpected and surprising result. Substitution of either CDR-1 or -3 with somatostatin significantly enhanced the production of monomeric protein. This is illustrated in FIG. 5 where replacement of the CDR-3 loop structure with somatostatin significantly increased the ratio of monomeric to dimeric/tetrameric protein species.

In further experiments, simultaneous replacement of both CDR-1 and -3 loop structures by somatostatin resulted in production of high-levels of monomeric protein. This shows that extensive loop structure replacements can be accommodated by the CTLA-4 scaffolding. Structurally, one of the somatostatin loops may lie flat against the face of the molecule in a manner analogous to that of the CDR-3 loop structure of CTLA-4 VLD.

In a further extension of the CDR loop structure-replacement strategy, a region corresponding to CDR-2 was replaced with the 8-residue haemagglutinin (HA) tag sequence. Use of the conformationally constrained somatostatin loop in this position was considered unsuitable as this region partially encompasses the C" beta strand running the length of the molecule. The HA tag could be detected upon this CTLA-4 STM by use of an anti-HA antibody. Gel filtration experiments showed the presence of a range of protein species, from monomeric through to aggregated species suggesting that CDR-2-only substitutions were not stable (FIGS 6,7).

Final proof of principle that the CTLA-4 CDR loop structures could be replaced with other polypeptides to produce monomeric, soluble, STMs was by simultaneous replacement of all three CDR loop structures with two somatostatin and one HA epitope respectively. This STM produced a correctly folded and monomeric protein upon gel filtration chromatography (FIGS 6,7).

The positions of CDR loop structure substitutions within the CTLA-4 VLD for the various STMs are shown in FIG. 6. HPLC profiles of affinity-purified STM proteins are shown in FIG. 7. Identical results were obtained for proteins produced in two different protein expression systems: pGC where protein expression is chemically induced, and pPOW where protein expression is temperature induced (See Example 2)(FIG. 8). Polyacrylamide gel electrophoresis followed by western blot analysis indicated that the CTLA-4 STMs could be reduced and ran at the expected molecular weights and absent of glycosylation. Testing of isolated monomeric STM proteins showed that they remained monomeric after zero, one, or two freeze-thaw cycles (FIG. 9).

CTLA-4 STMs retained the correct conformation since a conformationally-specific anti-CTLA-4 antibody recognised STMs with both CDR1 and -3 loop structure replacements. Interestingly, this antibody recognised the wild type monomer and the dimer (CDR1 replaced) poorly, contrasting with the strong reaction observed for the modified protein species. This suggests that in the wild type STM some form of local interaction is occurring that occludes the antibody binding site, and that this interaction is similar to the result when two CTLA-4 molecules are tethered together (presumably blocking access to the antibody).

EXAMPLE 4

CTLA-4 STMs Based Upon a Camel Anti-Lysozyme Antibody

The camel $V_H$H antibody cAb-Lys3 isolated from immunised camels specifically binds within the active site cleft of hen egg lysozyme (Desmyter et al. 1996). To illustrate the ability of CTLA-4 STMs to function in a similar fashion, the three CDR loop structures of CTLA-4 VLD STM were replaced with the three CDR loop regions from cAb-Lys3. Positions and sequence of the substitutions are shown in FIG. 6. Expression of the STM (2V8) in either pGC or pPOW based expression systems resulted in production of predominantly monomeric soluble protein (FIGS. 7, 8). Protein solubility of this CTLA-4 STM was superior to native CTLA-4 VLD. ELISA analysis showed that (pGC produced) purified monomeric protein specifically bound hen egg lysozyme compared to non-specific antigens and compared to the CTLA-4 STM with somatostatin substituted within the CDR1 loop structure (PP2)(FIG. 10A). Read-time binding analysis by BIAcore showed that the lysozyme specifically bound to immobilised anti-lysozyme STM (FIG. 10B). The CTLA-4 STM framework is thus folding correctly and presenting the CDR loop structures in a manner in which they can bind lysozyme antigen. To further enhance expression of the CTLA-4 VLD anti-lysozyme, the coding sequence was adjusted by splice overlap PCR to comprise codons preferential for *E. coli* expression.

EXAMPLE 5

CTLA-4 STMs Based Upon a Human Anti-Melanoma Antibody

The human-derived anti-melanoma antibody V86 specifically binds human melanoma cells. This antibody is unusual in that binding affinity resides entirely within the $V_H$ region, addition of a cognate $V_L$ decreases binding efficiency, and that the $V_H$ domain expressed with a small segment of the $V_L$ domain has a high degree of solubility (Cai and Garen, 1997). To further illustrate that replacement of CTLA-4 VLD CDR loop structures enhances solubility and that the resultant STMs can be produced in bacterial expression systems, the three CDR loop structures of CTLA-4 were replaced with the three CDR loop regions from V86. Positions and sequence of the substitutions are shown in FIG. 6. Expression of this STM (3E4) in pGC again resulted in production of predominantly monomeric soluble protein (FIG. 7) with enhanced solubility compared to the CTLA-4 VLD.

EXAMPLE 6

Constructions of CTLA-4 STMs as Libraries of Binding Molecules

To select CTLA-4 STMs with novel binding specificities, VLD libraries were produced containing randomised CDR1 and CDR3 loop structures. Oligonucleotide primers used for library constructions are listed in FIG. 1. Combinations of oligonucleotide primers used for library construction are shown in Table 3.

TABLE 3

CTLA-4 STM Library Combinations

| | CDR1 | | | | | | | |
|---|---|---|---|---|---|---|---|---|
| CDR3 | 4483* | 4254 | 5449 | 5451 | 5452 | 5459 | 5446 | 4835 |
| 4482 | +1 | +1 | ///////// | ///////// | ///////// | ///////// | ///////// | ///////// |
| 4275 | +1 | +1 | ///////// | ///////// | ///////// | ///////// | ///////// | ///////// |
| 5470 | ///////// | ///////// | +2 | +2 | +2 | +2 | +2 | ///////// |
| 5474 | ///////// | ///////// | +2 | +2 | +2 | +2 | +2 | ///////// |
| 5471 | ///////// | ///////// | +2 | +2 | +2 | +2 | +2 | ///////// |
| 5472 | ///////// | ///////// | +2 | +2 | +2 | +2 | +2 | ///////// |
| 5475 | ///////// | ///////// | +2 | +2 | +2 | +2 | +2 | ///////// |
| 5473 | ///////// | ///////// | +2 | +2 | +2 | +2 | +2 | ///////// |
| 4836 | ///////// | ///////// | ///////// | ///////// | ///////// | ///////// | ///////// | +3 |

*: oligonucleotide number.
+: library combination.
1, 2, 3: describes library number.

DNA constructs encoding the resultant libraries were cloned into vectors pHFA or pFAB.5c for production of fd-phagemid based libraries and into pfd-Tet-Dog for production of fd-phage based libraries (see examples 1 and 2). Library 1 was cloned into vector pHFA and consisted of $2.1\times10^7$ independent clones. Library 3 was cloned into vectors pHFA ($5.7\times10^5$ independent clones) and pfd-Tet-Dog ($2.2\times10^4$ independent clones). Library 2 was cloned into pFAB.5c ($1.7\times10^7$ independent clones) and into pft-Tet-Dog ($1.6\times10^5$ independent clones). Numbers of independent clones were determined by counting gross numbers of transformed colonies constituting the library, followed by assaying for the presence and proportion of CTLA-4 STM-specific DNA.

For library 2, the variability of the full library was tested by sequencing of representative clones. These results are presented in Table 4. The expected heterogeneity of insert size and sequence was observed. A high proportion of UAG termination codons were observed, consistent with the oligonucleotide randomisation strategy. To prevent these codons causing premature termination of the CTLA-4 STM gene3 protein fusions, libraries were transferred into the *E. coli* strains Tg-1 and JM109, which suppress this termination codon by insertion of a glutamic acid residue. Cysteine residues were present in the high numbers expected from the design of the oligonucleotide and were in positions capable of forming intra- and inter-CDR loop structure disulphide bonds.

TABLE 4

CDR1 and CDR3 Inserts from a Representative Series of Library 2 Clones
(SEQ ID NOS: 102–142)

| CLONE | CDR1 | CDR3 |
|---|---|---|
| 3M-2 | ND1 | LPSSTDTRAYS (SEQ ID NO: 102) |
| 3M-3 | QESGGRPG (SEQ ID NO: 103) | LPRGPPLLSL (SEQ ID NO: 104) |
| 3M-5 | SPGRCLN (SEQ ID NO: 105) | ND |
| 3M-6 | EWKREHGG (SEQ ID NO: 106) | LCPGACGCVY (SEQ ID NO: 107) |
| 3M-7 | NSGENEGG (SEQ ID NO: 108) | ND |
| 3M-11 | DKPVTKSG (SEQ ID NO: 109) | ND |
| 3M-17 | SPGACPE (SEQ ID NO: 110) | ND |
| 3M-18 | SPGKCDQ (SEQ ID NO: 111) | ND |
| 3M-19 | SPGMCAR (SEQ ID NO: 112) | LMYPPPYYL (SEQ ID NO: 63) |
| 3M-20 | ND | PFLFLPCEFFF (SEQ ID NO: 113) |
| 3N-1 | WTLGHHKLCEG (SEQ ID NO: 114) | LTFCLLALCS (SEQ ID NO: 115) |
| 3N-2 | SPGECYG (SEQ ID NO: 116) | SWLSTTXCLSSCS (SEQ ID NO: 117) |
| 3N-3 | SPGECQD (SEQ ID NO: 118) | LLGSLLSCFASLS (SEQ ID NO: 119) |
| 3N-4 | SPECQD (SEQ ID NO: 142) | SPGSLLSCFASXS (SEQ ID NO: 120) |
| 3N-5 | SPGRCTD (SEQ ID NO: 121) | VICHSSVCLSD/EVC (SEQ ID NOS: 122–123) |
| 3N-6 | ND | DLPSYLACSI (SEQ ID NO: 124) |
| 3N-7 | SPGRCDA (SEQ ID NO: 125) | ALCWDVFYCSFPSY (SEQ ID NO: 126) |
| 3N-8 | ELFGHARYCKG (SEQ ID NO: 127) | VSITSPELCPVKVFD (SEQ ID NO: 128) |
| 3N-9 | SPGKVEN (SEQ ID NO: 129) | LFVPFVSP (SEQ ID NO: 130) |
| 3N-12 | SPGDLWV (SEQ ID NO: 131) | ESGLSPVSPCSLYSL (SEQ ID NO: 132) |
| 3N-13 | TSANGPYG (SEQ ID NO: 133) | PWAYRFLAVL (SEQ ID NO: 134) |
| 3N-14 | RKTREKYG (SEQ ID NO: 135) | ELMYPPPYYLGI (SEQ ID NO: 136) |
| 3N-15 | SPGQELT (SEQ ID NO: 137) | ELFFLLYAPCYLFQR (SEQ ID NO: 138) |

ND: Not Done
*: UAG termination codon

Bacteriophage particles displaying CTLA-4 STMs as gene 3 protein fusions were rescued from E. coli cells by standard protocols and panned against antigens presented in a number of contexts as described in the following examples.

EXAMPLE 7

CTLA-4 STM Libraries: Selection Against Antigens On Solid Supports

Four different antigens falling into a class of proteins with clefts or crevices within their structures were selected for screening. It was anticipated that the CTLA-4 VLD STMs, being of smaller size than antibodies, and possessing elongated CDR loop structures (especially CDR-3) would be able to access these cleft regions. The antigens selected were: (i) hen egg lysozyme (EC 3.2.1.17); (ii) bovine carbonic anhydrase (EC 4.2.1.1); (iii) fungal a-amylase (EC 3.2.1.1); and (iv) Streptoalloteichus hindustanis resistance protein ShBle (Gatignol et al. 1988). For binding to plates, antigens in coating buffer (1 mg/ml in 0.1 M NaHCO3 pH8.5) were bound to Costar ELISA plates by standard procedures. Rescued phage and phagemid-derived libraries were panned by standard and well-understood procedures except that lower than standard number of washes were employed to allow low affinity binding phage to be selected. FIG. 11 shows titres of libraries selected against ShBle. After round 4, recovered bacteriophage titres were higher than controls. To those skilled in the art, this represents selection of specific binding moieties, and it is then a routing process to produce these selected CTLA-4 VLD STMs using expression vectors such as pGC or pPOW (as described in example 2).

EXAMPLE 8

CTLA-4 STM Libraries: Selection Against Antigens In Solution

For selection in solution, the antigens bovine carbonic anhydrase and fungal a-amylase were biotinylated and selections performed in solution using capture by streptavidin coated magnetic beads. Throughout these experiments washes were kept constant at either 2 or 5 washes per selection round. Titres of recovered bacteriophage post-elution are shown in FIG. 12. After round 4, recovered bacteriophage titres were higher than controls. To those skilled in the art, this represents selection of specific binding moieties, and it is then a routing process to produce these selected CTLA-4 VLD STMs using expression vectors such as pGC or pPOW (as described in example 2).

EXAMPLE 9

CTLA-4 STM Libraries: Selection In An Alternative Display and Selection System To allow further maturation and selection of antigen binding STMs, the CTLA-4 STM library was ligated into a plasmid to add a downstream C-terminal spacer polypeptide (heavy constant domain). Upstream transcriptional and translational initiation sequences were added by PCR amplification using specific oligonucleotides (FIG. 1). The PCR DNA was used as a template for production of RNA followed by translation and display of the library on ribosomes in a coupled cell free translation system as described by He and Taussig (1997). To demonstrate binding, CTLA-4 STM ribosome complexes were panned on hepatitis B surface antigen (hbsa), glycophorin (glyA) and bovine serum albumin (BSA) coated dynabeads. RNA from ribosome complexes bound to hbsa, glyA and BSA was recovered by RT—PCR. It is then a routine process to clone these RT—PCR products into an expression vector such as pGC or pPOW (as described in example 2) allowing production of CTLA-4 STMs. It will be appreciated by persons skilled in the art that numerous variations and/or modifications may be made to the invention allowing display of libraries of CTLA-4 STMs as ribosome complexes (as in this example) as well as display on the surface of live cells (which may be derived from a eukaryotic or prokaryotic background) and may include bacteria, yeast, mammalian or insect cells.

EXAMPLE 10

CTLA-4 STMs: Affinity Maturation And CDR2 Mutation

To allow further maturation and selection of antigen-binding STMs, and the construction of randomised CDR-1, -2 and -3 libraries, CDR-2 randomised oligonucleotide primers were produced (FIG. 1). A variation of these primers contained conserved cysteine residues to allow construction of STMs with CDR2—CDR3 disulphide linkages mimicing those found in llama single domain antibodies. Splice overlap PCR allowed creation of libraries containing all three CDR loop structures randomised.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

Bodian D L, Jones E Y, Harlos K, Stuart D I, Davis S J (1984) Crystal structure of the extracellular region of the human cell adhesion molecule CD2 at 2.5 A resolution. Structure 2: 755–766

Cai X and Garen A (1997) Comparison of fusion phage libraries displaying VH or single-chain Fv antibody fragments derived from the antibody repertoire of a vaccinated melanoma patient as a source of melanoma-specific targeting molecules Immunol 94: 9261–9266

Canfield V A, Norbeck L, Levenson R (1996) Localization of cytoplasmic and extracellular domains of Na,K-ATPase by eptitope tag insertion Biochem. 35: 14165–14172

Coia, G., Hudson, P. J., Lilley, G. G. (1996) Construction of recombinant extended single-chain antibody peptide conjugates for use in the diagnosis of HIV-1 and HIV-2. J. Immunol. Meth. 192:13–23

Davies J. Riechmann L (1994) Camelising human antibody fragments: NMR studies on $V_H$ domains FEBS Lett. 339 (3):285–90

Davies J. Riechmann L. (1996) Single antibody domains as small recognition units: design and in vitro antigen selection of camelized, human $V_H$ domains with improved protein stability Protein Eng 9(6):531–7

Desmyter A, Transue T R, Ghahroudi M A, Thi M H, Poortmans F. Hamers R, Muyldermans S, Wyns L (1996) Crystal structure of a camel single-domain VH antibody fragment in complex with lysozyme Nat Struct Biol 3:803–811

Galanis M, Irving R A, and Hudson P J (1997) Current Protocols in Immunology, 17.1.1–17.1.45.

Gatignol A, Durand H, and Tiraby G (1988) Bleomycin resistance conferred by a drug-binding protein FEBS Lett 230: 171–175

Gerstmayer B, Pessara U, Wels W (1997) Consturction and expression in the yeast Pichia pastoris of functionally active soluble forms of the human costimulatory molecules B7-1 and B7-2 and the B7 counter-receptor CTLA-4 FEBS Lett 407: 63–68

Hamers-Casterman C, Atarhouch T, Muyldermans S, Robinson G, Hamers C, Songa E B, Bendahman N, Hmers R (1993) Natually occurring antibodies devoid of light chains. Nature 363: 446–448

Hanes J and Pluckthun A (1997) In vitro selection and evolution of functional proteins by using ribosome display Proc.Natl.Acad. Sci. USA. 94: 4937–4942

He M and Taussig M J (1997) Antibody-ribosome-mRNA (ARM) complexes as efficient selection particles for in vitro display and evoluton of antibody combining sites. Nucl. Acids Res. 25: 5132–5134

Hoogenboom, H. R., Griffiths, A. D., Johnson, K. S., Chiswell, D. J., Hudson, P., and Winter, G. 1991. Multi-subunit proteins on the surface of filamentous phage: methodologies for displaying antibody (Fab) heavy and light chains. Nucleic Acids Res. 19: 4133–4137.

Huse, W. D., Sastry, L., Iverson, S. A., Kang, A. S., Alting, M. M., Burton, D. R., Benkovic, S. J., & Lerner, R. A. (1989). Generation of a large combinatorial library of the immunoglobulin repertoire in phage lambda. Science, 246: 1275–81.

Hutloff, A., Dittrich, A. M., Beier, K. C., Elijachewitsch, B., Kraft, R., Anagnostopoulos, I. and Kroczek, R. A. (1999). ICOS is an inducible T-cell co-stimulator structurally and functionally related to CD28. Nature 397: 263–266.

Kortt, A. A., Guthrie, R. E., Hinds, M. G., Power, B. E., Ivancic, N., Caldwell, J. B., Gruen, L. C., Norton, R. S. and Hudson, P. J. (1995) Solution properties of E. coli expressed VH domain of anti-neuraminidase antibody NC41. J. Protein Chemistry: 14, 167–178.

Linsley, P S, Clark E A, and Ledbetter J A (1990) The T cell antigen CD28 mediates adhesion with B cells by interacting with the activation antigen, B7/BB1 Proc. Natl. Acad. Sci USA 87: 5031.

Linsley P S, Nadler S G, Bajorath J, Peach R, Leung H T, Rogers J, Bradshaw J, Stebbins M, Leytze G, Brady W, et al (1995) Binding stoichiometry of the cytotoxic T lymphocyte-associated molecule-4 (CTLA-4). A disulphide-linked homodimer binds two CD86 molecules. J Biol Chem 270: 15417–24

McCafferty, J., Griffiths, A. D., Winter, G., & Chiswell, D. J. (1990). Phage antibodies: filamentous phage displaying antibody variable domains. Nature. 348: 552–4.

Metzler W J, Bajorath J, Fenderson W, Shaw S Y, Constantine K L, Naemura J, Leytze G, Peach R J, Lavoie T B, Mueller L, Linsley P S (1997) Solution structure of human CTLA-4 and delineation of a CD80/CD86 binding site conserved in CD28 Nat Struct Biol 4: 527–531

Morton P A, FU X T, Steward J A, Giacoletto K S, White S L, Leysath C E, Evans R J, Shieh J J, Karr R W (1996) Differential effects of CTLA-4 substitutions on the binding of human CD80 (B7-1) and CD86 (B7-2) J Immunol 156: 1047–1054

Muyldermans S, Atarhouch T, Saldanha J, Barbosa J A, Hamers R (1994) Sequence and structure of VH domain from naturally occurring camel heavy chain immunoglobulins lacking light chains. Protein Eng 7: 1129–1135.

Nieba L, Honegger A, Krebber C, Pluckthun A (1997) Disrupting the hydrophobic patches at the antibody variable/constant domain interface: improved in invivo folding and physical characterization of an engineered scFv fragment Protein Engineering (4):435–44

Novotny J, Ganju R K, Smiley S T, Hussey R E, Luther M A, Recny M A, Siliciano R F, Reinherz E L (1991) A soluble, single-chain T-cell receptor fragment endowed with antigen-combining properties Proc Natl Acad Sci U S A 88(19): 8646–8650.

Peach R J, Bajorath J, Brady W, Leytze G, Greene J, Naemura J, Linsley P S (1994) Complimentarity determining region 1 (CDR1)- and CDR3-analgous regions in CTLA-4 and CD28 determine the binding to B7-1 J Exp Med 180: 2049–2058

Power, B. E., Ivancic, N., Harley, V. R., Webster, R. G., Kortt, A. A, Irving, R. A. and Hudson, P. J. (1992) High-level temperature-induced synthesis of an antibody VH-domain in *Escherichia coli* using the PelB secretion signal gene 113: 95–99.

Reisine, T. (1995) Somatostatin. Cell Molec. Neurobiol. 15: 597–614

Reubi, J. C. (1997) Regulatory peptice receptors as molecular targets for cancer diagnosis and therapy. Q. J. Nucl. Med. 41: 63–70

Schonbrunn A, Gu Y Z, Brown P J, Loose-Mitchell D (1995) Funtion and regulation of somatostatin receptor subtypes. Ciba Found. Symp. 190: 204–217

Smith, G. P. (1985). Filamentous fusino phage: novel expression vectors that display cloned antigens on the virion surface. Science, 228, 1315–1317 van der Merwe P A, Bodian D L, Daenke S, Linsley P, Davis S J (1997) CD80 (B7-1) binds both CD28 and CTLA-4 with a low affinity and very fast kinetics. J Exp Med 185: 393–403

Vu K B, Ghahroudi M A, Wyns L, Muyldermans S (1997) Comparison of llama VH sequences from conventional and Heavy Chain Antibodies. Molec Immunol 34: 1121–1131

Ward E S (1991) Expression and secretion of T-cell receptor V alpha and V beta domain using *Escherichia coli* as a host Scand J Immunol 34(2):215–220.

Waterhouse P, Marengere L E, Mittrücker H W, Mak T W (1996) CTLA-4, a negative regulator of T-lymphocyte activation. Immunol Rev 153: 183–207

Waterhouse P, Penninger J M, Timms E, Wakeham A, Shahinian A, Lee K P, Thompson C B, Griesser H, Mak T W (1995) Lymphoproliferative disorders with early lethality in mice deficient in Ctla-4 Science 270: 985–988

Winter G, Milstein C. (1991). Man-made antibodies. Nature. 349: 293–299.

Wulfing C, Pluckthun A and in (1994) Correctly folded T-cell receptor fragments in the periplasm of *Escherichia coli*—Influence of folding catalysts J Mol Biol 242(5): 655–69.

The invention claimed is:

1. A modified monomeric non-antibody ligand V-like domain (VLD) comprising within the VLD at least one CDR loop structure or part thereof that is modified or replaced such that
   (i) the size of the CDR loop structure or part thereof is increased by at least one amino acid residue when compared with the corresponding CDR loop structure or part thereof in an unmodified VLD; and/or
   (ii) the modification or replacement results in formation of a disulphide bond within or between one or more of the CDR loop structures,
wherein the CDR loop structure is a surface polypeptide loop structure corresponding to a complementarity determining region of an antibody V-domain, and wherein the non-antibody ligand is selected from the group consisting of CTLA-4, CD28 and ICOS.

2. The modified VLD according to claim 1, wherein the size of the CDR loop structure or part thereof is increased by at least two amino acid residues.

3. The modified VLD according to claim 1, wherein the size of the CDR loop structure or part thereof is increased by at least six amino acid residues.

4. The modified VLD according to claim 1, wherein the size of the CDR loop structure or part thereof is increased by at least nine amino acid residues.

5. The modified VLD according to claim 1, wherein the binding affinity of the modified VLD is altered when compared with the unmodified VLD.

6. The modified VLD according to claim 5, wherein the affinity of the modified VLD to at least one natural ligand of the unmodified VLD is reduced.

7. The modified VLD according to claim 1, wherein the binding specificity of the modified VLD is different than that of the unmodified VLD.

8. The modified VLD according to claim 1, wherein the non-antibody ligand is CTLA-4.

9. The modified VLD according to claim 1, wherein one or more of the CDR loop structure(s) or part(s) thereof is replaced with a binding determinant derived from a non-antibody polypeptide.

10. The modified VLD according to claim 9, wherein the binding determinant is derived from somatostatin or haemagglutinin.

11. The modified VLD according to claim 1, wherein one or more of the CDR loop structure(s) or parts thereof is replaced with one or more CDR loop structures derived from an antibody or antibodies.

12. The modified VLD according to claim 11, wherein the antibody or antibodies are derived from a rat, mouse, human, camel, llama or shark.

13. The modified VLD according to claim 1, linked to a diagnostic reagent.

14. The modified VLD according to claim 13, wherein the diagnostic reagent is selected from the group consisting of streptavidin, biotin, a radioisotope, a dye marker and an imaging reagent.

15. A multivalent reagent comprising two or more modified VLDs as claimed in claim 1.

16. The modified VLD according to claim 1, immobilized on a solid support or coupled to a biosensor surface.

17. A composition in a pharmaceutically acceptable carrier or diluent comprising a modified VLD as claimed in claim 1.

18. The modified VLD according to claim 1, wherein at least two CDR loop structures or parts thereof are modified or replaced.

19. The modified VLD according to claim 1, wherein three CDR loop structures or parts thereof are modified or replaced.

20. The modified monomeric VLD according to claim 1, wherein the solubility of the modified VLD is improved when compared with the unmodified VLD.

21. The multivalent reagent according to claim 15, immobilized on a solid support or coupled to a biosensor surface.

22. A composition in a pharmaceutically acceptable carrier or diluent comprising multivalent reagent as claimed in claim 15.

* * * * *

UNITED STATES PATENT AND TRADEMARK OFFICE
CERTIFICATE OF CORRECTION

| | | |
|---|---|---|
| PATENT NO. | : 7,166,697 B1 | Page 1 of 1 |
| APPLICATION NO. | : 09/623611 | |
| DATED | : January 23, 2007 | |
| INVENTOR(S) | : Galanis et al. | |

It is certified that error appears in the above-identified patent and that said Letters Patent is hereby corrected as shown below:

In the Drawing

Sheet 9, Figure 4, text should read as follows:

Figure 4: Schematic representation of the somatostatin peptide. (SEQ ID NO:60)

Signed and Sealed this

Eighth Day of April, 2008

JON W. DUDAS
*Director of the United States Patent and Trademark Office*

SEQUENCE LISTING

```
<160> NUMBER OF SEQ ID NOS: 142

<210> SEQ ID NO 1
<211> LENGTH: 6
<212> TYPE: PRT
<213> ORGANISM: Homo Sapiens
<220> FEATURE:
<221> NAME/KEY: UNSURE
<222> LOCATION: (1)..(6)
<223> OTHER INFORMATION: conserved sequence in CDR3-like surface loop

<400> SEQUENCE: 1

Met Tyr Pro Pro Pro Tyr
1               5

<210> SEQ ID NO 2
<211> LENGTH: 54
<212> TYPE: DNA
<213> ORGANISM: Artificial Sequence
<220> FEATURE:
<223> OTHER INFORMATION: Oligonucleotide for 5' CTLA-4 amplification

<400> SEQUENCE: 2
ttattactcg cggcccagcc ggccatggcc gcaatgcacg tggcccagcc tgct            54

<210> SEQ ID NO 3
<211> LENGTH: 60
<212> TYPE: DNA
<213> ORGANISM: Artificial Sequence
<220> FEATURE:
<223> OTHER INFORMATION: Oligonucleotide for 5' CTLA-4 amplification
```

```
<400> SEQUENCE: 3
ttattactcg cggcccagcc ggccatggcc gcaatgcacg tggcccagcc tgctgtggta      60

<210> SEQ ID NO 4
<211> LENGTH: 45
<212> TYPE: DNA
<213> ORGANISM: Artificial Sequence
<220> FEATURE:
<223> OTHER INFORMATION: Oligonucleotide for 5' CTLA-4 amplification

<400> SEQUENCE: 4
tctcacagtg cacaggcaat gcacgtggcc cagcctgctg tggta                     45

<210> SEQ ID NO 5
<211> LENGTH: 39
<212> TYPE: DNA
<213> ORGANISM: Artificial Sequence
<220> FEATURE:
<223> OTHER INFORMATION: Oligonucleotide for 5' CTLA-4 amplification

<400> SEQUENCE: 5
tctcacagtg cacaggcaat gcacgtggcc cagcctgct                            39

<210> SEQ ID NO 6
<211> LENGTH: 42
<212> TYPE: DNA
<213> ORGANISM: Artificial Sequence
<220> FEATURE:
<223> OTHER INFORMATION: Oligonucleotide for 5' CTLA-4 amplification

<400> SEQUENCE: 6
gcccagccgg ccgaattcgc aatgcacgtg gcccagcctg ct                        42

<210> SEQ ID NO 7
<211> LENGTH: 60
<212> TYPE: DNA
<213> ORGANISM: Artificial Sequence
<220> FEATURE:
<223> OTHER INFORMATION: Oligonucleotide for 5' CTLA-4 amplification

<400> SEQUENCE: 7
gcagctaata cgactcacta taggaacaga ccaccatgga cgtggcccag cctgctgtgg      60

<210> SEQ ID NO 8
<211> LENGTH: 42
<212> TYPE: DNA
<213> ORGANISM: Artificial Sequence
<220> FEATURE:
<223> OTHER INFORMATION: Oligonucleotide for 3' CTLA-4 amplification

<400> SEQUENCE: 8
atctgcggcc gctacataaa tctgggtacc gttgccgatg cc                        42

<210> SEQ ID NO 9
<211> LENGTH: 66
<212> TYPE: DNA
<213> ORGANISM: Artificial Sequence
<220> FEATURE:
<223> OTHER INFORMATION: Oligonucleotide for 3' CTLA-4 amplification

<400> SEQUENCE: 9
gctgaattct gatcagtgat ggtgatggtg atgtgcggcc gcgtcagaat ctgggcacgg      60
ttctgg                                                                66
```

<210> SEQ ID NO 10
<211> LENGTH: 51
<212> TYPE: DNA
<213> ORGANISM: Artificial Sequence
<220> FEATURE:
<223> OTHER INFORMATION: Oligonucleotide for 3' CTLA-4 amplification

<400> SEQUENCE: 10
gcccttgggc cgggagatgg tctgcttcag tggcgagggc aggtctgtgt g      51

<210> SEQ ID NO 11
<211> LENGTH: 49
<212> TYPE: DNA
<213> ORGANISM: Artificial Sequence
<220> FEATURE:
<223> OTHER INFORMATION: Oligonucleotide for 3' CTLA-4 amplification

<400> SEQUENCE: 11
cgagggcagg tctgtgtggg tcacggtgca cgtgaacctc tccccggag           49

<210> SEQ ID NO 12
<211> LENGTH: 51
<212> TYPE: DNA
<213> ORGANISM: Artificial Sequence
<220> FEATURE:
<223> OTHER INFORMATION: Oligonucleotide for 3' CTLA-4 amplification

<400> SEQUENCE: 12
cgtgaacctc tccccggagt tccagtcatc ctcgcagatg ctggcctcac c        51

<210> SEQ ID NO 13
<211> LENGTH: 84
<212> TYPE: DNA
<213> ORGANISM: Artificial Sequence
<220> FEATURE:
<223> OTHER INFORMATION: Oligonucleotide for CDR1- somatostatin

<400> SEQUENCE: 13
agctttgtgt gtgagtatgc agctggctgc aagaatttct tctggaagac tttcacatcc    60
tgtgccactg aggtccgggt gaca                                          84

<210> SEQ ID NO 14
<211> LENGTH: 84
<212> TYPE: DNA
<213> ORGANISM: Artificial Sequence
<220> FEATURE:
<223> OTHER INFORMATION: Oligonucleotide for CDR3- somatostatin

<400> SEQUENCE: 14
ctgggtaccg ttgccgatgc cacaggatgt gaaagtcttc cagaagaaat tcttgcagcc    60
agcctccacc ttgcagatgt agag                                          84

<210> SEQ ID NO 15
<211> LENGTH: 75
<212> TYPE: DNA
<213> ORGANISM: Artificial Sequence
<220> FEATURE:
<223> OTHER INFORMATION: Oligonucleotide for CDR1- som- randomisation
<221> NAME/KEY: misc_feature
<222> LOCATION: (1)..(75)
<223> OTHER INFORMATION: "n" can be a,t,g or c
<221> NAME/KEY: misc_feature
<222> LOCATION: (1)..(75)
<223> OTHER INFORMATION: "k" is g or t

<400> SEQUENCE: 15

```
agctttgtgt gtgagtatgc agctggctgc aagaatnnkn nknnknnknn knnkacatcc    60
tgtgccactg aggtc                                                    75
```

<210> SEQ ID NO 16
<211> LENGTH: 75
<212> TYPE: DNA
<213> ORGANISM: Artificial Sequence
<220> FEATURE:
<223> OTHER INFORMATION: Oligonucleotide for CDR3- som- randomisation
<221> NAME/KEY: misc_feature
<222> LOCATION: (1)..(75)
<223> OTHER INFORMATION: "n" can be a,t,g or c
<221> NAME/KEY: misc_feature
<222> LOCATION: (1)..(75)
<223> OTHER INFORMATION: "m" is a or c

<400> SEQUENCE: 16

```
ctgggtaccg ttgccgatgc cacaggatgt mnnmnnmnnm nnmnnmnnat tcttgcagcc    60
agcctccacc ttgca                                                    75
```

<210> SEQ ID NO 17
<211> LENGTH: 21
<212> TYPE: DNA
<213> ORGANISM: Artificial Sequence
<220> FEATURE:
<223> OTHER INFORMATION: Oligonucleotide for CDR2 haemagglutinin tag

<400> SEQUENCE: 17

```
gtaggttgcc gcacagactt c                                             21
```

<210> SEQ ID NO 18
<211> LENGTH: 66
<212> TYPE: DNA
<213> ORGANISM: Artificial Sequence
<220> FEATURE:
<223> OTHER INFORMATION: Oligonucleotide for CDR2 haemagglutinin tag

<400> SEQUENCE: 18

```
gaagtctgtg cggcaaccta cccgtatgac gttccggact acgccctaga tgattccatc    60
tgcacg                                                              66
```

<210> SEQ ID NO 19
<211> LENGTH: 78
<212> TYPE: DNA
<213> ORGANISM: Artificial Sequence
<220> FEATURE:
<223> OTHER INFORMATION: Oligonucleotide for CDR-1 anti-lysozyme

<400> SEQUENCE: 19

```
gccagctttg tgtgtgagta tgccagtggc tacaccatcg ggccgtactg catgggcgtc    60
cgggtgacag tgcttcgg                                                 78
```

<210> SEQ ID NO 20
<211> LENGTH: 60
<212> TYPE: DNA
<213> ORGANISM: Artificial Sequence
<220> FEATURE:
<223> OTHER INFORMATION: Oligonucleotide for CDR-2 anti-lysozyme

<400> SEQUENCE: 20

```
tgtgcggcag ccatcaacat gggcggtggc atcaccttcc tagatgattc catctgcacg    60
```

<210> SEQ ID NO 21
<211> LENGTH: 60

```
<212> TYPE: DNA
<213> ORGANISM: Artificial Sequence
<220> FEATURE:
<223> OTHER INFORMATION: Oligonucleotide for CDR-2 anti-lysozyme

<400> SEQUENCE: 21
atctaggaag gtgatgccac cgcccatgtt gatggctgcc gcacagactt cagtcacctg    60

<210> SEQ ID NO 22
<211> LENGTH: 69
<212> TYPE: DNA
<213> ORGANISM: Artificial Sequence
<220> FEATURE:
<223> OTHER INFORMATION: Oligonucleotide for CDR-3 anti-lysozyme

<400> SEQUENCE: 22
cagcccgtgg ccgcactcgt agtaggacgc gtagatcgtc gagtccacct tgcagatgta    60
gagtcccgt                                                            69

<210> SEQ ID NO 23
<211> LENGTH: 72
<212> TYPE: DNA
<213> ORGANISM: Artificial Sequence
<220> FEATURE:
<223> OTHER INFORMATION: Oligonucleotide for CDR-3 anti-lysozyme

<400> SEQUENCE: 23
aatctgggta ccgttgccga tgccggagtc atagccgtac cctcccgtgg acagcccgtg    60
gccgcactcg ta                                                        72

<210> SEQ ID NO 24
<211> LENGTH: 78
<212> TYPE: DNA
<213> ORGANISM: Artificial Sequence
<220> FEATURE:
<223> OTHER INFORMATION: Oligonucleotide for CDR-1 anti-melanoma

<400> SEQUENCE: 24
gccagctttg tgtgtgagta tgccagtgga ttcaccttca gttcctacgc catgtccgtc    60
cgggtgacag tgcttcgg                                                  78

<210> SEQ ID NO 25
<211> LENGTH: 51
<212> TYPE: DNA
<213> ORGANISM: Artificial Sequence
<220> FEATURE:
<223> OTHER INFORMATION: Oligonucleotide for CDR-2 anti-melanoma

<400> SEQUENCE: 25
gccatctccg gatccggagg ctcgacctac ctagatgatt ccatctgcac g              51

<210> SEQ ID NO 26
<211> LENGTH: 54
<212> TYPE: DNA
<213> ORGANISM: Artificial Sequence
<220> FEATURE:
<223> OTHER INFORMATION: Oligonucleotide for CDR-2 anti-melanoma

<400> SEQUENCE: 26
gtaggtcgag cctccggatc cggagatggc tgccgcacag acttcagtca cctg           54

<210> SEQ ID NO 27
<211> LENGTH: 69
<212> TYPE: DNA
```

```
<213> ORGANISM: Artificial Sequence
<220> FEATURE:
<223> OTHER INFORMATION: Oligonucleotide for CDR-3 anti-melanoma

<400> SEQUENCE: 27
cacgtccatg tagtagtctc cctcctcgcc gcgcagtccc cagcccacct tgcagatgta      60
gagtcccgt                                                              69

<210> SEQ ID NO 28
<211> LENGTH: 51
<212> TYPE: DNA
<213> ORGANISM: Artificial Sequence
<220> FEATURE:
<223> OTHER INFORMATION: Oligonucleotide for CDR-3 anti-melanoma

<400> SEQUENCE: 28
aatctgggta ccgttgccga tgcccacgtc catgtagtag tctccctcct c                51

<210> SEQ ID NO 29
<211> LENGTH: 66
<212> TYPE: DNA
<213> ORGANISM: Artificial Sequence
<220> FEATURE:
<223> OTHER INFORMATION: Oligonucleotide for CDR-1 randomisation
<221> NAME/KEY: misc_feature
<222> LOCATION: (1)..(66)
<223> OTHER INFORMATION: "n" can be a,c,t or g
<221> NAME/KEY: misc_feature
<222> LOCATION: (1)..(66)
<223> OTHER INFORMATION: "k" can be 'g' or 't'

<400> SEQUENCE: 29
agctttgtgt gtgagtatgc annknnknnk nnknnknnkn nknnkgccac tgaggtccgg      60
gtgaca                                                                 66

<210> SEQ ID NO 30
<211> LENGTH: 68
<212> TYPE: DNA
<213> ORGANISM: Artificial Sequence
<220> FEATURE:
<223> OTHER INFORMATION: Oligonucleotide for CDR1 randomisation

<400> SEQUENCE: 30
cacgtggccc agcctgctgt ggtactggcc agcagccgag gcatcgccag ctttgtgtgt      60
gagtatgc                                                               68

<210> SEQ ID NO 31
<211> LENGTH: 66
<212> TYPE: DNA
<213> ORGANISM: Artificial Sequence
<220> FEATURE:
<223> OTHER INFORMATION: Oligonucleotide for CDR1 randomisation
<221> NAME/KEY: misc_feature
<222> LOCATION: (1)..(66)
<223> OTHER INFORMATION: "n" can be a,t,g or c
<221> NAME/KEY: misc_feature
<222> LOCATION: (1)..(66)
<223> OTHER INFORMATION: "s" can be g or c

<400> SEQUENCE: 31
gtgtgtgagt acgcgtncnn snnsnnsnns nnsnnstgcn nsgctactga ggttcgtgtg      60
accgtc                                                                 66

<210> SEQ ID NO 32
<211> LENGTH: 73
```

```
<212> TYPE: DNA
<213> ORGANISM: Artificial Sequence
<220> FEATURE:
<223> OTHER INFORMATION: Oligonucleotide for CDR1 randomisation
<221> NAME/KEY: misc_feature
<222> LOCATION: (25)..(26)
<223> OTHER INFORMATION: "X" can be a,t,g or c
<221> NAME/KEY: misc_feature
<222> LOCATION: (28)..(29)
<223> OTHER INFORMATION: "X" can be a,t,g or c
<221> NAME/KEY: misc_feature
<222> LOCATION: (31)..(32)
<223> OTHER INFORMATION: "X" can be a,t,g or c
<221> NAME/KEY: misc_feature
<222> LOCATION: (34)..(38)
<223> OTHER INFORMATION: "X" can be a,t,g or c
<221> NAME/KEY: misc_feature
<222> LOCATION: (40)..(41)
<223> OTHER INFORMATION: "X" can be a,t,g or c
<221> NAME/KEY: misc_feature
<222> LOCATION: (43)..(44)
<223> OTHER INFORMATION: "X" can be a,t,g or c

<400> SEQUENCE: 32
gccagctttg tgtgtgagta tgcannknnk nnknnknnkn nknnkggcgt ccgggtgaca    60
gtgcttcggc agg                                                      73

<210> SEQ ID NO 33
<211> LENGTH: 82
<212> TYPE: DNA
<213> ORGANISM: Artificial Sequence
<220> FEATURE:
<223> OTHER INFORMATION: Oligonucleotide for CDR1 randomisation
<221> NAME/KEY: misc_feature
<222> LOCATION: (1)..(82)
<223> OTHER INFORMATION: "n" can be a,c,t or g
<221> NAME/KEY: misc_feature
<222> LOCATION: (1)..(82)
<223> OTHER INFORMATION: "k" can be t or g

<400> SEQUENCE: 33
gccagctttg tgtgtgagta tgcannknnk nnknnknnkn nknnknnktg cnnkggcgtc    60
cgggtgacag tgcttcggca gg                                            82

<210> SEQ ID NO 34
<211> LENGTH: 82
<212> TYPE: DNA
<213> ORGANISM: Artificial Sequence
<220> FEATURE:
<223> OTHER INFORMATION: Oligonucleotide for CDR1 randomisation
<221> NAME/KEY: misc_feature
<222> LOCATION: (1)..(82)
<223> OTHER INFORMATION: "n" can be a,t g or c
<221> NAME/KEY: misc_feature
<222> LOCATION: (1)..(82)
<223> OTHER INFORMATION: "k" can be g or t

<400> SEQUENCE: 34
gccagctttg tgtgtgagta tgcannknnk ywynnkywyn nknnkwytg cnnkggcgtc     60 cgggtgacag tgcttcggca gg                                            82

<210> SEQ ID NO 35
<211> LENGTH: 70
<212> TYPE: DNA
<213> ORGANISM: Artificial Sequence
<220> FEATURE:
<223> OTHER INFORMATION: Oligonucleotide for CDR1 randomisation
<221> NAME/KEY: misc_feature
<222> LOCATION: (1)..(70)
<223> OTHER INFORMATION: "n" can be a,c,t or g
```

```
<221> NAME/KEY: misc_feature
<222> LOCATION: (1)..(70)
<223> OTHER INFORMATION: "k" can be t or g
<221> NAME/KEY: misc_feature
<222> LOCATION: (1)..(70)
<223> OTHER INFORMATION: "w" can be t or a
<221> NAME/KEY: misc_feature
<222> LOCATION: (1)..(70)
<223> OTHER INFORMATION: "t" can be t or c
<221> NAME/KEY: misc_feature
<222> LOCATION: (1)..(70)
<223> OTHER INFORMATION: "k" can be t or g

<400> SEQUENCE: 35
gccagctttg tgtgtgagta tgcatctcca ggcnnknnkn nknnkgtccg ggtgacagtg     60
cttcggcagg                                                           70

<210> SEQ ID NO 36
<211> LENGTH: 70
<212> TYPE: DNA
<213> ORGANISM: Artificial Sequence
<220> FEATURE:
<223> OTHER INFORMATION: Oligonucleotide for CDR1 randomisation
<221> NAME/KEY: misc_feature
<222> LOCATION: (1)..(70)
<223> OTHER INFORMATION: "n" can be a,t,g or c
<221> NAME/KEY: misc_feature
<222> LOCATION: (1)..(70)
<223> OTHER INFORMATION: "k" can be g or t

<400> SEQUENCE: 36
gccagctttg tgtgtgagta tgcatctcca ggcnnktgcn nknnkgtccg ggtgacagtg     60
cttcggcagg                                                           70

<210> SEQ ID NO 37
<211> LENGTH: 68
<212> TYPE: DNA
<213> ORGANISM: Artificial Sequence
<220> FEATURE:
<223> OTHER INFORMATION: Oligonucleotide for CDR-2 randomisation
<221> NAME/KEY: misc_feature
<222> LOCATION: (1)..(67)
<223> OTHER INFORMATION: "n" can be a,c,t or g
<221> NAME/KEY: misc_feature
<222> LOCATION: (1)..(67)
<223> OTHER INFORMATION: "k" can be t or g

<400> SEQUENCE: 37
gtgactgaag tctgtgcggc aacctacnnk nnkgggnnkg agttgacctt cctagatgat     60
tccatctg                                                             68

<210> SEQ ID NO 38
<211> LENGTH: 30
<212> TYPE: DNA
<213> ORGANISM: Artificial Sequence
<220> FEATURE:
<223> OTHER INFORMATION: Oligonucleotide for CDR-2 randomisation

<400> SEQUENCE: 38
gtaggttgcc gcacagactt cagtcacctg                                     30

<210> SEQ ID NO 39
<211> LENGTH: 68
<212> TYPE: DNA
<213> ORGANISM: Artificial Sequence
<220> FEATURE:
<223> OTHER INFORMATION: Oligonucleotide for CDR-2 randomisation
<221> NAME/KEY: misc_feature
```

```
<222> LOCATION: (1)..(68)
<223> OTHER INFORMATION: "n" can be a,t,g or c
<221> NAME/KEY: misc_feature
<222> LOCATION: (1)..(68)
<223> OTHER INFORMATION: "k" can be g or t

<400> SEQUENCE: 39
gtgactgaag tctgtgcggc atgctacnnk nnkgggnnkg agttgacctt cctagatgat    60
tccatctg                                                             68

<210> SEQ ID NO 40
<211> LENGTH: 30
<212> TYPE: DNA
<213> ORGANISM: Artificial Sequence
<220> FEATURE:
<223> OTHER INFORMATION: Oligonucleotide for CDR-2 randomisation

<400> SEQUENCE: 40
gtagcatgcc gcacagactt cagtcacctg                                     30

<210> SEQ ID NO 41
<211> LENGTH: 69
<212> TYPE: DNA
<213> ORGANISM: Artificial Sequence
<220> FEATURE:
<223> OTHER INFORMATION: Oligonucleotide for CDR-3 randomisation
<221> NAME/KEY: misc_feature
<222> LOCATION: (1)..(69)
<223> OTHER INFORMATION: "n" can be a,t,g or c
<221> NAME/KEY: misc_feature
<222> LOCATION: (1)..(69)
<223> OTHER INFORMATION: "m" can be a or c

<400> SEQUENCE: 41
ctgggtaccg ttgccgatgc cmnnmnnmnn mnnmnnmnnm nnmnnmnnct ccaccttgca    60
gatgtagag                                                            69

<210> SEQ ID NO 42
<211> LENGTH: 67
<212> TYPE: DNA
<213> ORGANISM: Artificial Sequence
<220> FEATURE:
<223> OTHER INFORMATION: Oligonucleotide for CDR3 randomisation
<221> NAME/KEY: misc_feature
<222> LOCATION: (1)..(67)
<223> OTHER INFORMATION: "n" can be a,c,t or g
<221> NAME/KEY: misc_feature
<222> LOCATION: (1)..(67)
<223> OTHER INFORMATION: "s" can be c or g

<400> SEQUENCE: 42
aggtggaann snnsnnsnns nnsnnstgcn nsnnsnnsnn snnsnnsnns ggcatcggca    60
acggtac                                                              67

<210> SEQ ID NO 43
<211> LENGTH: 78
<212> TYPE: DNA
<213> ORGANISM: Artificial Sequence
<220> FEATURE:
<223> OTHER INFORMATION: Oligonucleotide for CDR3 randomisation
<221> NAME/KEY: misc_feature
<222> LOCATION: (1)..(78)
<223> OTHER INFORMATION: "n" can be a,t, g or c
<221> NAME/KEY: misc_feature
<222> LOCATION: (1)..(78)
<223> OTHER INFORMATION: "m" can be a or c

<400> SEQUENCE: 43
```

```
aatctgggta ccgttgccga tgccmnnmnn mnnmnnmnnm nnmnnmnnmn nmnncacctt    60
gcagatgtag agtcccgt                                                 78
```

<210> SEQ ID NO 44
<211> LENGTH: 93
<212> TYPE: DNA
<213> ORGANISM: Artificial Sequence
<220> FEATURE:
<223> OTHER INFORMATION: Oligonucleotide for CDR3 randomisation
<221> NAME/KEY: misc_feature
<222> LOCATION: (29)..(30)
<223> OTHER INFORMATION: "x" can be a,t,g or c
<221> NAME/KEY: misc_feature
<222> LOCATION: (32)..(33)
<223> OTHER INFORMATION: "x" can be a,t,g or c
<221> NAME/KEY: misc_feature
<222> LOCATION: (35)..(36)
<223> OTHER INFORMATION: "x" can be a,t,g or c
<221> NAME/KEY: misc_feature
<222> LOCATION: (38)..(39)
<223> OTHER INFORMATION: "x" can be a,t,g or c
<221> NAME/KEY: misc_feature
<222> LOCATION: (41)..(42)
<223> OTHER INFORMATION: "x" can be a,t,g or c
<221> NAME/KEY: misc_feature
<222> LOCATION: (44)..(45)
<223> OTHER INFORMATION: "x" can be a,t,g or c
<221> NAME/KEY: misc_feature
<222> LOCATION: (48)..(48)
<223> OTHER INFORMATION: "x" can be a,t,g or c
<221> NAME/KEY: misc_feature
<222> LOCATION: (50)..(51)
<223> OTHER INFORMATION: "x" can be a,t,g or c
<221> NAME/KEY: misc_feature
<222> LOCATION: (53)..(54)
<223> OTHER INFORMATION: "x" can be a,t,g or c
<221> NAME/KEY: misc_feature
<222> LOCATION: (56)..(57)
<223> OTHER INFORMATION: "x" can be a,t,g or c
<221> NAME/KEY: misc_feature
<222> LOCATION: (59)..(60)
<223> OTHER INFORMATION: "x" can be a,t,g or c
<221> NAME/KEY: misc_feature
<222> LOCATION: (62)..(63)
<223> OTHER INFORMATION: "x" can be a,t,g or c
<221> NAME/KEY: misc_feature
<222> LOCATION: (65)..(66)
<223> OTHER INFORMATION: "x" can be a,t,g or c
<221> NAME/KEY: misc_feature
<222> LOCATION: (47)..(47)
<223> OTHER INFORMATION: "x" can be a,t,g or c

<400> SEQUENCE: 44

```
aatctgggta ccgttgccga tgcccagmnn mnnmnnmnnm nnmnnmnnmn nmnnmnnmnn    60
mnnmnnctcc accttgcaga tgtagagtcc cgt                                93
```

<210> SEQ ID NO 45
<211> LENGTH: 81
<212> TYPE: DNA
<213> ORGANISM: Artificial Sequence
<220> FEATURE:
<223> OTHER INFORMATION: Oligonucleotide for CDR3 randomisation
<221> NAME/KEY: misc_feature
<222> LOCATION: (1)..(81)
<223> OTHER INFORMATION: "n" can be a,t,g or c
<221> NAME/KEY: misc_feature
<222> LOCATION: (1)..(81)
<223> OTHER INFORMATION: "m" can be a or c

<400> SEQUENCE: 45

```
aatctgggta ccgttgccga tgccmnnmnn mnnmnngcam nnmnnmnnmn nmnnmnncac    60
```
cttgcagatg tagagtcccg t                                              81

<210> SEQ ID NO 46
<211> LENGTH: 87
<212> TYPE: DNA
<213> ORGANISM: Artificial Sequence
<220> FEATURE:
<223> OTHER INFORMATION: Oligonucleotide for CDR3 randomisation
<221> NAME/KEY: misc_feature
<222> LOCATION: (1)..(87)
<223> OTHER INFORMATION: "n" can be a,t,g or c
<221> NAME/KEY: misc_feature
<222> LOCATION: (1)..(87)
<223> OTHER INFORMATION: "m" can be a or c

<400> SEQUENCE: 46
aatctgggta ccgttgccga tgccmnnmnn mnnmnnmnng camnnmnnmn nmnnmnnmnn     60
mnncaccttg cagatgtaga gtcccgt                                        87

<210> SEQ ID NO 47
<211> LENGTH: 99
<212> TYPE: DNA
<213> ORGANISM: Artificial Sequence
<220> FEATURE:
<223> OTHER INFORMATION: Oligonucleotide for CDR3 randomisation
<221> NAME/KEY: misc_feature
<222> LOCATION: (1)..(99)
<223> OTHER INFORMATION: "n" can be a,c,t or g
<221> NAME/KEY: misc_feature
<222> LOCATION: (1)..(99)
<223> OTHER INFORMATION: "m" can be a or c

<400> SEQUENCE: 47
aatctgggta ccgttgccga tgccmnnmnn mnnmnnmnnm nngcamnnmn nmnnmnnmnn     60
mnnmnnmnnm nmnnccacct tgcagatgta gagtcccgt                           99

<210> SEQ ID NO 48
<211> LENGTH: 87
<212> TYPE: DNA
<213> ORGANISM: Artificial Sequence
<220> FEATURE:
<223> OTHER INFORMATION: Oligonucleotide for CDR3 randomisation
<221> NAME/KEY: misc_feature
<222> LOCATION: (1)..(87)
<223> OTHER INFORMATION: "n" can be a,t,g or c
<221> NAME/KEY: misc_feature
<222> LOCATION: (1)..(87)
<223> OTHER INFORMATION: "m" can be a or c
<221> NAME/KEY: misc_feature
<222> LOCATION: (1)..(87)
<223> OTHER INFORMATION: "r" can be a or g
<221> NAME/KEY: misc_feature
<222> LOCATION: (1)..(87)
<223> OTHER INFORMATION: "w" can be a or t

<400> SEQUENCE: 48
aatctgggta ccgttgccga tgccrwmnn mnnmnnmnng camnnmnnmn nmnnmnnmnn      60
mnncaccttg cagatgtaga gtcccgt                                        87

<210> SEQ ID NO 49
<211> LENGTH: 70
<212> TYPE: DNA
<213> ORGANISM: Artificial Sequence
<220> FEATURE:
<223> OTHER INFORMATION: Oligonucleotide for CTLA4 codon change

<400> SEQUENCE: 49
atgcacgtgg cccagcctgc tgtggtgctg gccagcagcc gtggcatcgc cagctttgtg     60

```
<210> SEQ ID NO 50
<211> LENGTH: 77
<212> TYPE: DNA
<213> ORGANISM: Artificial Sequence
<220> FEATURE:
<223> OTHER INFORMATION: Oligonucleotide for CTLA4 codon change

<400> SEQUENCE: 50
gccagctttg tgtgtgaata tgcgtctggc tataccatcg gcccgtactg catgggtgtg    60
cgtgtgaccg tgctgcg                                                  77

<210> SEQ ID NO 51
<211> LENGTH: 54
<212> TYPE: DNA
<213> ORGANISM: Artificial Sequence
<220> FEATURE:
<223> OTHER INFORMATION: Oligonucleotide for CTLA4 codon change

<400> SEQUENCE: 51
gtgcgtgtga ccgtgctgcg tcaggcggat agccaggtga ccgaagtttg cgcg          54

<210> SEQ ID NO 52
<211> LENGTH: 75
<212> TYPE: DNA
<213> ORGANISM: Artificial Sequence
<220> FEATURE:
<223> OTHER INFORMATION: Oligonucleotide for CTLA4 codon change

<400> SEQUENCE: 52
caggtgaccg aagtttgcgc ggcagcgatc aacatgggcg gtggcatcac cttcctggat    60
gattccatct gcacc                                                    75

<210> SEQ ID NO 53
<211> LENGTH: 66
<212> TYPE: DNA
<213> ORGANISM: Artificial Sequence
<220> FEATURE:
<223> OTHER INFORMATION: Oligonucleotide for CTLA4 codon change

<400> SEQUENCE: 53
cagaccctgg atggtcaggt tcacctggtt accgctggag gtgccggtgc agatggaatc    60
atccag                                                              66

<210> SEQ ID NO 54
<211> LENGTH: 57
<212> TYPE: DNA
<213> ORGANISM: Artificial Sequence
<220> FEATURE:
<223> OTHER INFORMATION: Oligonucleotide for CTLA4 codon change

<400> SEQUENCE: 54
cactttgcag atgtacagac cggtatccat ggcacgcaga ccctggatgg tcaggtt       57

<210> SEQ ID NO 55
<211> LENGTH: 66
<212> TYPE: DNA
<213> ORGANISM: Artificial Sequence
<220> FEATURE:
<223> OTHER INFORMATION: Oligonucleotide for CTLA4 codon change

<400> SEQUENCE: 55
```

-continued caggccatga ccgcattcgt aataagacgc atagatggtg ctatccactt tgcagatgta    60
cagacc    66

<210> SEQ ID NO 56
<211> LENGTH: 69
<212> TYPE: DNA
<213> ORGANISM: Artificial Sequence
<220> FEATURE:
<223> OTHER INFORMATION: Oligonucleotide for CTLA4 codon change

<400> SEQUENCE: 56
ctgggtaccg ttgccgatgc cagaatcgta gccatagcca ccggtggaca ggccatgacc    60
gcattcgta    69

<210> SEQ ID NO 57
<211> LENGTH: 672
<212> TYPE: DNA
<213> ORGANISM: Homo Sapiens
<220> FEATURE:
<221> NAME/KEY: CDS
<222> LOCATION: (109)..(453)
<223> OTHER INFORMATION: Polynucleotide encoding Human CTLA-4 cDNA

<400> SEQUENCE: 57
atggcttgcc ttggatttca gcggcacaag gctcagctga acctggctgc caggacctgg    60
ccctgcactc tcctgttttt tcttctcttc atccctgtct tctgcaaa gca atg cac    117
                                                      Ala Met His
                                                        1 gtg gcc cag cct gct gtg gta ctg gcc agc agc cga ggc atc gcc agc    165
Val Ala Gln Pro Ala Val Val Leu Ala Ser Ser Arg Gly Ile Ala Ser
   5                  10                  15 ttt gtg tgt gag tat gca tct cca ggc aaa gcc act gag gtc cgg gtg    213
Phe Val Cys Glu Tyr Ala Ser Pro Gly Lys Ala Thr Glu Val Arg Val
20                  25                  30                  35 aca gtg ctt cgg cag gct gac agc cag gtg act gaa gtc tgt gcg gca    261
Thr Val Leu Arg Gln Ala Asp Ser Gln Val Thr Glu Val Cys Ala Ala
                40                  45                  50 acc tac atg acg ggg aat gag ttg acc ttc cta gat gat tcc atc tgc    309
Thr Tyr Met Thr Gly Asn Glu Leu Thr Phe Leu Asp Asp Ser Ile Cys
            55                  60                  65 acg ggc acc tcc agt gga aat caa gtg aac ctc act atc caa gga ctg    357
Thr Gly Thr Ser Ser Gly Asn Gln Val Asn Leu Thr Ile Gln Gly Leu
        70                  75                  80 agg gcc atg gac acg gga ctc tac atc tgc aag gtg gag ctc atg tac    405
Arg Ala Met Asp Thr Gly Leu Tyr Ile Cys Lys Val Glu Leu Met Tyr
    85                  90                  95 cca ccg cca tac tac ctg ggc ata ggc aac gga acc cag att tat gta    453
Pro Pro Pro Tyr Tyr Leu Gly Ile Gly Asn Gly Thr Gln Ile Tyr Val
100                 105                 110                 115 attgatccag aaccgtgccc agattctgac ttcctcctct ggatccttgc agcagttagt    513
tcggggttgt tttttatag ctttctcctc acagctgttt ctttgagcaa aatgctaaag    573
aaaagaagcc ctcttacaac agggtctat gtgaaaatgc cccaacaga gccagaatgt    633 gaaaagcaat tcagccctta ttttattccc atcaattga    672

<210> SEQ ID NO 58
<211> LENGTH: 115
<212> TYPE: PRT
<213> ORGANISM: Homo Sapiens

<400> SEQUENCE: 58

```
Ala Met His Val Ala Gln Pro Ala Val Leu Ala Ser Ser Arg Gly
1               5                   10                  15

Ile Ala Ser Phe Val Cys Glu Tyr Ala Ser Pro Gly Lys Ala Thr Glu
                20                  25                  30

Val Arg Val Thr Val Leu Arg Gln Ala Asp Ser Gln Val Thr Glu Val
                35                  40                  45

Cys Ala Ala Thr Tyr Met Thr Gly Asn Glu Leu Thr Phe Leu Asp Asp
    50                  55                  60

Ser Ile Cys Thr Gly Thr Ser Ser Gly Asn Gln Val Asn Leu Thr Ile
65                  70                  75                  80

Gln Gly Leu Arg Ala Met Asp Thr Gly Leu Tyr Ile Cys Lys Val Glu
                85                  90                  95

Leu Met Tyr Pro Pro Pro Tyr Tyr Leu Gly Ile Gly Asn Gly Thr Gln
                100                 105                 110

Ile Tyr Val
        115
```

<210> SEQ ID NO 59
<211> LENGTH: 7
<212> TYPE: PRT
<213> ORGANISM: Homo Sapiens

<400> SEQUENCE: 59

```
Ser Pro Gly Lys Ala Thr Glu
1               5
```

<210> SEQ ID NO 60
<211> LENGTH: 14
<212> TYPE: PRT
<213> ORGANISM: Homo Sapiens

<400> SEQUENCE: 60

```
Ala Gly Cys Lys Asn Phe Phe Trp Lys Thr Phe Thr Ser Cys
1               5                   10
```

<210> SEQ ID NO 61
<211> LENGTH: 9
<212> TYPE: PRT
<213> ORGANISM: Homo Sapiens

<400> SEQUENCE: 61

```
Tyr Met Met Gly Asn Glu Leu Thr Phe
1               5
```

<210> SEQ ID NO 62
<211> LENGTH: 9
<212> TYPE: PRT
<213> ORGANISM: Homo Sapiens

<400> SEQUENCE: 62

```
Leu Met Tyr Pro Pro Pro Tyr Tyr Leu
1               5
```

<210> SEQ ID NO 63
<211> LENGTH: 9
<212> TYPE: PRT
<213> ORGANISM: Artificial Sequence
<220> FEATURE:
<223> OTHER INFORMATION: Haemagglutinin tag

<400> SEQUENCE: 63

```
Tyr Pro Tyr Asp Val Pro Asp Tyr Ala
1               5
```

<210> SEQ ID NO 64
<211> LENGTH: 11
<212> TYPE: PRT
<213> ORGANISM: Artificial Sequence
<220> FEATURE:
<223> OTHER INFORMATION: Sequence from anti-lysozyme antibody

<400> SEQUENCE: 64

```
Ser Gly Tyr Thr Ile Gly Pro Tyr Cys Met Gly
1               5                   10
```

<210> SEQ ID NO 65
<211> LENGTH: 10
<212> TYPE: PRT
<213> ORGANISM: Artificial Sequence
<220> FEATURE:
<223> OTHER INFORMATION: Sequence from anti-lysozyme antibody

<400> SEQUENCE: 65

```
Thr Tyr Met Met Gly Asn Glu Leu Thr Phe
1               5                   10
```

<210> SEQ ID NO 66
<211> LENGTH: 24
<212> TYPE: PRT
<213> ORGANISM: Artificial Sequence
<220> FEATURE:
<223> OTHER INFORMATION: Sequence from anti-lysozyme antibody

<400> SEQUENCE: 66

```
Asp Ser Thr Ile Tyr Ala Ser Tyr Tyr Glu Cys Gly His Gly Leu Ser
1               5                   10                  15

Thr Gly Gly Tyr Gly Tyr Asp Ser
            20
```

<210> SEQ ID NO 67
<211> LENGTH: 11
<212> TYPE: PRT
<213> ORGANISM: Homo Sapiens

<400> SEQUENCE: 67

```
Ser Gly Phe Thr Phe Ser Ser Tyr Ala Met Ser
1               5                   10
```

<210> SEQ ID NO 68
<211> LENGTH: 10
<212> TYPE: PRT
<213> ORGANISM: Homo Sapiens

<400> SEQUENCE: 68

```
Ala Ile Ser Gly Ser Gly Gly Ser Thr Tyr
1               5                   10
```

<210> SEQ ID NO 69
<211> LENGTH: 15
<212> TYPE: PRT
<213> ORGANISM: Homo Sapiens

<400> SEQUENCE: 69

```
Gly Trp Gly Leu Arg Gly Glu Glu Gly Asp Tyr Tyr Met Asp Val
1               5                   10                  15
```

<210> SEQ ID NO 70
<211> LENGTH: 21
<212> TYPE: PRT
<213> ORGANISM: Artificial Sequence
<220> FEATURE:
<223> OTHER INFORMATION: Flag tag

<400> SEQUENCE: 70

Ala Ala Ala Asp Tyr Lys Asp Asp Asp Lys Ala Ala Asp Tyr Lys
1               5                   10                  15

Asp Asp Asp Asp Lys
            20

<210> SEQ ID NO 71
<211> LENGTH: 14
<212> TYPE: PRT
<213> ORGANISM: Homo Sapiens

<400> SEQUENCE: 71

Ser Phe Val Cys Glu Tyr Ala Ser Pro Gly Lys Ala Thr Glu
1               5                   10

<210> SEQ ID NO 72
<211> LENGTH: 18
<212> TYPE: PRT
<213> ORGANISM: Artificial Sequence
<220> FEATURE:
<223> OTHER INFORMATION: sequence from fusion protein

<400> SEQUENCE: 72

Ser Phe Val Cys Glu Tyr Ala Ser Gly Tyr Thr Ile Gly Pro Tyr Cys
1               5                   10                  15

Met Gly

<210> SEQ ID NO 73
<211> LENGTH: 24
<212> TYPE: PRT
<213> ORGANISM: Artificial Sequence
<220> FEATURE:
<223> OTHER INFORMATION: sequence from fusion protein

<400> SEQUENCE: 73

Ser Phe Val Cys Glu Tyr Ala Ala Gly Cys Lys Asn Phe Phe Trp Lys
1               5                   10                  15

Thr Phe Thr Ser Cys Ala Thr Glu
            20

<210> SEQ ID NO 74
<211> LENGTH: 18
<212> TYPE: PRT
<213> ORGANISM: Homo Sapiens

<400> SEQUENCE: 74

Ser Phe Val Cys Glu Tyr Ala Ser Gly Phe Thr Phe Ser Ser Tyr Ala
1               5                   10                  15

Met Ser

<210> SEQ ID NO 75
<211> LENGTH: 15
<212> TYPE: PRT
<213> ORGANISM: Artificial Sequence
<220> FEATURE:
<223> OTHER INFORMATION: sequence from fusion protein containing the
      random sequence
<221> NAME/KEY: MISC_FEATURE

```
<222> LOCATION: (8)..(8)
<223> OTHER INFORMATION: "Xaa" can be any amino acid
<221> NAME/KEY: MISC_FEATURE
<222> LOCATION: (9)..(9)
<223> OTHER INFORMATION: "Xaa" can be any amino acid
<221> NAME/KEY: MISC_FEATURE
<222> LOCATION: (10)..(10)
<223> OTHER INFORMATION: "Xaa" can be any amino acid
<221> NAME/KEY: MISC_FEATURE
<222> LOCATION: (11)..(11)
<223> OTHER INFORMATION: "Xaa" can be any amino acid
<221> NAME/KEY: MISC_FEATURE
<222> LOCATION: (12)..(12)
<223> OTHER INFORMATION: "Xaa" can be any amino acid
<221> NAME/KEY: MISC_FEATURE
<222> LOCATION: (13)..(13)
<223> OTHER INFORMATION: "Xaa" can be any amino acid
<221> NAME/KEY: MISC_FEATURE
<222> LOCATION: (14)..(14)
<223> OTHER INFORMATION: "Xaa" can be any amino acid

<400> SEQUENCE: 75

Ser Phe Val Cys Glu Tyr Ala Xaa Xaa Xaa Xaa Xaa Xaa Xaa Gly
1               5                   10                  15

<210> SEQ ID NO 76
<211> LENGTH: 18
<212> TYPE: PRT
<213> ORGANISM: Artificial Sequence
<220> FEATURE:
<223> OTHER INFORMATION: sequence from fusion protein containing the
      random sequence
<221> NAME/KEY: MISC_FEATURE
<222> LOCATION: (8)..(8)
<223> OTHER INFORMATION: "Xaa" can be any amino acid
<221> NAME/KEY: MISC_FEATURE
<222> LOCATION: (9)..(9)
<223> OTHER INFORMATION: "Xaa" can be any amino acid
<221> NAME/KEY: MISC_FEATURE
<222> LOCATION: (10)..(10)
<223> OTHER INFORMATION: "Xaa" can be any amino acid
<221> NAME/KEY: MISC_FEATURE
<222> LOCATION: (11)..(11)
<223> OTHER INFORMATION: "Xaa" can be any amino acid
<221> NAME/KEY: MISC_FEATURE
<222> LOCATION: (12)..(12)
<223> OTHER INFORMATION: "Xaa" can be any amino acid
<221> NAME/KEY: MISC_FEATURE
<222> LOCATION: (13)..(13)
<223> OTHER INFORMATION: "Xaa" can be any amino acid
<221> NAME/KEY: MISC_FEATURE
<222> LOCATION: (14)..(14)
<223> OTHER INFORMATION: "Xaa" can be any amino acid
<221> NAME/KEY: MISC_FEATURE
<222> LOCATION: (15)..(15)
<223> OTHER INFORMATION: "Xaa" can be any amino acid
<221> NAME/KEY: MISC_FEATURE
<222> LOCATION: (17)..(17)
<223> OTHER INFORMATION: "Xaa" can be any amino acid

<400> SEQUENCE: 76

Ser Phe Val Cys Glu Tyr Ala Xaa Xaa Xaa Xaa Xaa Xaa Xaa Xaa Cys
1               5                   10                  15

Xaa Gly

<210> SEQ ID NO 77
<211> LENGTH: 21
<212> TYPE: PRT
<213> ORGANISM: Artificial Sequence
<220> FEATURE:
<223> OTHER INFORMATION: sequence from fusion protein containing the
      random sequence
<221> NAME/KEY: MISC_FEATURE
<222> LOCATION: (8)..(8)
```

```
<223> OTHER INFORMATION: "Xaa" can be any amino acid
<221> NAME/KEY: MISC_FEATURE
<222> LOCATION: (9)..(9)
<223> OTHER INFORMATION: "Xaa" can be any amino acid
<221> NAME/KEY: MISC_FEATURE
<222> LOCATION: (12)..(12)
<223> OTHER INFORMATION: "Xaa" can be any amino acid
<221> NAME/KEY: MISC_FEATURE
<222> LOCATION: (15)..(15)
<223> OTHER INFORMATION: "Xaa" can be any amino acid
<221> NAME/KEY: MISC_FEATURE
<222> LOCATION: (16)..(16)
<223> OTHER INFORMATION: "Xaa" can be any amino acid
<221> NAME/KEY: MISC_FEATURE
<222> LOCATION: (20)..(20)
<223> OTHER INFORMATION: "Xaa" can be any amino acid

<400> SEQUENCE: 77

Ser Phe Val Cys Glu Tyr Ala Xaa Xaa Ala Arg Xaa Ala Arg Xaa Xaa
1               5                  10                  15

Ala Arg Cys Xaa Gly
            20

<210> SEQ ID NO 78
<211> LENGTH: 14
<212> TYPE: PRT
<213> ORGANISM: Artificial Sequence
<220> FEATURE:
<223> OTHER INFORMATION: sequence from fusion protein containing the
      random sequence
<221> NAME/KEY: MISC_FEATURE
<222> LOCATION: (11)..(11)
<223> OTHER INFORMATION: "Xaa" can be any amino acid
<221> NAME/KEY: MISC_FEATURE
<222> LOCATION: (12)..(12)
<223> OTHER INFORMATION: "Xaa" can be any amino acid
<221> NAME/KEY: MISC_FEATURE
<222> LOCATION: (13)..(13)
<223> OTHER INFORMATION: "Xaa" can be any amino acid
<221> NAME/KEY: MISC_FEATURE
<222> LOCATION: (14)..(14)
<223> OTHER INFORMATION: "Xaa" can be any amino acid

<400> SEQUENCE: 78

Ser Phe Val Cys Glu Tyr Ala Ser Pro Gly Xaa Xaa Xaa Xaa
1               5                  10

<210> SEQ ID NO 79
<211> LENGTH: 14
<212> TYPE: PRT
<213> ORGANISM: Artificial Sequence
<220> FEATURE:
<223> OTHER INFORMATION: sequence from fusion protein containing the
      random sequence
<221> NAME/KEY: MISC_FEATURE
<222> LOCATION: (11)..(11)
<223> OTHER INFORMATION: "Xaa" can be any amino acid
<221> NAME/KEY: MISC_FEATURE
<222> LOCATION: (13)..(13)
<223> OTHER INFORMATION: "Xaa" can be any amino acid
<221> NAME/KEY: MISC_FEATURE
<222> LOCATION: (14)..(14)
<223> OTHER INFORMATION: "Xaa" can be any amino acid

<400> SEQUENCE: 79

Ser Phe Val Cys Glu Tyr Ala Ser Pro Gly Xaa Cys Xaa Xaa
1               5                  10

<210> SEQ ID NO 80
<211> LENGTH: 18
<212> TYPE: PRT
<213> ORGANISM: Artificial Sequence
```

```
<220> FEATURE:
<223> OTHER INFORMATION: sequence from fusion protein containing the
      random sequence
<221> NAME/KEY: MISC_FEATURE
<222> LOCATION: (8)..(8)
<223> OTHER INFORMATION: "Xaa" can be any amino acid
<221> NAME/KEY: MISC_FEATURE
<222> LOCATION: (9)..(9)
<223> OTHER INFORMATION: "Xaa" can be any amino acid
<221> NAME/KEY: MISC_FEATURE
<222> LOCATION: (10)..(10)
<223> OTHER INFORMATION: "Xaa" can be any amino acid
<221> NAME/KEY: MISC_FEATURE
<222> LOCATION: (11)..(11)
<223> OTHER INFORMATION: "Xaa" can be any amino acid
<221> NAME/KEY: MISC_FEATURE
<222> LOCATION: (12)..(12)
<223> OTHER INFORMATION: "Xaa" can be any amino acid
<221> NAME/KEY: MISC_FEATURE
<222> LOCATION: (13)..(13)
<223> OTHER INFORMATION: "Xaa" can be any amino acid
<221> NAME/KEY: MISC_FEATURE
<222> LOCATION: (14)..(14)
<223> OTHER INFORMATION: "Xaa" can be any amino acid
<221> NAME/KEY: MISC_FEATURE
<222> LOCATION: (15)..(15)
<223> OTHER INFORMATION: "Xaa" can be any amino acid

<400> SEQUENCE: 80

Ser Phe Val Cys Glu Tyr Ala Xaa Xaa Xaa Xaa Xaa Xaa Xaa Xaa Ala
1               5                  10                  15

Thr Glu

<210> SEQ ID NO 81
<211> LENGTH: 18
<212> TYPE: PRT
<213> ORGANISM: Artificial Sequence
<220> FEATURE:
<223> OTHER INFORMATION: sequence from fusion protein containing the
      random sequence
<221> NAME/KEY: MISC_FEATURE
<222> LOCATION: (8)..(8)
<223> OTHER INFORMATION: "Xaa" can be any amino acid
<221> NAME/KEY: MISC_FEATURE
<222> LOCATION: (9)..(9)
<223> OTHER INFORMATION: "Xaa" can be any amino acid
<221> NAME/KEY: MISC_FEATURE
<222> LOCATION: (10)..(10)
<223> OTHER INFORMATION: "Xaa" can be any amino acid
<221> NAME/KEY: MISC_FEATURE
<222> LOCATION: (11)..(11)
<223> OTHER INFORMATION: "Xaa" can be any amino acid
<221> NAME/KEY: MISC_FEATURE
<222> LOCATION: (12)..(12)
<223> OTHER INFORMATION: "Xaa" can be any amino acid
<221> NAME/KEY: MISC_FEATURE
<222> LOCATION: (13)..(13)
<223> OTHER INFORMATION: "Xaa" can be any amino acid
<221> NAME/KEY: MISC_FEATURE
<222> LOCATION: (15)..(15)
<223> OTHER INFORMATION: "Xaa" can be any amino acid

<400> SEQUENCE: 81

Ser Phe Val Cys Glu Tyr Ala Xaa Xaa Xaa Xaa Xaa Xaa Cys Xaa Ala
1               5                  10                  15

Thr Glu

<210> SEQ ID NO 82
<211> LENGTH: 24
<212> TYPE: PRT
<213> ORGANISM: Artificial Sequence
<220> FEATURE:
<223> OTHER INFORMATION: sequence from fusion protein containing the
```

```
        random sequence
<221> NAME/KEY: MISC_FEATURE
<222> LOCATION: (13)..(13)
<223> OTHER INFORMATION: "Xaa" can be any amino acid
<221> NAME/KEY: MISC_FEATURE
<222> LOCATION: (14)..(14)
<223> OTHER INFORMATION: "Xaa" can be any amino acid
<221> NAME/KEY: MISC_FEATURE
<222> LOCATION: (15)..(15)
<223> OTHER INFORMATION: "Xaa" can be any amino acid
<221> NAME/KEY: MISC_FEATURE
<222> LOCATION: (16)..(16)
<223> OTHER INFORMATION: "Xaa" can be any amino acid
<221> NAME/KEY: MISC_FEATURE
<222> LOCATION: (17)..(17)
<223> OTHER INFORMATION: "Xaa" can be any amino acid
<221> NAME/KEY: MISC_FEATURE
<222> LOCATION: (18)..(18)
<223> OTHER INFORMATION: "Xaa" can be any amino acid

<400> SEQUENCE: 82

Ser Phe Val Cys Glu Tyr Ala Ala Gly Cys Lys Asn Xaa Xaa Xaa Xaa
1               5                   10                  15

Xaa Xaa Thr Ser Cys Ala Thr Glu
            20

<210> SEQ ID NO 83
<211> LENGTH: 25
<212> TYPE: PRT
<213> ORGANISM: Artificial Sequence
<220> FEATURE:
<223> OTHER INFORMATION: sequence from fusion protein

<400> SEQUENCE: 83

Gln Val Thr Glu Val Cys Ala Ala Thr Tyr Met Met Gly Asn Glu Leu
1               5                   10                  15

Thr Phe Leu Asp Asp Ser Ile Cys Thr
            20                  25

<210> SEQ ID NO 84
<211> LENGTH: 25
<212> TYPE: PRT
<213> ORGANISM: Artificial Sequence
<220> FEATURE:
<223> OTHER INFORMATION: sequence from fusion protein

<400> SEQUENCE: 84

Gln Val Thr Glu Val Cys Ala Ala Ala Ile Asn Met Gly Gly Gly Ile
1               5                   10                  15

Thr Phe Leu Asp Asp Ser Ile Cys Thr
            20                  25

<210> SEQ ID NO 85
<211> LENGTH: 25
<212> TYPE: PRT
<213> ORGANISM: Artificial Sequence
<220> FEATURE:
<223> OTHER INFORMATION: sequence from fusion protein

<400> SEQUENCE: 85

Gln Val Thr Glu Val Cys Ala Ala Thr Tyr Pro Tyr Asp Val Pro Asp
1               5                   10                  15

Tyr Ala Leu Asp Asp Ser Ile Cys Thr
            20                  25

<210> SEQ ID NO 86
<211> LENGTH: 25
```

```
<212> TYPE: PRT
<213> ORGANISM: Artificial Sequence
<220> FEATURE:
<223> OTHER INFORMATION: sequence from fusion protein

<400> SEQUENCE: 86

Gln Val Thr Glu Val Cys Ala Ala Ala Ile Ser Gly Ser Gly Gly Ser
1               5                   10                  15

Thr Tyr Leu Asp Asp Ser Ile Cys Thr
            20                  25

<210> SEQ ID NO 87
<211> LENGTH: 25
<212> TYPE: PRT
<213> ORGANISM: Artificial Sequence
<220> FEATURE:
<223> OTHER INFORMATION: sequence from fusion sequence containing the
      random sequence 1
<221> NAME/KEY: MISC_FEATURE
<222> LOCATION: (11)..(11)
<223> OTHER INFORMATION: "Xaa" can be any amino acid
<221> NAME/KEY: MISC_FEATURE
<222> LOCATION: (12)..(12)
<223> OTHER INFORMATION: "Xaa" can be any amino acid
<221> NAME/KEY: MISC_FEATURE
<222> LOCATION: (14)..(14)
<223> OTHER INFORMATION: "Xaa" can be any amino acid

<400> SEQUENCE: 87

Gln Val Thr Glu Val Cys Ala Ala Thr Tyr Xaa Xaa Gly Xaa Glu Leu
1               5                   10                  15

Thr Phe Leu Asp Asp Ser Ile Cys Thr
            20                  25

<210> SEQ ID NO 88
<211> LENGTH: 25
<212> TYPE: PRT
<213> ORGANISM: Artificial Sequence
<220> FEATURE:
<223> OTHER INFORMATION: sequence from fusion protein containing the
      random sequence 2
<221> NAME/KEY: MISC_FEATURE
<222> LOCATION: (11)..(11)
<223> OTHER INFORMATION: "Xaa" can be any amino acid
<221> NAME/KEY: MISC_FEATURE
<222> LOCATION: (12)..(12)
<223> OTHER INFORMATION: "Xaa" can be any amino acid
<221> NAME/KEY: MISC_FEATURE
<222> LOCATION: (14)..(14)
<223> OTHER INFORMATION: "Xaa" can be any amino acid

<400> SEQUENCE: 88

Gln Val Thr Glu Val Cys Ala Ala Cys Tyr Xaa Xaa Gly Xaa Glu Leu
1               5                   10                  15

Thr Phe Leu Asp Asp Ser Ile Cys Thr
            20                  25

<210> SEQ ID NO 89
<211> LENGTH: 13
<212> TYPE: PRT
<213> ORGANISM: Artificial Sequence
<220> FEATURE:
<223> OTHER INFORMATION: sequence from fusion protein

<400> SEQUENCE: 89

Cys Lys Val Glu Leu Met Tyr Pro Pro Pro Tyr Tyr Leu
1               5                   10
```

```
<210> SEQ ID NO 90
<211> LENGTH: 27
<212> TYPE: PRT
<213> ORGANISM: Artificial Sequence
<220> FEATURE:
<223> OTHER INFORMATION: sequence from fusion protein

<400> SEQUENCE: 90

Cys Lys Val Asp Ser Thr Ile Tyr Ala Ser Tyr Tyr Glu Cys Gly His
1               5                   10                  15

Gly Leu Ser Thr Gly Gly Tyr Gly Tyr Asp Ser
            20                  25

<210> SEQ ID NO 91
<211> LENGTH: 18
<212> TYPE: PRT
<213> ORGANISM: Artificial Sequence
<220> FEATURE:
<223> OTHER INFORMATION: sequence from fusion protein

<400> SEQUENCE: 91

Cys Lys Val Glu Ala Gly Cys Lys Asn Phe Phe Trp Lys Thr Phe Thr
1               5                   10                  15

Ser Cys

<210> SEQ ID NO 92
<211> LENGTH: 18
<212> TYPE: PRT
<213> ORGANISM: Artificial Sequence
<220> FEATURE:
<223> OTHER INFORMATION: sequence from fusion protein

<400> SEQUENCE: 92

Cys Lys Val Gly Trp Gly Leu Arg Gly Glu Glu Gly Asp Tyr Tyr Met
1               5                   10                  15

Asp Val

<210> SEQ ID NO 93
<211> LENGTH: 14
<212> TYPE: PRT
<213> ORGANISM: Artificial Sequence
<220> FEATURE:
<223> OTHER INFORMATION: sequence from fusion protein containing the
      random sequence
<221> NAME/KEY: MISC_FEATURE
<222> LOCATION: (4)..(4)
<223> OTHER INFORMATION: "Xaa" can be any amino acid
<221> NAME/KEY: MISC_FEATURE
<222> LOCATION: (5)..(5)
<223> OTHER INFORMATION: "Xaa" can be any amino acid
<221> NAME/KEY: MISC_FEATURE
<222> LOCATION: (6)..(6)
<223> OTHER INFORMATION: "Xaa" can be any amino acid
<221> NAME/KEY: MISC_FEATURE
<222> LOCATION: (7)..(7)
<223> OTHER INFORMATION: "Xaa" can be any amino acid
<221> NAME/KEY: MISC_FEATURE
<222> LOCATION: (8)..(8)
<223> OTHER INFORMATION: "Xaa" can be any amino acid
<221> NAME/KEY: MISC_FEATURE
<222> LOCATION: (9)..(9)
<223> OTHER INFORMATION: "Xaa" can be any amino acid
<221> NAME/KEY: MISC_FEATURE
<222> LOCATION: (10)..(10)
<223> OTHER INFORMATION: "Xaa" can be any amino acid
<221> NAME/KEY: MISC_FEATURE
<222> LOCATION: (11)..(11)
<223> OTHER INFORMATION: "Xaa" can be any amino acid
<221> NAME/KEY: MISC_FEATURE
<222> LOCATION: (12)..(12)
```

```
<223> OTHER INFORMATION: "Xaa" can be any amino acid
<221> NAME/KEY: MISC_FEATURE
<222> LOCATION: (13)..(13)
<223> OTHER INFORMATION: "Xaa" can be any amino acid
<221> NAME/KEY: MISC_FEATURE
<222> LOCATION: (14)..(14)
<223> OTHER INFORMATION: "Xaa" can be any amino acid

<400> SEQUENCE: 93

Cys Lys Val Xaa Xaa Xaa Xaa Xaa Xaa Xaa Xaa Xaa Xaa Xaa
1               5                   10

<210> SEQ ID NO 94
<211> LENGTH: 18
<212> TYPE: PRT
<213> ORGANISM: Artificial Sequence
<220> FEATURE:
<223> OTHER INFORMATION: sequence from fusion protein containing the
      random sequence
<221> NAME/KEY: MISC_FEATURE
<222> LOCATION: (4)..(4)
<223> OTHER INFORMATION: "Xaa" can be any amino acid
<221> NAME/KEY: MISC_FEATURE
<222> LOCATION: (5)..(5)
<223> OTHER INFORMATION: "Xaa" can be any amino acid
<221> NAME/KEY: MISC_FEATURE
<222> LOCATION: (6)..(6)
<223> OTHER INFORMATION: "Xaa" can be any amino acid
<221> NAME/KEY: MISC_FEATURE
<222> LOCATION: (7)..(7)
<223> OTHER INFORMATION: "Xaa" can be any amino acid
<221> NAME/KEY: MISC_FEATURE
<222> LOCATION: (8)..(8)
<223> OTHER INFORMATION: "Xaa" can be any amino acid
<221> NAME/KEY: MISC_FEATURE
<222> LOCATION: (9)..(9)
<223> OTHER INFORMATION: "Xaa" can be any amino acid
<221> NAME/KEY: MISC_FEATURE
<222> LOCATION: (10)..(10)
<223> OTHER INFORMATION: "Xaa" can be any amino acid
<221> NAME/KEY: MISC_FEATURE
<222> LOCATION: (11)..(11)
<223> OTHER INFORMATION: "Xaa" can be any amino acid
<221> NAME/KEY: MISC_FEATURE
<222> LOCATION: (12)..(12)
<223> OTHER INFORMATION: "Xaa" can be any amino acid
<221> NAME/KEY: MISC_FEATURE
<222> LOCATION: (13)..(13)
<223> OTHER INFORMATION: "Xaa" can be any amino acid
<221> NAME/KEY: MISC_FEATURE
<222> LOCATION: (14)..(14)
<223> OTHER INFORMATION: "Xaa" can be any amino acid
<221> NAME/KEY: MISC_FEATURE
<222> LOCATION: (15)..(15)
<223> OTHER INFORMATION: "Xaa" can be any amino acid
<221> NAME/KEY: MISC_FEATURE
<222> LOCATION: (16)..(16)
<223> OTHER INFORMATION: "Xaa" can be any amino acid
<221> NAME/KEY: MISC_FEATURE
<222> LOCATION: (17)..(17)
<223> OTHER INFORMATION: "Xaa" can be any amino acid
<221> NAME/KEY: MISC_FEATURE
<222> LOCATION: (18)..(18)
<223> OTHER INFORMATION: "Xaa" can be any amino acid

<400> SEQUENCE: 94

Cys Lys Val Xaa Xaa Xaa Xaa Xaa Xaa Xaa Xaa Xaa Xaa Xaa Xaa Xaa
1               5                   10                  15

Xaa Xaa

<210> SEQ ID NO 95
<211> LENGTH: 14
<212> TYPE: PRT
<213> ORGANISM: Artificial Sequence
```

```
<220> FEATURE:
<223> OTHER INFORMATION: sequence from fusion protein containing the
      random sequence
<221> NAME/KEY: MISC_FEATURE
<222> LOCATION: (4)..(4)
<223> OTHER INFORMATION: "Xaa" can be any amino acid
<221> NAME/KEY: MISC_FEATURE
<222> LOCATION: (5)..(5)
<223> OTHER INFORMATION: "Xaa" can be any amino acid
<221> NAME/KEY: MISC_FEATURE
<222> LOCATION: (6)..(6)
<223> OTHER INFORMATION: "Xaa" can be any amino acid
<221> NAME/KEY: MISC_FEATURE
<222> LOCATION: (7)..(7)
<223> OTHER INFORMATION: "Xaa" can be any amino acid
<221> NAME/KEY: MISC_FEATURE
<222> LOCATION: (8)..(8)
<223> OTHER INFORMATION: "Xaa" can be any amino acid
<221> NAME/KEY: MISC_FEATURE
<222> LOCATION: (9)..(9)
<223> OTHER INFORMATION: "Xaa" can be any amino acid
<221> NAME/KEY: MISC_FEATURE
<222> LOCATION: (11)..(11)
<223> OTHER INFORMATION: "Xaa" can be any amino acid
<221> NAME/KEY: MISC_FEATURE
<222> LOCATION: (12)..(12)
<223> OTHER INFORMATION: "Xaa" can be any amino acid
<221> NAME/KEY: MISC_FEATURE
<222> LOCATION: (13)..(13)
<223> OTHER INFORMATION: "Xaa" can be any amino acid
<221> NAME/KEY: MISC_FEATURE
<222> LOCATION: (14)..(14)
<223> OTHER INFORMATION: "Xaa" can be any amino acid

<400> SEQUENCE: 95

Cys Lys Val Xaa Xaa Xaa Xaa Xaa Xaa Cys Xaa Xaa Xaa Xaa
1               5                   10

<210> SEQ ID NO 96
<211> LENGTH: 15
<212> TYPE: PRT
<213> ORGANISM: Artificial Sequence
<220> FEATURE:
<223> OTHER INFORMATION: sequence from fusion protein containing the
      random sequence
<221> NAME/KEY: MISC_FEATURE
<222> LOCATION: (4)..(10)
<223> OTHER INFORMATION: "Xaa" can be any amino acid
<221> NAME/KEY: MISC_FEATURE
<222> LOCATION: (12)..(15)
<223> OTHER INFORMATION: "Xaa" can be any amino acid

<400> SEQUENCE: 96

Cys Lys Val Xaa Xaa Xaa Xaa Xaa Xaa Xaa Cys Xaa Xaa Xaa Xaa
1               5                   10                  15

<210> SEQ ID NO 97
<211> LENGTH: 17
<212> TYPE: PRT
<213> ORGANISM: Artificial Sequence
<220> FEATURE:
<223> OTHER INFORMATION: sequence from fusion protein containing the
      random sequence
<221> NAME/KEY: MISC_FEATURE
<222> LOCATION: (4)..(11)
<223> OTHER INFORMATION: "Xaa" can be any amino acid
<221> NAME/KEY: MISC_FEATURE
<222> LOCATION: (12)..(17)
<223> OTHER INFORMATION: "Xaa" can be any amino acid

<400> SEQUENCE: 97

Cys Lys Val Xaa Xaa Xaa Xaa Xaa Xaa Xaa Xaa Cys Xaa Xaa Xaa Xaa
1               5                   10                  15
```

-continued

Xaa

<210> SEQ ID NO 98
<211> LENGTH: 21
<212> TYPE: PRT
<213> ORGANISM: Artificial Sequence
<220> FEATURE:
<223> OTHER INFORMATION: sequence from fusion protein containing the
      random sequence
<221> NAME/KEY: MISC_FEATURE
<222> LOCATION: (4)..(13)
<223> OTHER INFORMATION: "Xaa" can be any amino acid
<221> NAME/KEY: MISC_FEATURE
<222> LOCATION: (15)..(21)
<223> OTHER INFORMATION: "Xaa" can be any amino acid

<400> SEQUENCE: 98

Cys Lys Val Xaa Xaa Xaa Xaa Xaa Xaa Xaa Xaa Xaa Xaa Cys Xaa Xaa
1               5                   10                  15

Xaa Xaa Xaa Xaa Xaa
            20

<210> SEQ ID NO 99
<211> LENGTH: 13
<212> TYPE: PRT
<213> ORGANISM: Artificial Sequence
<220> FEATURE:
<223> OTHER INFORMATION: sequence from fusion protein containing the
      random sequence
<221> NAME/KEY: MISC_FEATURE
<222> LOCATION: (5)..(13)
<223> OTHER INFORMATION: "Xaa" can be any amino acid

<400> SEQUENCE: 99

Cys Lys Val Glu Xaa Xaa Xaa Xaa Xaa Xaa Xaa Xaa Xaa
1               5                   10

<210> SEQ ID NO 100
<211> LENGTH: 18
<212> TYPE: PRT
<213> ORGANISM: Artificial Sequence
<220> FEATURE:
<223> OTHER INFORMATION: sequence from fusion protein containing the
      random sequence
<221> NAME/KEY: MISC_FEATURE
<222> LOCATION: (4)..(18)
<223> OTHER INFORMATION: "Xaa" can be any amino acid

<400> SEQUENCE: 100

Cys Lys Val Glu Xaa Xaa Xaa Xaa Xaa Xaa Cys Xaa Xaa Xaa Xaa Xaa
1               5                   10                  15

Xaa Xaa

<210> SEQ ID NO 101
<211> LENGTH: 18
<212> TYPE: PRT
<213> ORGANISM: Artificial Sequence
<220> FEATURE:
<223> OTHER INFORMATION: sequence from fusion protein containing the
      random sequence
<221> NAME/KEY: MISC_FEATURE
<222> LOCATION: (10)..(15)
<223> OTHER INFORMATION: "Xaa" can be any amino acid

<400> SEQUENCE: 101

Cys Lys Val Glu Ala Gly Cys Lys Asn Xaa Xaa Xaa Xaa Xaa Xaa Thr
1               5                   10                  15

Ser Cys

<210> SEQ ID NO 102
<211> LENGTH: 10
<212> TYPE: PRT
<213> ORGANISM: Artificial Sequence
<220> FEATURE:
<223> OTHER INFORMATION: CDR1 and CDR3 inserts possessing randomly
      generated sequence

<400> SEQUENCE: 102

Leu Pro Ser Ser Asp Thr Arg Ala Tyr Ser
1               5                   10

<210> SEQ ID NO 103
<211> LENGTH: 8
<212> TYPE: PRT
<213> ORGANISM: Artificial Sequence
<220> FEATURE:
<223> OTHER INFORMATION: CDR1 and CDR# inserts possessing randomly
      generated sequence

<400> SEQUENCE: 103

Gln Glu Ser Gly Gly Arg Pro Gly
1               5

<210> SEQ ID NO 104
<211> LENGTH: 10
<212> TYPE: PRT
<213> ORGANISM: Artificial Sequence
<220> FEATURE:
<223> OTHER INFORMATION: CDR1 and CDR3 inserts possessing randomly
      generated sequence

<400> SEQUENCE: 104

Leu Pro Arg Gly Pro Pro Leu Leu Ser Leu
1               5                   10

<210> SEQ ID NO 105
<211> LENGTH: 7
<212> TYPE: PRT
<213> ORGANISM: Artificial Sequence
<220> FEATURE:
<223> OTHER INFORMATION: CDR1 and CDR3 inserts possessing randomly
      generated sequence

<400> SEQUENCE: 105

Ser Pro Gly Arg Cys Leu Asn
1               5

<210> SEQ ID NO 106
<211> LENGTH: 8
<212> TYPE: PRT
<213> ORGANISM: Artificial Sequence
<220> FEATURE:
<223> OTHER INFORMATION: CDR1 and CDR3 inserts possessing randomly
      generated sequence
<221> NAME/KEY: unsure
<222> LOCATION: (8)..(8)
<223> OTHER INFORMATION: stop codon but Glu when expressed in Tg-1 or
      JM109 of E. coli

<400> SEQUENCE: 106

Glu Trp Lys Arg Glu His Gly Gly
1               5

<210> SEQ ID NO 107
<211> LENGTH: 10
<212> TYPE: PRT

```
<213> ORGANISM: Artificial Sequence
<220> FEATURE:
<223> OTHER INFORMATION: CDR1 and CDR3 insers possessing randomly
      generated sequence

<400> SEQUENCE: 107

Leu Cys Pro Gly Ala Cys Gly Cys Val Tyr
1               5                   10

<210> SEQ ID NO 108
<211> LENGTH: 8
<212> TYPE: PRT
<213> ORGANISM: Artificial Sequence
<220> FEATURE:
<223> OTHER INFORMATION: CDR1 and CDR3 inserts possessing randomly
      generated sequence
<221> NAME/KEY: unsure
<222> LOCATION: (4)..(4)
<223> OTHER INFORMATION: stop codon but Glu when expressed in Tg-1 or
      JM109 strains of E.coli

<400> SEQUENCE: 108

Asn Ser Gly Glu Asn Glu Gly Gly
1               5

<210> SEQ ID NO 109
<211> LENGTH: 8
<212> TYPE: PRT
<213> ORGANISM: Artificial Sequence
<220> FEATURE:
<223> OTHER INFORMATION: CDR1 and CDR3 inserts possessing randomly
      generated sequence

<400> SEQUENCE: 109

Asp Lys Pro Val Thr Lys Ser Gly
1               5

<210> SEQ ID NO 110
<211> LENGTH: 7
<212> TYPE: PRT
<213> ORGANISM: Artificial Sequence
<220> FEATURE:
<223> OTHER INFORMATION: CDR1 and CDR3 inserts possessing randomly
      generated sequence
<221> NAME/KEY: unsure
<222> LOCATION: (7)..(7)
<223> OTHER INFORMATION: stop codon but Glu when expressed in Tg-1 or
      JM109 strains of E.coli

<400> SEQUENCE: 110

Ser Pro Gly Ala Cys Pro Glu
1               5

<210> SEQ ID NO 111
<211> LENGTH: 7
<212> TYPE: PRT
<213> ORGANISM: Artificial Sequence
<220> FEATURE:
<223> OTHER INFORMATION: CDR1 and CDR3 inserts possessing randomly
      generated sequence

<400> SEQUENCE: 111

Ser Pro Gly Lys Cys Asp Gln
1               5

<210> SEQ ID NO 112
<211> LENGTH: 7
<212> TYPE: PRT
<213> ORGANISM: Artificial Sequence
```

```
<220> FEATURE:
<223> OTHER INFORMATION: CDR1 and CDR3 inserts possessing randomly
      generated sequence

<400> SEQUENCE: 112

Ser Pro Gly Met Cys Ala Arg
1               5

<210> SEQ ID NO 113
<211> LENGTH: 11
<212> TYPE: PRT
<213> ORGANISM: Artificial Sequence
<220> FEATURE:
<223> OTHER INFORMATION: CDR1 and CDR3 inserts possessing randomly
      generated sequence
<221> NAME/KEY: unsure
<222> LOCATION: (8)..(8)
<223> OTHER INFORMATION: stop codon but Glu when expressed in Tg-1 or
      JM109 strains of E.coli

<400> SEQUENCE: 113

Pro Phe Leu Phe Leu Pro Cys Glu Phe Phe Phe
1               5                   10

<210> SEQ ID NO 114
<211> LENGTH: 11
<212> TYPE: PRT
<213> ORGANISM: Artificial Sequence
<220> FEATURE:
<223> OTHER INFORMATION: CDR1 and CDR3 inserts possessing randomly
      generated sequence

<400> SEQUENCE: 114

Trp Thr Leu Gly His His Lys Leu Cys Glu Gly
1               5                   10

<210> SEQ ID NO 115
<211> LENGTH: 10
<212> TYPE: PRT
<213> ORGANISM: Artificial Sequence
<220> FEATURE:
<223> OTHER INFORMATION: CDR1 and CDR3 inserts possessing randomly
      generated sequence

<400> SEQUENCE: 115

Leu Phe Thr Cys Leu Leu Ala Leu Cys Ser
1               5                   10

<210> SEQ ID NO 116
<211> LENGTH: 7
<212> TYPE: PRT
<213> ORGANISM: Artificial Sequence
<220> FEATURE:
<223> OTHER INFORMATION: CDR1 and CDR3 inserts possessing randomly
      generated sequence

<400> SEQUENCE: 116

Ser Pro Gly Glu Cys Tyr Gly
1               5

<210> SEQ ID NO 117
<211> LENGTH: 13
<212> TYPE: PRT
<213> ORGANISM: Artificial Sequence
<220> FEATURE:
<223> OTHER INFORMATION: CDR1 and CDR3 inserts possessing randomly
      generated sequence
<221> NAME/KEY: MISC_FEATURE
<222> LOCATION: (7)..(7)
```

<223> OTHER INFORMATION: "Xaa" can be any amino acid

<400> SEQUENCE: 117

Ser Trp Leu Ser Thr Thr Xaa Cys Leu Ser Ser Cys Ser
1               5                   10

<210> SEQ ID NO 118
<211> LENGTH: 7
<212> TYPE: PRT
<213> ORGANISM: Artificial Sequence
<220> FEATURE:
<223> OTHER INFORMATION: CDR1 and CDR3 inserts possessing randomly
      generated sequence
<221> NAME/KEY: unsure
<222> LOCATION: (4)..(4)
<223> OTHER INFORMATION: stop codon but Glu when expressed in Tg-1 or
      JM109 strains of E.coli

<400> SEQUENCE: 118

Ser Pro Gly Glu Cys Gln Asp
1               5

<210> SEQ ID NO 119
<211> LENGTH: 13
<212> TYPE: PRT
<213> ORGANISM: Artificial Sequence
<220> FEATURE:
<223> OTHER INFORMATION: CDR1 and CDR3 inserts possessing randomly
      generated sequence

<400> SEQUENCE: 119

Leu Leu Gly Ser Leu Leu Ser Cys Phe Ala Ser Leu Ser
1               5                   10

<210> SEQ ID NO 120
<211> LENGTH: 13
<212> TYPE: PRT
<213> ORGANISM: Artificial Sequence
<220> FEATURE:
<223> OTHER INFORMATION: CDR1 and CDR3 inserts possessing randomly
      generated sequence
<221> NAME/KEY: MISC_FEATURE
<222> LOCATION: (12)..(12)
<223> OTHER INFORMATION: "Xaa" can be any amino acid

<400> SEQUENCE: 120

Ser Pro Gly Ser Leu Leu Ser Cys Phe Ala Ser Xaa Ser
1               5                   10

<210> SEQ ID NO 121
<211> LENGTH: 7
<212> TYPE: PRT
<213> ORGANISM: Artificial Sequence
<220> FEATURE:
<223> OTHER INFORMATION: CDR1 and CDR3 inserts possessing randomly
      generated sequence

<400> SEQUENCE: 121

Ser Pro Gly Arg Cys Thr Asp
1               5

<210> SEQ ID NO 122
<211> LENGTH: 13
<212> TYPE: PRT
<213> ORGANISM: Artificial Sequence
<220> FEATURE:
<223> OTHER INFORMATION: CDR1 and CDR3 inserts possessing randomly
      generated sequence

```
<400> SEQUENCE: 122

Val Ile Cys His Ser Ser Val Cys Leu Ser Asp Val Cys
 1               5                  10

<210> SEQ ID NO 123
<211> LENGTH: 13
<212> TYPE: PRT
<213> ORGANISM: Artificial Sequence
<220> FEATURE:
<223> OTHER INFORMATION: CDR1 and CDR3 inserts possessing randomly
      generated sequence

<400> SEQUENCE: 123

Val Ile Cys His Ser Ser Val Cys Leu Ser Glu Val Cys
 1               5                  10

<210> SEQ ID NO 124
<211> LENGTH: 10
<212> TYPE: PRT
<213> ORGANISM: Artificial Sequence
<220> FEATURE:
<223> OTHER INFORMATION: CDR1 and CDR3 inserts possessing randomly
      generated sequence

<400> SEQUENCE: 124

Asp Leu Pro Ser Tyr Leu Ala Cys Ser Ile
 1               5                  10

<210> SEQ ID NO 125
<211> LENGTH: 7
<212> TYPE: PRT
<213> ORGANISM: Artificial Sequence
<220> FEATURE:
<223> OTHER INFORMATION: CDR1 and CDR3 inserts possessing randomly
      generated sequence

<400> SEQUENCE: 125

Ser Pro Gly Arg Cys Asp Ala
 1               5

<210> SEQ ID NO 126
<211> LENGTH: 14
<212> TYPE: PRT
<213> ORGANISM: Artificial Sequence
<220> FEATURE:
<223> OTHER INFORMATION: CDR1 and CDR3 inserts possessing randomly
      generated sequence

<400> SEQUENCE: 126

Ala Leu Cys Trp Asp Val Phe Tyr Cys Ser Phe Pro Ser Tyr
 1               5                  10

<210> SEQ ID NO 127
<211> LENGTH: 11
<212> TYPE: PRT
<213> ORGANISM: Artificial Sequence
<220> FEATURE:
<223> OTHER INFORMATION: CDR1 and CDR3 inserts possessing randomly
      generated sequence

<400> SEQUENCE: 127

Glu Leu Phe Gly His Ala Arg Tyr Cys Lys Gly
 1               5                  10

<210> SEQ ID NO 128
<211> LENGTH: 15
<212> TYPE: PRT
```

```
<213> ORGANISM: Artificial Sequence
<220> FEATURE:
<223> OTHER INFORMATION: CDR1 and CDR3 inserts possessing randomly
      generated sequence
<221> NAME/KEY: unsure
<222> LOCATION: (7)..(7)
<223> OTHER INFORMATION: Stop codon but Glu when expressed in Tg-1 or
      JM109 strains of E.coli

<400> SEQUENCE: 128

Val Ser Ile Thr Ser Pro Glu Leu Cys Pro Val Lys Val Phe Asp
1               5                   10                  15

<210> SEQ ID NO 129
<211> LENGTH: 7
<212> TYPE: PRT
<213> ORGANISM: Artificial Sequence
<220> FEATURE:
<223> OTHER INFORMATION: CDR1 and CDR3 inserts possessing randomly
      generated sequence
<221> NAME/KEY: unsure
<222> LOCATION: (6)..(6)
<223> OTHER INFORMATION: Stop codon but Glu when expressed in Tg-1 or
      JM109 strains of E.coli

<400> SEQUENCE: 129

Ser Pro Gly Lys Val Glu Asn
1               5

<210> SEQ ID NO 130
<211> LENGTH: 8
<212> TYPE: PRT
<213> ORGANISM: Artificial Sequence
<220> FEATURE:
<223> OTHER INFORMATION: CDR1 and CDR3 inserts possessing randomly
      generated sequence

<400> SEQUENCE: 130

Leu Phe Val Pro Phe Val Ser Pro
1               5

<210> SEQ ID NO 131
<211> LENGTH: 7
<212> TYPE: PRT
<213> ORGANISM: Artificial Sequence
<220> FEATURE:
<223> OTHER INFORMATION: CDR1 and CDR3 inserts possessing randomly
      generated sequence

<400> SEQUENCE: 131

Ser Pro Gly Asp Leu Trp Val
1               5

<210> SEQ ID NO 132
<211> LENGTH: 15
<212> TYPE: PRT
<213> ORGANISM: Artificial Sequence
<220> FEATURE:
<223> OTHER INFORMATION: CDR1 and CDR3 inserts possessing randomly
      generated sequence

<400> SEQUENCE: 132

Glu Ser Gly Leu Ser Pro Val Ser Pro Cys Ser Leu Tyr Ser Leu
1               5                   10                  15

<210> SEQ ID NO 133
<211> LENGTH: 8
<212> TYPE: PRT
<213> ORGANISM: Artificial Sequence
```

```
<220> FEATURE:
<223> OTHER INFORMATION: CDR1 and CDR3 inserts possessing randomly
      generated sequence

<400> SEQUENCE: 133

Thr Ser Ala Asn Gly Pro Tyr Gly
1               5

<210> SEQ ID NO 134
<211> LENGTH: 10
<212> TYPE: PRT
<213> ORGANISM: Artificial Sequence
<220> FEATURE:
<223> OTHER INFORMATION: CDR1 and CDR3 inserts possessing randomly
      generated sequence

<400> SEQUENCE: 134

Pro Trp Ala Tyr Arg Phe Leu Ala Val Leu
1               5                   10

<210> SEQ ID NO 135
<211> LENGTH: 8
<212> TYPE: PRT
<213> ORGANISM: Artificial Sequence
<220> FEATURE:
<223> OTHER INFORMATION: CDR1 and CDR3 inserts possessing randomly
      generated sequence

<400> SEQUENCE: 135

Arg Lys Thr Arg Glu Lys Tyr Gly
1               5

<210> SEQ ID NO 136
<211> LENGTH: 12
<212> TYPE: PRT
<213> ORGANISM: Artificial Sequence
<220> FEATURE:
<223> OTHER INFORMATION: CDR1 and CDR3 inserts possessing randomly
      generated sequence

<400> SEQUENCE: 136

Glu Leu Met Tyr Pro Pro Pro Tyr Tyr Leu Gly Ile
1               5                   10

<210> SEQ ID NO 137
<211> LENGTH: 7
<212> TYPE: PRT
<213> ORGANISM: Artificial Sequence
<220> FEATURE:
<223> OTHER INFORMATION: CDR1 and CDR3 inserts possessing randomly
      generated sequence

<400> SEQUENCE: 137

Ser Pro Gly Gln Glu Leu Thr
1               5

<210> SEQ ID NO 138
<211> LENGTH: 15
<212> TYPE: PRT
<213> ORGANISM: Artificial Sequence
<220> FEATURE:
<223> OTHER INFORMATION: CDR1 and CDR3 inserts possessing randomly
      generated sequence

<400> SEQUENCE: 138

Glu Leu Phe Phe Leu Leu Tyr Ala Pro Cys Tyr Leu Phe Gln Arg
1               5                   10                  15
```

```
<210> SEQ ID NO 139
<211> LENGTH: 5
<212> TYPE: PRT
<213> ORGANISM: Homo Sapiens
<220> FEATURE:
<221> NAME/KEY: domain
<222> LOCATION: (1)..(5)
<223> OTHER INFORMATION: V-like beta strand sequence

<400> SEQUENCE: 139

Ala Gly Phe Cys Cys
1               5

<210> SEQ ID NO 140
<211> LENGTH: 4
<212> TYPE: PRT
<213> ORGANISM: Homo Sapiens

<400> SEQUENCE: 140

Phe Trp Lys Thr
1

<210> SEQ ID NO 141
<211> LENGTH: 5
<212> TYPE: PRT
<213> ORGANISM: Homo Sapiens

<400> SEQUENCE: 141

Gly Phe Cys Cys Cys
1               5

<210> SEQ ID NO 142
<211> LENGTH: 6
<212> TYPE: PRT
<213> ORGANISM: Artificial Sequence
<220> FEATURE:
<223> OTHER INFORMATION: CDR1 and CDR3 inserts possessing randomly
      generated sequence

<400> SEQUENCE: 142

Ser Pro Glu Cys Gln Asp
1               5
```